United States Patent
Agaugue et al.

(10) Patent No.: US 10,752,668 B2
(45) Date of Patent: Aug. 25, 2020

(54) LENTIVIRAL VECTORS FOR REGULATED EXPRESSION OF A CHIMERIC ANTIGEN RECEPTOR MOLECULE

(71) Applicants: THERAVECTYS, Paris (FR); INSTITUT CURIE, Paris (FR); CENTRE NATIONAL DE LA RECHERCHE SCIENTIFIQUE, Paris (FR); UNIVERSITE PIERRE ET MARIE CURIE, Paris (FR); INSTITUT NATIONAL DE LA SANTE ET DE LA RECHERCHE MEDICALE (INSERM), Paris (FR)

(72) Inventors: Sophie Agaugue, Paris (FR); Lorenzo Tibaldi, Paris (FR); Klervi Even-Desrumaux, Antony (FR); Dmitry Trubetskoy, Arcueil (FR); Franck Perez, Paris (FR); Sebastian Amigorena, Paris (FR); Cécile Bauche, Paris (FR)

(73) Assignees: Theravectys, Paris (FR); Institut Curie, Paris (FR); Centre National de la Recherche Scientifique, Paris (FR); Sorbonne Universite, Paris (FR); Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 15/327,517

(22) PCT Filed: Jul. 24, 2015

(86) PCT No.: PCT/EP2015/067090
§ 371 (c)(1),
(2) Date: Jan. 19, 2017

(87) PCT Pub. No.: WO2016/012623
PCT Pub. Date: Jan. 28, 2016

(65) Prior Publication Data
US 2017/0166623 A1    Jun. 15, 2017

Related U.S. Application Data

(60) Provisional application No. 62/155,811, filed on May 1, 2015, provisional application No. 62/028,889, filed on Jul. 25, 2014.

(30) Foreign Application Priority Data

Jun. 29, 2015    (EP) .................................... 15306036

(51) Int. Cl.
  *C07K 16/30*    (2006.01)
  *G01N 33/574*   (2006.01)
  *C07K 16/28*    (2006.01)
  *C07K 14/705*   (2006.01)
  *C12N 5/0783*   (2010.01)
  *A61K 35/17*    (2015.01)
  *C07K 16/00*    (2006.01)
  *A61K 38/00*    (2006.01)

(52) U.S. Cl.
  CPC ........ *C07K 14/70503* (2013.01); *A61K 35/17* (2013.01); *C07K 16/00* (2013.01); *C12N 5/0636* (2013.01); *C12N 5/0646* (2013.01); *A61K 38/00* (2013.01); *C07K 2317/622* (2013.01); *C07K 2319/00* (2013.01); *C07K 2319/03* (2013.01); *C07K 2319/22* (2013.01); *C12N 2510/00* (2013.01); *C12N 2799/027* (2013.01)

(58) Field of Classification Search
None
See application file for complete search history.

(56) References Cited

U.S. PATENT DOCUMENTS

| | | | |
|---|---|---|---|
| 8,293,500 B2 * | 10/2012 | Wiley | G01N 33/5008 435/70.1 |
| 9,856,322 B2 * | 1/2018 | Campana | C07K 16/2866 |
| 10,494,434 B2 * | 12/2019 | Riddell | A61K 38/1774 |
| 2002/0155578 A1 * | 10/2002 | Szostak | C07K 14/00 435/226 |
| 2003/0118592 A1 * | 6/2003 | Ledbetter | C07K 16/2809 424/178.1 |
| 2005/0032173 A1 | 2/2005 | Rojas | |
| 2012/0149101 A1 * | 6/2012 | Perez | C12N 15/85 435/348 |
| 2013/0071414 A1 * | 3/2013 | Dotti | C12N 5/0636 424/184.1 |

(Continued)

FOREIGN PATENT DOCUMENTS

| | | |
|---|---|---|
| EP | 2 147 683 A1 | 1/2010 |
| WO | 2008/105968 A1 | 9/2008 |

(Continued)

OTHER PUBLICATIONS

Boncompain et al., Synchronization of secretory protein traffic in populations of cells Nature Methods | vol. 9 No. 5 | May 2012 | 493-499.*

(Continued)

*Primary Examiner* — Maria G Leavitt
(74) *Attorney, Agent, or Firm* — W&C IP

(57) ABSTRACT

The invention relates to the regulated expression of a chimeric antigen receptor (CAR) within a lentiviral vector. The CAR comprises a hook-binding domain that interacts with a hook, preferably encoded by the same lentiviral vector, which prevents proper processing and release of the CAR to the cell membrane. The invention encompasses vectors, methods of making the vectors, and methods of using them, including medicinal uses. The vectors can be used for administration to humans to induce immune responses and to treat cancers and tumors.

5 Claims, 11 Drawing Sheets
Specification includes a Sequence Listing.

(56) References Cited

U.S. PATENT DOCUMENTS

2017/0267756 A1* 9/2017 Riddell .................. A61K 35/17
2018/0200298 A1* 7/2018 Jensen .................. C07K 14/705

FOREIGN PATENT DOCUMENTS

WO      WO 2010142785      * 12/2010
WO         2014/059173 A2    4/2014

OTHER PUBLICATIONS

Dotti et al Design and Development of Therapies using Chimeric Antigen Receptor-Expressing T cellsImmunol Rev. 2014 Jan.; 257(1): pp. 1-34.*

* cited by examiner

| | B2M | HLA-A | HLA-DR | EEF1A1 | UBC | HLA-C | HLA-B | HLA-E | HLA-F |
|---|---|---|---|---|---|---|---|---|---|
| kidney | 5.18 | 3.40 | 37.73 | 4.33 | 0.41 | 8.39 | 3.40 | 1.99 | 3.64 |
| smooth muscle | 6.40 | 5.66 | 0.74 | 12.04 | 1.03 | 5.93 | 5.61 | 2.22 | 5.59 |
| liver | 2.90 | 7.38 | 12.27 | 1.38 | 0.28 | 14.65 | 7.38 | 4.60 | 6.96 |
| heart | 2.27 | 21.68 | 29.32 | 0.27 | 0.53 | 22.62 | 21.68 | 7.18 | 15.91 |
| skeletal muscle | 1.00 | 1.00 | 1.00 | 1.00 | 1.00 | 1.00 | 1.00 | 1.00 | 1.00 |
| BDCA+ DCs | 15.91 | 64.29 | 913.64 | 9.21 | 1.22 | 27.15 | 64.29 | 15.78 | 41.02 |
| CD8+ T cells | 18.68 | 64.59 | 9.77 | 8.79 | 0.72 | 36.28 | 64.59 | 27.61 | 73.23 |
| CD4+ T cells | 14.66 | 58.80 | 38.18 | 10.26 | 0.84 | 38.23 | 58.80 | 30.57 | 65.46 |

FIGURE 2

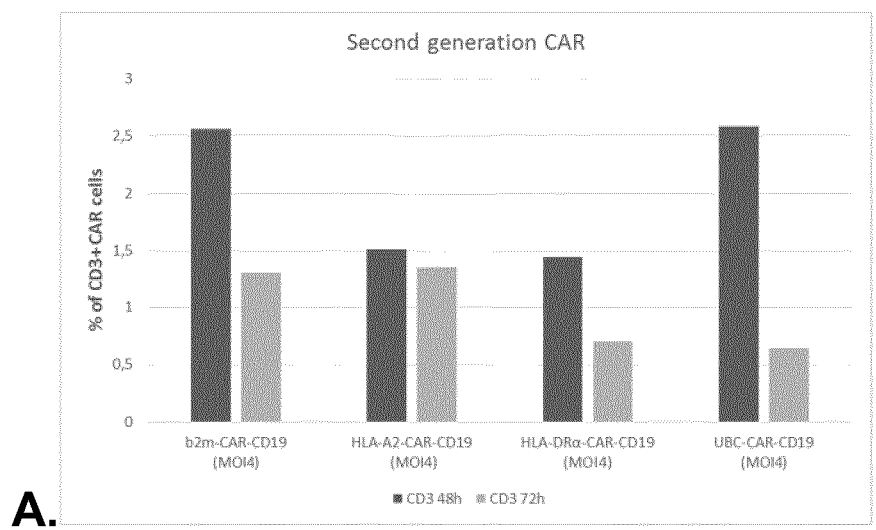
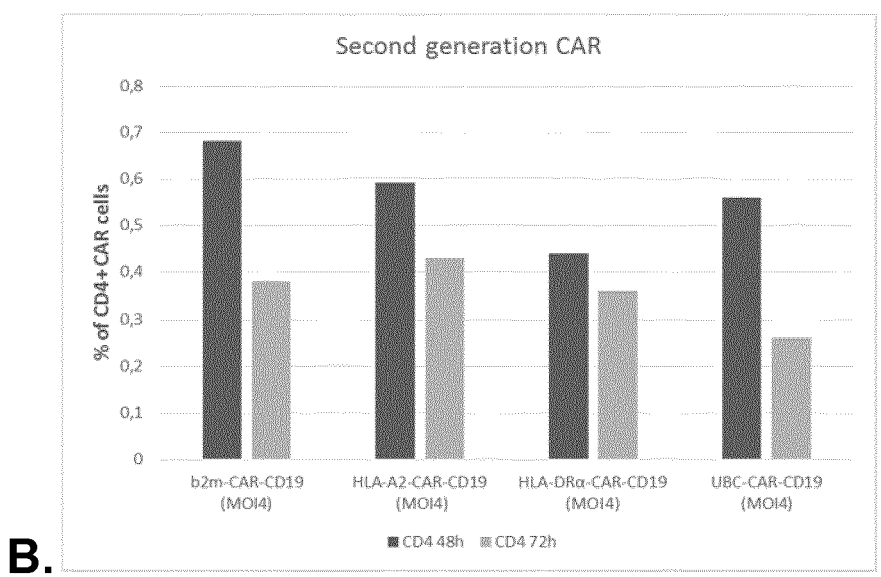
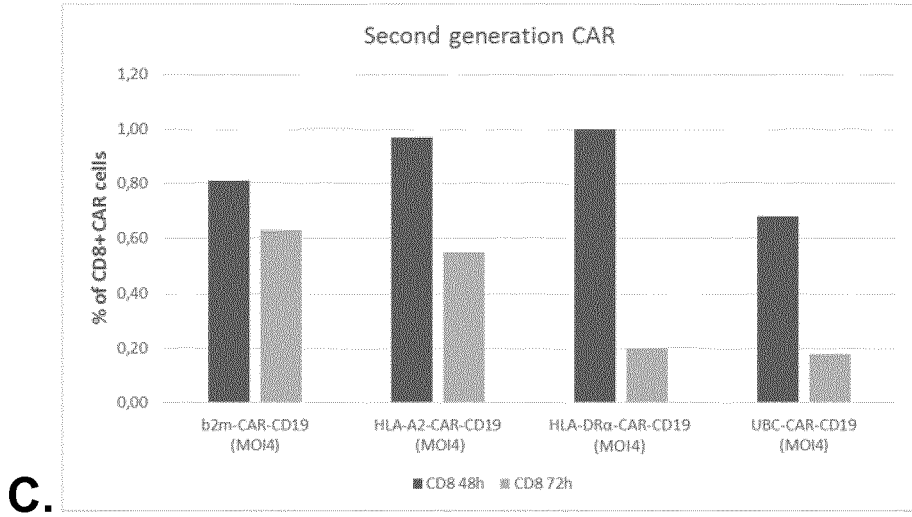
FIGURE 3

A.
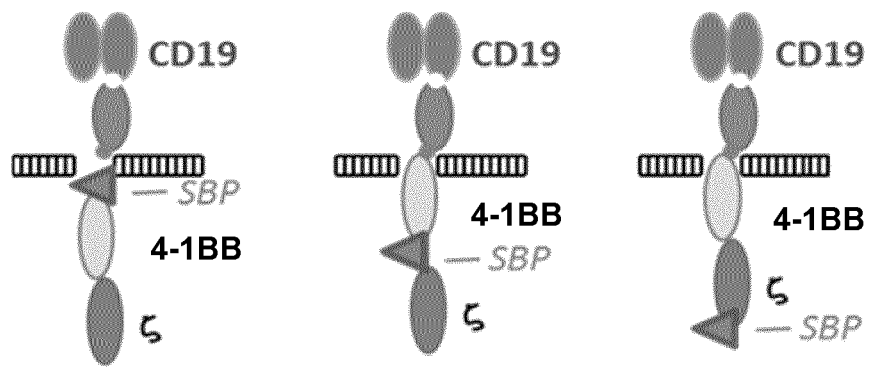
B.
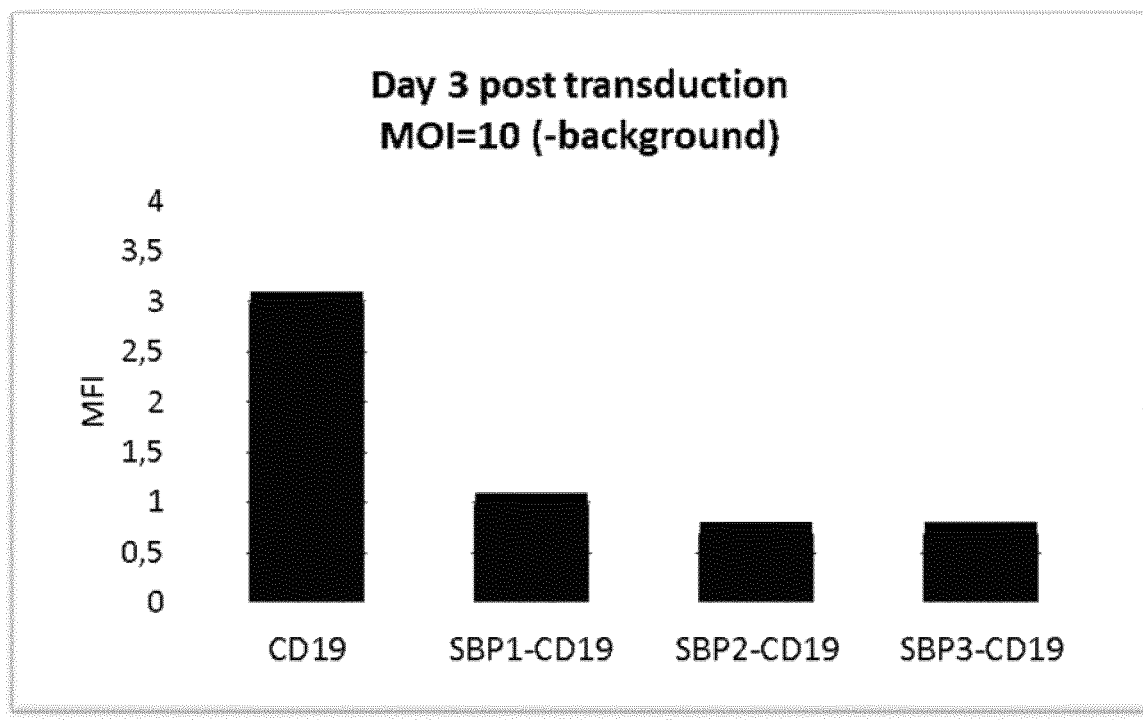
FIGURE 5

A.
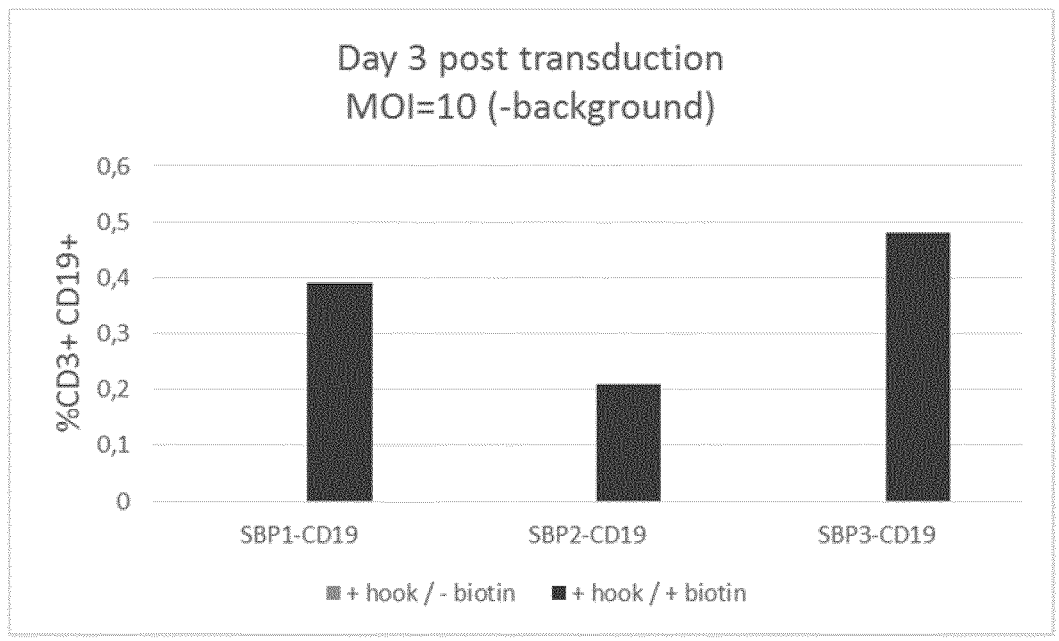
B.
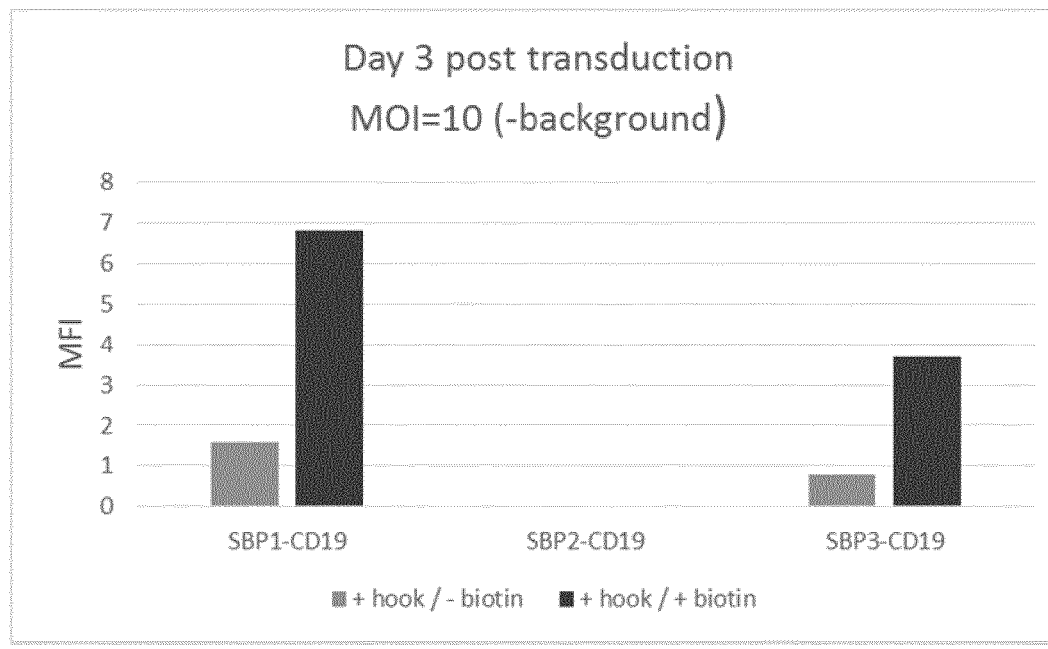
FIGURE 6

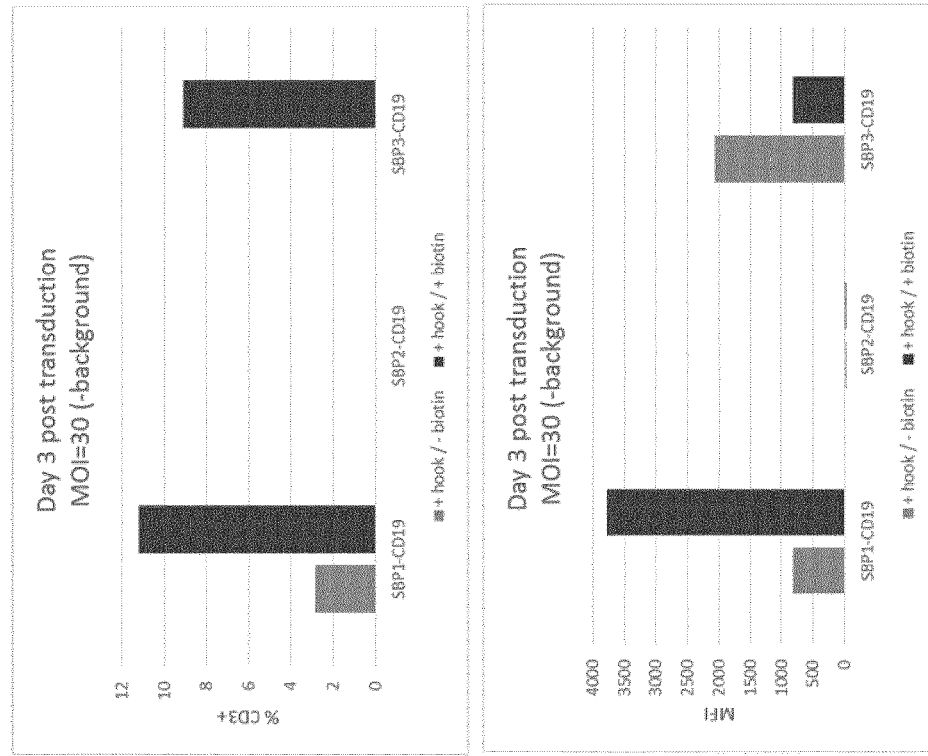
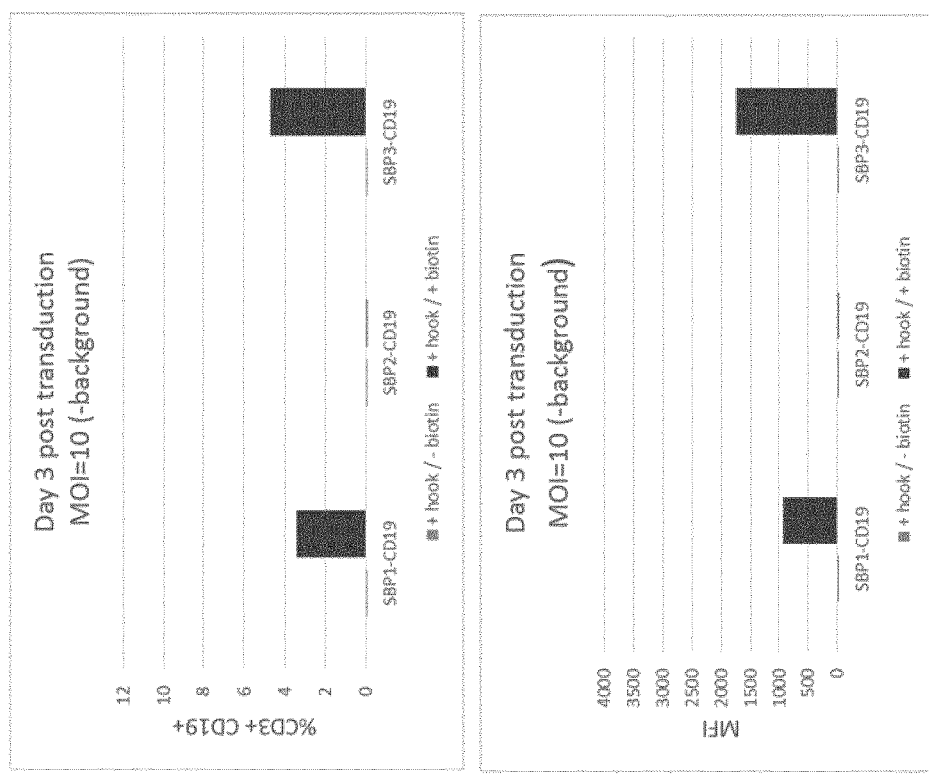
FIGURE 7

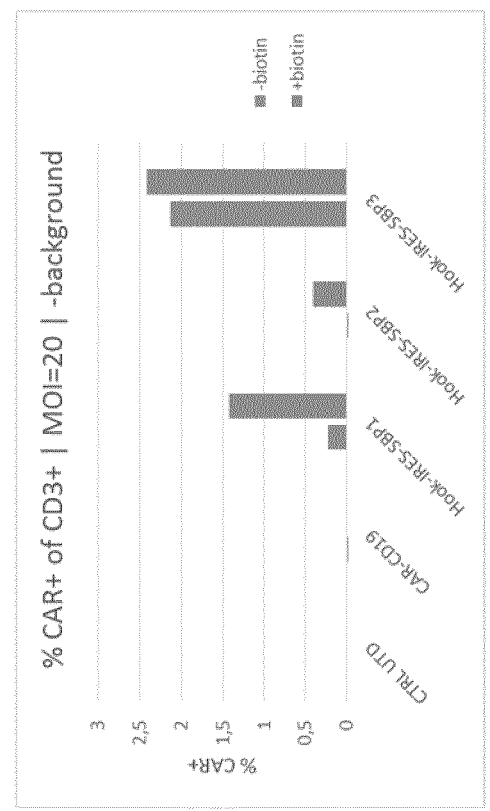
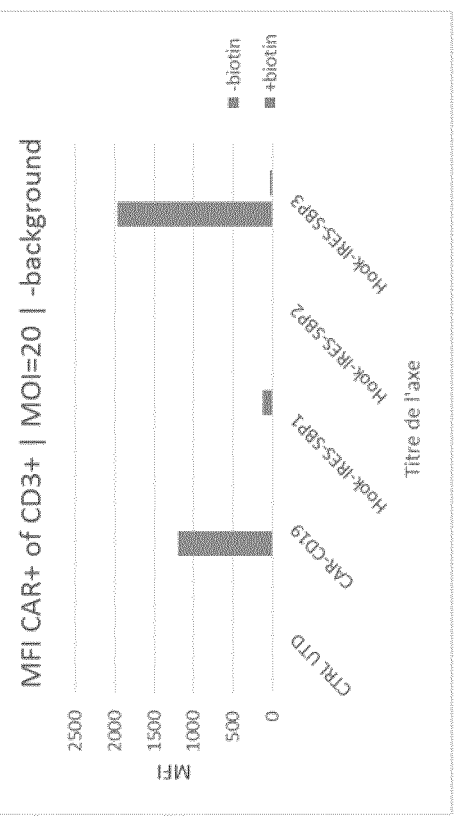
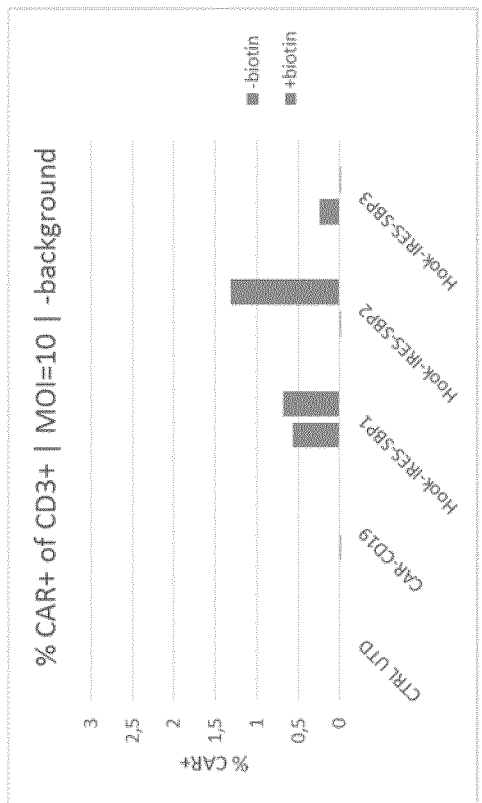
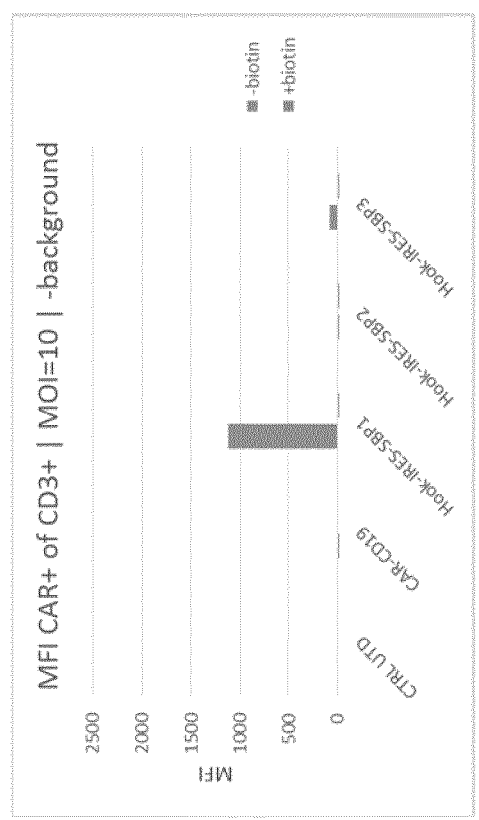
FIGURE 8

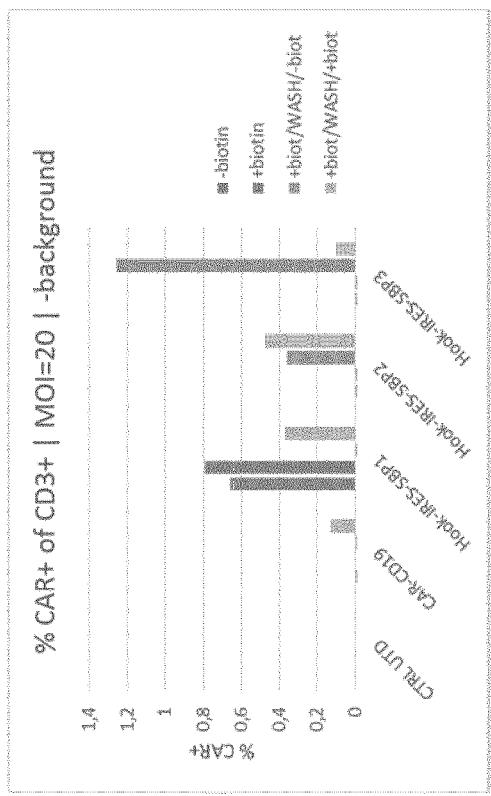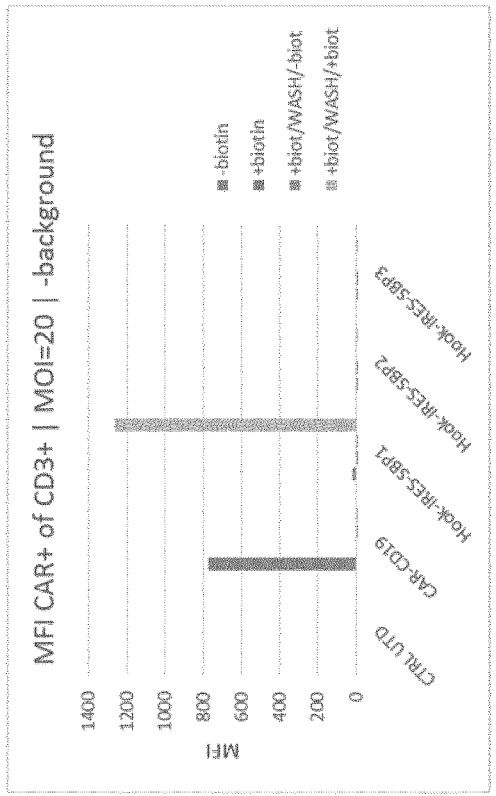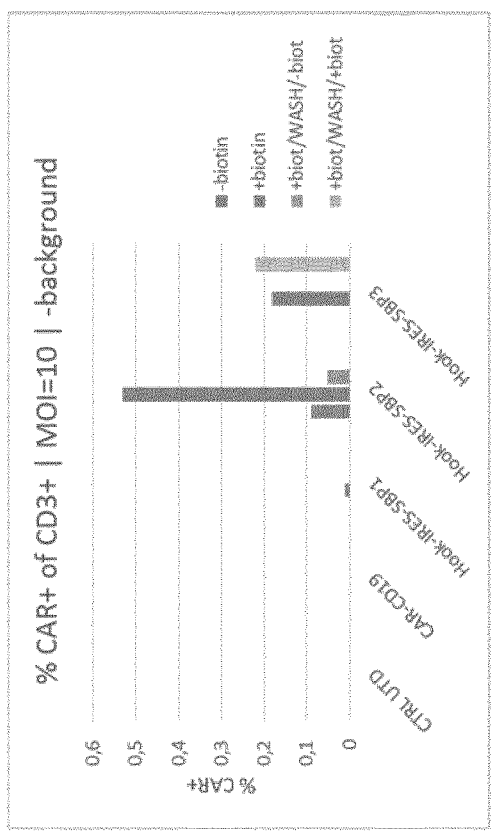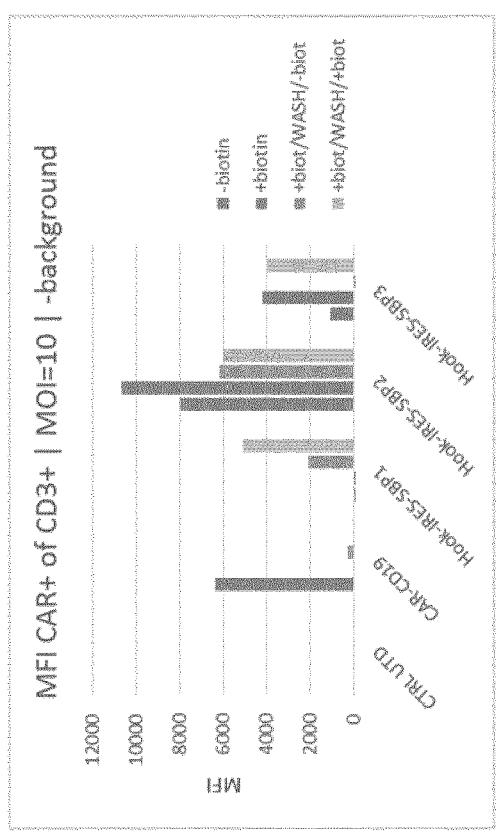
FIGURE 9

A.

ATGGCCCTGCCTGTGACAGCCCTGCTGCTGCCCCTGGCTCTCCTGCTGCATGCCGCCAGACCCGCTAGCGA
CATCCAGATGACCCAGACCACCAGCAGCCTGAGCGCCAGCCTGGGCGACAGAGTGACCATCAGCTGCCGGG
CCAGCCAGGACATCAGCAAGTACCTGAACTGGTATCAGCAGAAACCCGACGGCACCGTGAAGCTGCTGATC
TACCACACCAGCCGGCTCCACAGCGGCGTGCCCAGCAGATTTTCTGGCAGCGGCAGCGGCACCGACTACAG
CCTGACCATCTCCAACCTGGAACAGGAAGATATCGCTACCTACTTCTGTCAGCAAGGCAACACCCTGCCCT
ACACCTTCGGCGGAGGCACCAAGCTGGAAATCACCGGCGGAGGCGGAAGTGGAGGTGGAGGATCTGGCGGC
GGAGGCTCCGAAGTGAAGCTGCAGGAAAGCGGCCCTGGCCTCGTGGCCCCTAGCCAGAGCCTGTCCGTGAC
CTGTACCGTGTCCGGCGTGTCCCTGCCCGACTACGGCGTGTCCTGGATCAGACAGCCTCCCAGAAAGGGCC
TGGAATGGCTGGGCGTGATCTGGGGCAGCGAGACAACCTACTACAACAGCGCCCTGAAGTCCCGGCTGACC
ATCATCAAGGACAACAGCAAGAGCCAGGTGTTCCTGAAGATGAACAGCCTGCAGACCGACGACACCGCCAT
CTACTACTGCGCCAAGCACTACTACTACGGCGGCAGCTACGCCATGGACTACTGGGGCCAGGGCACCAGCG
TGACCGTGTCCAGCCATATG*GCCCTGAGCAACAGCATCATGTACTTCAGCCACTTCGTGCCCGTGTTTCTG*
*CCCGCCAAGCCCACCACCACCCCTGCCCCTAGACCTCCCACCCCAGCCCCAACAATCGCCAGCCAGCCTCT*
*GTCCCTGCGGCCCGAAGCCTGTAGACCTGCTGCCGGCGGAGCCGTGCACACCAGAGGCCTGGA*TATCTACA
TCTGGGCCCCTCTGGCCGGCACCTGTGGCGTGCTGCTGCTGAGCCTGGTGATCACA<u>AAGCGGGGCAGAAAG</u>
<u>AAGCTGCTGTACATCTTCAAGCAGCCATTCATGCGGCCCGTGCAGACCACCCAGGAAGAGGACGGCTGCAG</u>
<u>CTGCCGGTTCCCCGAGGAAGAGGAAGGCGGCTGCGAACTG</u>CCCAAGCTGTGCTACCTGCTGGACGGCATCC
TGTTCATCTATGGCGTGATCCTGACCGCCCTGTTCCTGAGAGTGAAGTTCAGCAGAAGCGCCGACGCCCCT
GCCTACCAGCAGGGCCAGAACCAGCTGTACAACGAGCTGAACCTGGGCAGACGGGAAGAGTACGACGTGCT
GGACAAGCGGAGAGGCCGGGACCCTGAGATGGGCGGCAAGCCCCAGCGGCGGAAGAACCCTCAGGAAGGCC
TGTATAACGAACTGCAGAAAGACAAGATGGCCGAGGCCTACAGCGAGATCGGCATGAAGGGCGAGCGGCGG
AGAGGCAAGGGCCACGATGGCCTGTAC

B.

MALPVTALLLPLALLLHAARPASDIQMTQTTSSLSASLGDRVTISCRASQDISKYLNWYQQKPDGTVKLLI
YHTSRLHSGVPSRFSGSGSGTDYSLTISNLEQEDIATYFCQQGNTLPYTFGGGTKLEITGGGGSGGGGSGG
GGSEVKLQESGPGLVAPSQSLSVTCTVSGVSLPDYGVSWIRQPPRKGLEWLGVIWGSETTYYNSALKSRLT
IIKDNSKSQVFLKMNSLQTDDTAIYYCAKHYYYGGSYAMDYWGQGTSVTVSSHM*ALSNSIMYFSHFVPVFL*
*PAKPTTTPAPRPPTPAPTIASQPLSLRPEACRPAAGGAVHTRGLD*IYIWAPLAGTCGVLLLSLVITKRGRK
KLLYIFKQPFMRPVQTTQEEDGCSCRFPEEEEGGCELPKLCYLLDGILFIYGVILTALFLRVKFSRSADAP
AYQQGQNQLYNELNLGRREEYDVLDKRRGRDPEMGGKPQRRKNPQEGLYNELQKDKMAEAYSEIGMKGERR
RGKGHDGLY

C.

<u>Signal sequence</u>

CD19 ScFv

*CD8 Hinge*

<u>Transmembrane domain</u>

```
                       SEQUENCE LISTING

<160> NUMBER OF SEQ ID NOS: 52

<210> SEQ ID NO 1
<211> LENGTH: 38
<212> TYPE: PRT
<213> ORGANISM: Artificial Sequence
<220> FEATURE:
<223> OTHER INFORMATION: Synthetic hook-binding domain

<400> SEQUENCE: 1

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 2
<211> LENGTH: 114
<212> TYPE: DNA
<213> ORGANISM: Artificial Sequence
<220> FEATURE:
<223> OTHER INFORMATION: Synthetic hook-binding domain

<400> SEQUENCE: 2
atggacgaga aaaccaccgg ctggcgggga ggccacgtgg tggaaggact ggccggcgag        60
ctggaacagc tgcgggccag actggaacac cacccccagg gccagagaga gccc            114

<210> SEQ ID NO 3
<211> LENGTH: 163
<212> TYPE: PRT
<213> ORGANISM: Homo sapiens

<400> SEQUENCE: 3

Lys Trp Lys Ala Leu Phe Thr Ala Ala Ile Leu Gln Ala Gln Leu Pro
1               5                   10                  15

Ile Thr Glu Ala Gln Ser Phe Gly Leu Leu Asp Pro Lys Leu Cys Tyr
```

```
                    20                  25                  30
Leu Leu Asp Gly Ile Leu Phe Ile Tyr Gly Val Ile Leu Thr Ala Leu
                35                  40                  45
Phe Leu Arg Val Lys Phe Ser Arg Ser Ala Asp Ala Pro Ala Tyr Gln
            50                  55                  60
Gln Gly Gln Asn Gln Leu Tyr Asn Glu Leu Asn Leu Gly Arg Arg Glu
 65                  70                  75                  80
Glu Tyr Asp Val Leu Asp Lys Arg Arg Gly Arg Asp Pro Glu Met Gly
                85                  90                  95
Gly Lys Pro Gln Arg Arg Lys Asn Pro Gln Glu Gly Leu Tyr Asn Glu
            100                 105                 110
Leu Gln Lys Asp Lys Met Ala Glu Ala Tyr Ser Glu Ile Gly Met Lys
            115                 120                 125
Gly Glu Arg Arg Arg Gly Lys Gly His Asp Gly Leu Tyr Gln Gly Leu
            130                 135                 140
Ser Thr Ala Thr Lys Asp Thr Tyr Asp Ala Leu His Met Gln Ala Leu
145                 150                 155                 160
Pro Pro Arg

<210> SEQ ID NO 4
<211> LENGTH: 220
<212> TYPE: PRT
<213> ORGANISM: Homo sapiens

<400> SEQUENCE: 4

Met Leu Arg Leu Leu Leu Ala Leu Asn Leu Phe Pro Ser Ile Gln Val
  1               5                   10                  15
Thr Gly Asn Lys Ile Leu Val Lys Gln Ser Pro Met Leu Val Ala Tyr
                20                  25                  30
Asp Asn Ala Val Asn Leu Ser Cys Lys Tyr Ser Tyr Asn Leu Phe Ser
                35                  40                  45
Arg Glu Phe Arg Ala Ser Leu His Lys Gly Leu Asp Ser Ala Val Glu
            50                  55                  60
Val Cys Val Val Tyr Gly Asn Tyr Ser Gln Gln Leu Gln Val Tyr Ser
 65                  70                  75                  80
Lys Thr Gly Phe Asn Cys Asp Gly Lys Leu Gly Asn Glu Ser Val Thr
                85                  90                  95
Phe Tyr Leu Gln Asn Leu Tyr Val Asn Gln Thr Asp Ile Tyr Phe Cys
            100                 105                 110
Lys Ile Glu Val Met Tyr Pro Pro Pro Tyr Leu Asp Asn Glu Lys Ser
            115                 120                 125
Asn Gly Thr Ile Ile His Val Lys Gly Lys His Leu Cys Pro Ser Pro
            130                 135                 140
Leu Phe Pro Gly Pro Ser Lys Pro Phe Trp Val Leu Val Val Val Gly
145                 150                 155                 160
Gly Val Leu Ala Cys Tyr Ser Leu Leu Val Thr Val Ala Phe Ile Ile
                165                 170                 175
Phe Trp Val Arg Ser Lys Arg Ser Arg Leu Leu His Ser Asp Tyr Met
                180                 185                 190
Asn Met Thr Pro Arg Arg Pro Gly Pro Thr Arg Lys His Tyr Gln Pro
            195                 200                 205
Tyr Ala Pro Pro Arg Asp Phe Ala Ala Tyr Arg Ser
        210                 215                 220
```

```
<210> SEQ ID NO 5
<211> LENGTH: 255
<212> TYPE: PRT
<213> ORGANISM: Homo sapiens

<400> SEQUENCE: 5

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 6
<211> LENGTH: 93
<212> TYPE: PRT
<213> ORGANISM: Homo sapiens

<400> SEQUENCE: 6

Met Ile His Leu Gly His Ile Leu Phe Leu Leu Leu Leu Pro Val Ala
1               5                   10                  15

Ala Ala Gln Thr Thr Pro Gly Glu Arg Ser Ser Leu Pro Ala Phe Tyr
            20                  25                  30

Pro Gly Thr Ser Gly Ser Cys Ser Gly Cys Gly Ser Leu Ser Leu Pro
        35                  40                  45

Leu Leu Ala Gly Leu Val Ala Ala Asp Ala Val Ala Ser Leu Leu Ile
    50                  55                  60

Val Gly Ala Val Phe Leu Cys Ala Arg Pro Arg Arg Ser Pro Ala Gln
65                  70                  75                  80

Glu Asp Gly Lys Val Tyr Ile Asn Met Pro Gly Arg Gly
```

<210> SEQ ID NO 7
<211> LENGTH: 277
<212> TYPE: PRT
<213> ORGANISM: Homo sapiens

<400> SEQUENCE: 7

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 8
<211> LENGTH: 199
<212> TYPE: PRT
<213> ORGANISM: Homo sapiens

<400> SEQUENCE: 8

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val

```
            35                  40                  45
Gln Gln Phe Lys Met Gln Leu Leu Lys Gly Gly Gln Ile Leu Cys Asp
 50                  55                  60

Leu Thr Lys Thr Lys Gly Ser Gly Asn Thr Val Ser Ile Lys Ser Leu
 65                  70                  75                  80

Lys Phe Cys His Ser Gln Leu Ser Asn Asn Ser Val Ser Phe Phe Leu
                 85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
            115                 120                 125

His Ile Tyr Glu Ser Gln Leu Cys Cys Gln Leu Lys Phe Trp Leu Pro
            130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
            195

<210> SEQ ID NO 9
<211> LENGTH: 220
<212> TYPE: DNA
<213> ORGANISM: Homo sapiens

<400> SEQUENCE: 9
attggggagt cccagccttg gggattcccc aactccgcag tttcttttct ccctctccca      60
acctatgtag ggtccttctt cctggatact cacgacgcgg acccagttct cactcccatt     120
gggtgtcggg tttccagaga agccaatcag tgtcgtcgcg gtcgcggttc taaagtccgc     180
acgcacccac cgggactcag attctcccca gacgccgagg                           220

<210> SEQ ID NO 10
<211> LENGTH: 197
<212> TYPE: DNA
<213> ORGANISM: Homo sapiens

<400> SEQUENCE: 10
ggggaggcgc agcgttgggg attcccccact cccctgagtt tcacttcttc tcccaacttg     60
tgtcgggtcc ttcttccagg atactcgtga cgcgtcccca cttcccactc ccattgggta    120
ttggatatct agagaagcca atcagcgtcg ccgcggtccc agttctaaag tccccacgca    180
cccacccgga ctcagag                                                    197

<210> SEQ ID NO 11
<211> LENGTH: 216
<212> TYPE: DNA
<213> ORGANISM: Homo sapiens

<400> SEQUENCE: 11
cactggggag gcgccgcgtt gaggattctc cactcccctc agtttcactt cttctcccaa     60
cctgcgtcgg gtccttcttc ctgaatactc atgacgcgtc cccaattccc actcccattg    120
ggtgtcgggt tctagagaag ccaatcagcg tctccgcagt cccggtctaa agtccccagt    180
cacccacccg gactcagatt ctccccagac gccgag                              216
```

<210> SEQ ID NO 12
<211> LENGTH: 205
<212> TYPE: DNA
<213> ORGANISM: Homo sapiens

<400> SEQUENCE: 12

```
taagaactgc tgattgctgg gaaactctgc agtttcccgt tcctctcgta acctggtcat    60
gtgtccttct tcctggatac tcatgacgca gactcagttc tcattcccaa tgggtgtcgg   120
gtttctagag aagccaatca gcgtcgccac gactcccgac tataaagtcc ccatccggac   180
tcaagaagtt ctcaggactc agagg                                         205
```

<210> SEQ ID NO 13
<211> LENGTH: 252
<212> TYPE: DNA
<213> ORGANISM: Homo sapiens

<400> SEQUENCE: 13

```
aggccccgag gcggtgtctg gggttggaag gctcagtatt gagaattccc catctcccca    60
gagtttctct ttctctccca acccgtgtca ggtccttcat cctggatact cataacgcgg   120
ccccatttct cactcccatt gggcgtcgcg tttctagaga agccaatcag tgtcgccgca   180
gttcccaggt tctaaagtcc cacgcacccc gcgggactca tattttccc agacgcggag    240
gttggggtca tg                                                       252
```

<210> SEQ ID NO 14
<211> LENGTH: 192
<212> TYPE: DNA
<213> ORGANISM: Homo sapiens

<400> SEQUENCE: 14

```
aacatcacga gactctaaga aaaggaaact gaaaacggga aagtccctct ctctaacctg    60
gcactgcgtc gctggcttgg agacaggtga cggtccctgc gggccttgtc ctgattggct   120
gggcacgcgt ttaatataag tggaggcgtc gcgctggcgg gcattcctga agctgacagc   180
attcgggccg ag                                                       192
```

<210> SEQ ID NO 15
<211> LENGTH: 33
<212> TYPE: DNA
<213> ORGANISM: Artificial Sequence
<220> FEATURE:
<223> OTHER INFORMATION: Synthetic PCR primer

<400> SEQUENCE: 15

```
cttactagtt ggaagggcta attcactccc aac                                 33
```

<210> SEQ ID NO 16
<211> LENGTH: 32
<212> TYPE: DNA
<213> ORGANISM: Artificial Sequence
<220> FEATURE:
<223> OTHER INFORMATION: Synthetic PCR primer

<400> SEQUENCE: 16

```
cattctagaa ctgctagaga ttttccacac tg                                  32
```

<210> SEQ ID NO 17
<211> LENGTH: 42
<212> TYPE: DNA

<210> SEQ ID NO 17
<211> LENGTH: 42
<212> TYPE: DNA
<213> ORGANISM: Artificial Sequence
<220> FEATURE:
<223> OTHER INFORMATION: Synthetic PCR primer

<400> SEQUENCE: 17
tacccngggc catggcctcc aaaaaagcct cctcactact tc          42

<210> SEQ ID NO 18
<211> LENGTH: 44
<212> TYPE: DNA
<213> ORGANISM: Artificial Sequence
<220> FEATURE:
<223> OTHER INFORMATION: Synthetic PCR primer

<400> SEQUENCE: 18
actcccgggt aatttttttt atttatgcag aggccgaggc cgcc        44

<210> SEQ ID NO 19
<211> LENGTH: 35
<212> TYPE: DNA
<213> ORGANISM: Artificial Sequence
<220> FEATURE:
<223> OTHER INFORMATION: Synthetic PCR primer

<400> SEQUENCE: 19
tacacgcgtg gagttccgcg ttacataact tacgg                  35

<210> SEQ ID NO 20
<211> LENGTH: 39
<212> TYPE: DNA
<213> ORGANISM: Artificial Sequence
<220> FEATURE:
<223> OTHER INFORMATION: Synthetic PCR primer

<400> SEQUENCE: 20
cgtggatccg atcgcggtgt cttctatgga ggtcaaaac              39

<210> SEQ ID NO 21
<211> LENGTH: 34
<212> TYPE: DNA
<213> ORGANISM: Artificial Sequence
<220> FEATURE:
<223> OTHER INFORMATION: Synthetic PCR primer

<400> SEQUENCE: 21
gccggcgcgc cgagaaaccc tgcagggaat tccc                   34

<210> SEQ ID NO 22
<211> LENGTH: 41
<212> TYPE: DNA
<213> ORGANISM: Artificial Sequence
<220> FEATURE:
<223> OTHER INFORMATION: Synthetic PCR primer

<400> SEQUENCE: 22
cgtggatccg atcgctcggc ccgaatgctg tcagcttcag g           41

<210> SEQ ID NO 23
<211> LENGTH: 517
<212> TYPE: DNA
<213> ORGANISM: Artificial Sequence
<220> FEATURE:
<223> OTHER INFORMATION: Synthetic Promoter

<400> SEQUENCE: 23
gagaaaccct gcagggaatt cccagctgt agttataaac agaagttctc cttctgctag    60

```
gtagcattca aagatcttaa tcttctgggt ttccgttttc tcgaatgaaa aatgcaggtc    120
cgagcagtta actggcgggg gcaccattag caagtcactt agcatctctg gggccagtct    180
gcaaagcgag ggggcagcct taatgtgcct ccagcctgaa gtcctagaat gagcgcccgg    240
tgtcccaagc tggggcgcgc accccagatc ggagggcgcc gatgtacaga cagcaaactc    300
acccagtcta gtgcatgcct tcttaaacat cacgagactc taagaaaagg aaactgaaaa    360
cgggaaagtc cctctctcta acctggcact gcgtcgctgg cttggagaca ggtgacggtc    420
cctgcgggcc ttgtcctgat tggctgggca cgcgtttaat ataagtggag cgtcgcgct    480 ggcgggcatt cctgaagctg acagcattcg ggccgag                             517
```

<210> SEQ ID NO 24
<211> LENGTH: 47
<212> TYPE: DNA
<213> ORGANISM: Artificial Sequence
<220> FEATURE:
<223> OTHER INFORMATION: Synthetic PCR primer

<400> SEQUENCE: 24

```
atgcatgcgt cgacctcgag ttaatcctca tcctgtctac ttgccac                   47
```

<210> SEQ ID NO 25
<211> LENGTH: 65
<212> TYPE: DNA
<213> ORGANISM: Artificial Sequence
<220> FEATURE:
<223> OTHER INFORMATION: Synthetic PCR primer

<400> SEQUENCE: 25

```
gcatgcatcg gccggggcgg cgactggtga gaggccacca tgggtgcgag agcgtcagta    60
ttaag                                                                 65
```

<210> SEQ ID NO 26
<211> LENGTH: 19
<212> TYPE: DNA
<213> ORGANISM: Artificial Sequence
<220> FEATURE:
<223> OTHER INFORMATION: Synthetic PCR primer

<400> SEQUENCE: 26

```
cccaagaacc caaggaaca                                                  19
```

<210> SEQ ID NO 27
<211> LENGTH: 25
<212> TYPE: DNA
<213> ORGANISM: Artificial Sequence
<220> FEATURE:
<223> OTHER INFORMATION: Synthetic PCR primer

<400> SEQUENCE: 27

```
agacaagata gaggaagagc aaaac                                           25
```

<210> SEQ ID NO 28
<211> LENGTH: 24
<212> TYPE: DNA
<213> ORGANISM: Artificial Sequence
<220> FEATURE:
<223> OTHER INFORMATION: Synthetic PCR primer

<400> SEQUENCE: 28

```
cggtgaggat cttcatgagg tagt                                            24
```

<210> SEQ ID NO 29
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 29
aacaccccag ccatgtacgt                                                 20

<210> SEQ ID NO 30
<211> LENGTH: 22
<212> TYPE: DNA
<213> ORGANISM: Artificial Sequence
<220> FEATURE:
<223> OTHER INFORMATION: Synthetic Probe

<400> SEQUENCE: 30
ccagccaggt ccagacgcag ga                                              22

<210> SEQ ID NO 31
<211> LENGTH: 160
<212> TYPE: PRT
<213> ORGANISM: Artificial Sequence
<220> FEATURE:
<223> OTHER INFORMATION: Synthetic Hook peptide

<400> SEQUENCE: 31

Met Asp Pro Ser Lys Asp Ser Lys Ala Gln Val Ser Ala Ala Glu Ala
1               5                   10                  15

Gly Ile Thr Gly Thr Trp Tyr Asn Gln Leu Gly Ser Thr Phe Ile Val
            20                  25                  30

Thr Ala Gly Ala Asp Gly Ala Leu Thr Gly Thr Tyr Glu Ser Ala Val
        35                  40                  45

Gly Asn Ala Glu Ser Arg Tyr Val Leu Thr Gly Arg Tyr Asp Ser Ala
    50                  55                  60

Pro Ala Thr Asp Gly Ser Gly Thr Ala Leu Gly Trp Thr Val Ala Trp
65                  70                  75                  80

Lys Asn Asn Tyr Arg Asn Ala His Ser Ala Thr Thr Trp Ser Gly Gln
                85                  90                  95

Tyr Val Gly Gly Ala Glu Ala Arg Ile Asn Thr Gln Trp Leu Leu Thr
            100                 105                 110

Ser Gly Thr Thr Glu Ala Asn Ala Trp Lys Ser Thr Leu Val Gly His
        115                 120                 125

Asp Thr Phe Thr Lys Val Lys Pro Ser Ala Ala Ser Ile Asp Ala Ala
    130                 135                 140

Lys Lys Ala Gly Val Asn Asn Gly Asn Pro Leu Asp Ala Val Gln Gln
145                 150                 155                 160

<210> SEQ ID NO 32
<211> LENGTH: 160
<212> TYPE: PRT
<213> ORGANISM: Artificial Sequence
<220> FEATURE:
<223> OTHER INFORMATION: Synthetic Hook peptide

<400> SEQUENCE: 32

Met Asp Pro Ser Lys Asp Ser Lys Ala Gln Val Ser Ala Ala Glu Ala
1               5                   10                  15

Gly Ile Thr Gly Thr Trp Tyr Asn Gln Leu Gly Ser Thr Phe Ile Val
            20                  25                  30

```
Thr Ala Gly Ala Asp Gly Ala Leu Thr Gly Thr Tyr Glu Ser Ala Val
        35                  40                  45

Gly Asn Ala Glu Ser Arg Tyr Thr Leu Thr Gly Arg Tyr Asp Ser Ala
    50                  55                  60

Pro Ala Thr Asp Gly Ser Gly Thr Ala Leu Gly Trp Arg Val Ala Trp
65                  70                  75                  80

Lys Asn Asn Tyr Arg Asn Ala His Ser Ala Thr Thr Trp Ser Gly Gln
                85                  90                  95

Tyr Val Gly Gly Ala Glu Ala Arg Ile Asn Thr Gln Trp Thr Leu Thr
            100                 105                 110

Ser Gly Thr Thr Glu Ala Asn Ala Trp Lys Ser Thr Leu Arg Gly His
        115                 120                 125

Asp Thr Phe Thr Lys Val Lys Pro Ser Ala Ala Ser Ile Asp Ala Ala
    130                 135                 140

Lys Lys Ala Gly Val Asn Asn Gly Asn Pro Leu Asp Ala Val Gln Gln
145                 150                 155                 160

<210> SEQ ID NO 33
<211> LENGTH: 260
<212> TYPE: PRT
<213> ORGANISM: Homo sapiens

<400> SEQUENCE: 33

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys His Tyr Ser Cys Pro Arg Glu Glu
225                 230                 235                 240

Glu Gly Ser Thr Ile Pro Ile Gln Glu Asp Tyr Arg Lys Pro Glu Pro
```

245        250        255

Ala Cys Ser Pro
         260

<210> SEQ ID NO 34
<211> LENGTH: 261
<212> TYPE: PRT
<213> ORGANISM: Homo sapiens

<400> SEQUENCE: 34

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 35
<211> LENGTH: 1224
<212> TYPE: DNA
<213> ORGANISM: Artificial Sequence
<220> FEATURE:
<223> OTHER INFORMATION: Synthetic Hook sequence

<400> SEQUENCE: 35
atgcaccgga ggagatcacg ctcttgtagg gaggaccaga aacctgtcac cggtgaccct    60
agcaaagact caaaagctca ggtgtccgct gccgaggctg gcattactgg aacatggtac   120
aatcagctcg ggagcacctt tattgtgact gctggagccg atggagccct caccggaaca   180

```
tacgaatctg ctgtgggaaa cgccgaatca cggtacgtcc tcactggccg atacgatagt    240 gccccctgcca ccgacggatc tgggactgcc ctgggatgga ctgtcgcttg aaaaacaac     300 taccggaatg ctcattctgc cacaacatgg agtggacagt acgtgggagg cgctgaggct    360
agaatcaata cacagtggct gctcacatct ggcacaaccg aggcaaatgc ttggaaatcc    420
accctggtgg gacatgacac attcaccaaa gtgaaccct ccgccgcttc aatcgatgcc     480
gccaaaaaag ccggagtcaa caacggcaat cctctggatg ccgtccagca ggtcgactat    540
ccgtacgacg taccagacta cgcagtcgga ccgatggacg atcagaggga cctcattagc    600
aacaacgaac agctgcctat gctgggacgg cgacctggag cccctgaatc caaatgctct    660
aggggagcac tgtacactgg cttctccatt ctcgtgacac tgctgctggc cgggcaggct    720
actactgctt acttcctgta ccagcagcag gggcggctgg acaaactcac tgtgacatct    780
cagaacctcc agctggaaaa tctgaggatg aaactgccca acccccctaa accgtgtcc     840 aaaatgagga tggccacacc tctgctcatg caggcactgc caatgggagc cctgccccag    900
gggcccatgc agaatgccac caagtatggc aacatgacag aggaccatgt gatgcacctg    960
ctccagaatg ctgaccccct gaaggtgtac ccgccactga aggggagctt cccggagaac   1020
ctgagacacc ttaagaacac catggagacc atagactgga aggtctttga gagctggatg   1080
caccattggc tcctgtttga aatgagcagg cactccttgg agcaaaagcc cactgacgct   1140
ccaccgaaag agtcactgga actggaggac ccgtcttctg ggctgggtgt gaccaagcag   1200
gatctgggcc cagtccccat gtga                                           1224

<210> SEQ ID NO 36
<211> LENGTH: 477
<212> TYPE: DNA
<213> ORGANISM: Artificial Sequence
<220> FEATURE:
<223> OTHER INFORMATION: Synthetic Hook sequence

<400> SEQUENCE: 36
gaccctagca aagactcaaa agctcaggtg tccgctgccg aggctggcat tactggaaca     60
tggtacaatc agctcgggag cacctttatt gtgactgctg gagccgatgg agccctcacc    120
ggaacatacg aatctgctgt gggaaacgcc gaatcacggt acgtcctcac tggccgatac    180
gatagtgccc ctgccaccga cggatctggg actgccctgg gatggactgt cgcttggaaa    240
aacaactacc ggaatgctca ttctgccaca acatggagtg gacagtacgt gggaggcgct    300
gaggctagaa tcaatacaca gtggctgctc acatctggca caaccgaggc aaatgcttgg    360
aaatccaccc tggtgggaca tgacacattc accaaagtga aaccctccgc cgcttcaatc    420
gatgccgcca aaaagccgg agtcaacaac ggcaatcctc tggatgccgt ccagcag        477

<210> SEQ ID NO 37
<211> LENGTH: 27
<212> TYPE: DNA
<213> ORGANISM: Artificial Sequence
<220> FEATURE:
<223> OTHER INFORMATION: Synthetic HA TAG

<400> SEQUENCE: 37
tatccgtacg acgtaccaga ctacgca                                         27

<210> SEQ ID NO 38
<211> LENGTH: 1216
<212> TYPE: DNA
```

<213> ORGANISM: Homo sapiens

<400> SEQUENCE: 38

| | | | | | |
|---|---|---|---|---|---|
| ggcctccgcg | ccgggttttg | ggcctcccgc | gggcgccccc | ctcctcacgg | cgagcgctgc | 60 |
| cacgtcagac | gaagggcgca | gcgagcgtcc | tgatccttcc | gcccgacgc | tcaggacagc | 120 |
| ggcccgctgc | tcataagact | cggccttaga | accccagtat | cagcagaagg | acattttagg | 180 |
| acgggacttg | ggtgactcta | gggcactggt | tttctttcca | gagagcggaa | caggcgagga | 240 |
| aaagtagtcc | cttctcggcg | attctgcgga | gggatctccg | tggggcggtg | aacgccgatg | 300 |
| attatataag | gacgcgccgg | gtgtggcaca | gctagttccg | tcgcagccgg | gatttgggtc | 360 |
| gcggttcttg | tttgtggatc | gctgtgatcg | tcacttggtg | agtagcgggc | tgctgggctg | 420 |
| gccggggctt | tcgtggccgc | cgggccgctc | ggtgggacgg | aagcgtgtgg | agagaccgcc | 480 |
| aagggctgta | gtctgggtcc | gcgagcaagg | ttgccctgaa | ctgggggttg | ggggagcgc | 540 |
| agcaaaatgg | cggctgttcc | cgagtcttga | atggaagacg | cttgtgaggc | gggctgtgag | 600 |
| gtcgttgaaa | caaggtgggg | ggcatggtgg | gcggcaagaa | cccaaggtct | tgaggccttc | 660 |
| gctaatgcgg | gaaagctctt | attcgggtga | gatgggctgg | ggcaccatct | ggggaccctg | 720 |
| acgtgaagtt | tgtcactgac | tggagaactc | ggtttgtcgt | ctgttgcggg | ggcggcagtt | 780 |
| atggcggtgc | cgttgggcag | tgcacccgta | cctttgggag | cgcgcgccct | cgtcgtgtcg | 840 |
| tgacgtcacc | cgttctgttg | gcttataatg | cagggtgggg | ccacctgccg | gtaggtgtgc | 900 |
| ggtaggcttt | tctccgtcgc | aggacgcagg | gttcgggcct | agggtaggct | ctcctgaatc | 960 |
| gacaggcgcc | ggacctctgg | tgaggggagg | gataagtgag | gcgtcagttt | ctttggtcgg | 1020 |
| ttttatgtac | ctatcttctt | aagtagctga | agctccggtt | ttgaactatg | cgctcggggt | 1080 |
| tggcgagtgt | gttttgtgaa | gttttttagg | caccttttga | aatgtaatca | tttgggtcaa | 1140 |
| tatgtaattt | tcagtgttag | actagtaaat | tgtccgctaa | attctggccg | tttttggctt | 1200 |
| ttttgttaga | ccgatc | | | | | 1216 |

<210> SEQ ID NO 39
<211> LENGTH: 1518
<212> TYPE: DNA
<213> ORGANISM: Artificial Sequence
<220> FEATURE:
<223> OTHER INFORMATION: Synthetic CAR

<400> SEQUENCE: 39

| | | | | | |
|---|---|---|---|---|---|
| atggccctgc | ctgtgacagc | cctgctgctg | cccctggctc | tcctgctgca | tgccgccaga | 60 |
| cccgctagcg | acatccagat | gacccagacc | accagcagcc | tgagcgccag | cctgggcgac | 120 |
| agagtgacca | tcagctgccg | ggccagccag | gacatcagca | agtacctgaa | ctggtatcag | 180 |
| cagaaacccg | acggcaccgt | gaagctgctg | atctaccaca | ccagccggct | ccacagcggc | 240 |
| gtgcccagca | gattttctgg | cagcggcagc | ggcaccgact | acagcctgac | catctccaac | 300 |
| ctggaacagg | aagatatcgc | tacctacttc | tgtcagcaag | gcaacaccct | gccctacacc | 360 |
| ttcggcggag | gcaccaagct | ggaaatcacc | ggcggaggcg | gaagtggagg | tggaggatct | 420 |
| ggcggcggag | gctccgaagt | gaagctgcag | gaaagcggcc | ctggcctcgt | ggcccctagc | 480 |
| cagagcctgt | ccgtgacctg | taccgtgtcc | ggcgtgtccc | tgcccgacta | cggcgtgtcc | 540 |
| tggatcagac | agcctcccag | aaagggcctg | aatggctgg | gcgtgatctg | ggcagcgag | 600 |
| acaacctact | acaacagcgc | cctgaagtcc | cggctgacca | tcatcaagga | caacagcaag | 660 |
| agccaggtgt | tcctgaagat | gaacagcctg | cagaccgacg | acaccgccat | ctactactgc | 720 |

```
gccaagcact actactacgg cggcagctac gccatggact actggggcca gggcaccagc    780
gtgaccgtgt ccagccatat ggccctgagc aacagcatca tgtacttcag ccacttcgtg    840
cccgtgtttc tgcccgccaa gcccaccacc acccctgccc ctagacctcc cacccccagcc   900 ccaacaatcg ccagccagcc tctgtccctg cggcccgaag cctgtagacc tgctgccggc    960
ggagccgtgc acaccagagg cctggatatc tacatctggg cccctctggc cggcacctgt   1020
ggcgtgctgc tgctgagcct ggtgatcaca agcggggca gaaagaagct gctgtacatc    1080
ttcaagcagc cattcatgcg gcccgtgcag accacccagg aagaggacgg ctgcagctgc   1140
cggttccccg aggaagagga aggcggctgc gaactgccca gctgtgcta cctgctggac    1200 ggcatcctgt tcatctatgg cgtgatcctg accgccctgt tcctgagagt gaagttcagc   1260
agaagcgccg acgcccctgc ctaccagcag ggccagaacc agctgtacaa cgagctgaac   1320
ctgggcagac gggaagagta cgacgtgctg gacaagcgga gaggccggga ccctgagatg   1380
ggcggcaagc cccagcggcg gaagaaccct caggaaggcc tgtataacga actgcagaaa   1440
gacaagatgg ccgaggccta cagcgagatc ggcatgaagg gcgagcggcg gagaggcaag   1500
ggccacgatg gcctgtac                                                 1518

<210> SEQ ID NO 40
<211> LENGTH: 1641
<212> TYPE: DNA
<213> ORGANISM: Artificial Sequence
<220> FEATURE:
<223> OTHER INFORMATION: Synthetic CAR

<400> SEQUENCE: 40
atggccctgc ctgtgacagc cctgctgctg cccctcgctc tgctgctgca tgccgccaga     60
cccgctagcg acatccagat gacccagacc accagcagcc tgagcgccag cctgggcgac    120
agagtgacca tcagctgccg ggccagccag gacatcagca gtacctgaa ctggtatcag    180 cagaaacccg acggcaccgt gaagctgctg atctaccaca ccagccggct ccacagcggc    240
gtgcccagca gatttttctgg cagcggcagc ggcaccgact acagcctgac catctccaac    300
ctggaacagg aagatatcgc tacctacttc tgtcagcaag caacaccct gccctacacc    360 ttcggcggag gcaccaagct ggaaatcacc ggcggaggcg aagtggaggg ggaggatct    420 ggcggcggag gctccgaagt gaagctgcag gaaagcggcc ctggcctggt ggcccctagc    480
cagagcctgt ccgtgacctg taccgtgtcc ggcgtgtccc tgcccgacta cggcgtgtcc    540
tggatcagac agccccccag aaagggcctg aatggctggc gcgtgatctg gggcagcgag    600
acaacctact acaacagcgc cctgaagtcc cggctgacca tcatcaagga caacagcaag    660
agccaggtgt tcctgaagat gaacagcctg cagaccgacg acaccgccat ctactactgc    720
gccaagcact actactacgg cggcagctac gccatggact actggggcca gggcaccagc    780
gtgaccgtgt ccagccatat ggccctgagc aacagcatca tgtacttcag ccacttcgtg    840
cccgtgtttc tgcccgccaa gcccaccacc acccctgccc ctagacctcc cacccccagcc   900 ccaacaatcg ccagccagcc tctgtccctg aggcccgaag cctgtagacc tgctgccggc    960
ggagccgtgc acaccagagg cctggatatc tacatctggg cccctctggc cggcacctgt   1020
ggcgtgctgc tgctgagcct ggtgatcacc cggtccaagc ggagcagact gctgcactcc   1080
gactacatga acatgacccc cagacggcct ggcccacccc ggaagcacta ccagccttac   1140
gcccctcccc gggacttcgc cgcctacaga agcaagcggg gcagaaagaa gctgctgtac   1200
```

```
atcttcaagc agcccttcat gcggcccgtg cagaccaccc aggaagagga cggctgcagc    1260
tgccggttcc ccgaggaaga ggaaggcggc tgcgaactgc ccaagctgtg ctacctgctg    1320
gacggcatcc tgttcatcta tggcgtgatc ctgaccgccc tgttcctgag agtgaagttc    1380
agcagaagcg ccgacgcccc tgcctaccag cagggccaga accagctgta caacgagctg    1440
aacctgggca gacgggaaga gtacgacgtg ctggacaagc gcagaggccg ggaccctgag    1500
atgggcggca gcctcagcg gcggaagaac cctcaggaag gcctgtataa cgaactgcag    1560
aaagacaaga tggccgaggc ctacagcgag atcggcatga agggcgagcg gcggagaggc    1620
aagggccacg atggcctgta c                                              1641
```

<210> SEQ ID NO 41
<211> LENGTH: 300
<212> TYPE: DNA
<213> ORGANISM: Homo sapiens

<400> SEQUENCE: 41

```
gtctagaagt cagattgggg ttaaagagtc tgtccgtgat tgactaacag tcttaaatac      60
ttgatttgtt gttgttgttg tcctgtttgt ttaagaactt tacttcttta tccaatgaac     120
ggagtatctt gtgtcctgga cccttttgcaa gaacccttcc cctagcaaca gatgcgtcat    180
ctcaaaatat ttttctgatt ggccaaagag taattgattt gcattttaat ggtcagactc    240
tattacaccc cacattctct tttcttttat tcttgtctgt tctgcctcac tcccgagctc    300
```

<210> SEQ ID NO 42
<211> LENGTH: 407
<212> TYPE: PRT
<213> ORGANISM: Artificial Sequence
<220> FEATURE:
<223> OTHER INFORMATION: Synthetic Hook peptide

<400> SEQUENCE: 42

Met His Arg Arg Arg Ser Arg Ser Cys Arg Glu Asp Gln Lys Pro Val
1               5                   10                  15

Thr Gly Asp Pro Ser Lys Asp Ser Lys Ala Gln Val Ser Ala Ala Glu
            20                  25                  30

Ala Gly Ile Thr Gly Thr Trp Tyr Asn Gln Leu Gly Ser Thr Phe Ile
        35                  40                  45

Val Thr Ala Gly Ala Asp Gly Ala Leu Thr Gly Thr Tyr Glu Ser Ala
    50                  55                  60

Val Gly Asn Ala Glu Ser Arg Tyr Val Leu Thr Gly Arg Tyr Asp Ser
65                  70                  75                  80

Ala Pro Ala Thr Asp Gly Ser Gly Thr Ala Leu Gly Trp Thr Val Ala
                85                  90                  95

Trp Lys Asn Asn Tyr Arg Asn Ala His Ser Ala Thr Thr Trp Ser Gly
            100                 105                 110

Gln Tyr Val Gly Gly Ala Glu Ala Arg Ile Asn Thr Gln Trp Leu Leu
        115                 120                 125

Thr Ser Gly Thr Thr Glu Ala Asn Ala Trp Lys Ser Thr Leu Val Gly
    130                 135                 140

His Asp Thr Phe Thr Lys Val Lys Pro Ser Ala Ala Ser Ile Asp Ala
145                 150                 155                 160

Ala Lys Lys Ala Gly Val Asn Asn Gly Asn Pro Leu Asp Ala Val Gln
                165                 170                 175

Gln Val Asp Tyr Pro Tyr Asp Val Pro Asp Tyr Ala Val Gly Pro Met
            180                 185                 190
```

```
Asp Asp Gln Arg Asp Leu Ile Ser Asn Asn Glu Gln Leu Pro Met Leu
        195                 200                 205

Gly Arg Arg Pro Gly Ala Pro Glu Ser Lys Cys Ser Arg Gly Ala Leu
    210                 215                 220

Tyr Thr Gly Phe Ser Ile Leu Val Thr Leu Leu Leu Ala Gly Gln Ala
225                 230                 235                 240

Thr Thr Ala Tyr Phe Leu Tyr Gln Gln Gln Gly Arg Leu Asp Lys Leu
                245                 250                 255

Thr Val Thr Ser Gln Asn Leu Gln Leu Glu Asn Leu Arg Met Lys Leu
            260                 265                 270

Pro Lys Pro Pro Lys Pro Val Ser Lys Met Arg Met Ala Thr Pro Leu
        275                 280                 285

Leu Met Gln Ala Leu Pro Met Gly Ala Leu Pro Gln Gly Pro Met Gln
    290                 295                 300

Asn Ala Thr Lys Tyr Gly Asn Met Thr Glu Asp His Val Met His Leu
305                 310                 315                 320

Leu Gln Asn Ala Asp Pro Leu Lys Val Tyr Pro Pro Leu Lys Gly Ser
                325                 330                 335

Phe Pro Glu Asn Leu Arg His Leu Lys Asn Thr Met Glu Thr Ile Asp
            340                 345                 350

Trp Lys Val Phe Glu Ser Trp Met His His Trp Leu Leu Phe Glu Met
        355                 360                 365

Ser Arg His Ser Leu Glu Gln Lys Pro Thr Asp Ala Pro Pro Lys Glu
    370                 375                 380

Ser Leu Glu Leu Glu Asp Pro Ser Ser Gly Leu Gly Val Thr Lys Gln
385                 390                 395                 400

Asp Leu Gly Pro Val Pro Met
                405

<210> SEQ ID NO 43
<211> LENGTH: 1224
<212> TYPE: DNA
<213> ORGANISM: Artificial Sequence
<220> FEATURE:
<223> OTHER INFORMATION: Synthetic Hook sequence

<400> SEQUENCE: 43
atgcaccgga ggagatcacg ctcttgtagg gaggaccaga aacctgtcac cggtgaccct      60
agcaaagact caaaagctca ggtgtccgct gccgaggctg gcattactgg aacatggtac     120
aatcagctcg ggagcacctt tattgtgact gctggagccg atggagccct caccggaaca     180
tacgaatctg ctgtgggaaa cgccgaatca cggtacgtcc tcactggccg atacgatagt     240
gcccctgcca ccgacggatc tgggactgcc tgggatgga ctgtcgcttg gaaaaacaac     300
taccggaatg ctcattctgc cacaacatgg agtggacagt acgtgggagg cgctgaggct     360
agaatcaata cacagtggct gctcacatct ggcacaaccg aggcaaatgc ttggaaatcc     420
accctggtgg acatgacac attcaccaaa gtgaaccct cgccgcttc aatcgatgcc      480 gccaaaaaag ccggagtcaa caacggcaat cctctggatg ccgtccagca ggtcgactat     540
ccgtacgacg taccagacta cgcagtcgga ccgatgacg atcagaggga cctcattagc      600
aacaacgaac agctgcctat gctgggacgg cgacctggag ccctgaatc caaatgctct     660 aggggagcac tgtacactgg cttctccatt ctcgtgacac tgctgctggc cgggcaggct     720
actactgctt acttcctgta ccagcagcag gggcggctgg acaaactcac tgtgacatct     780
```

| | |
|---|---|
| cagaacctcc agctggaaaa tctgaggatg aaactgccca aaccccctaa acccgtgtcc | 840 |
| aaaatgagga tggccacacc tctgctcatg caggcactgc caatgggagc cctgccccag | 900 |
| gggcccatgc agaatgccac caagtatggc aacatgacag aggaccatgt gatgcacctg | 960 |
| ctccagaatg ctgaccccct gaaggtgtac ccgccactga aggggagctt cccggagaac | 1020 |
| ctgagacacc ttaagaacac catggagacc atagactgga aggtctttga gagctggatg | 1080 |
| caccattggc tcctgtttga aatgagcagg cactccttgg agcaaaagcc cactgacgct | 1140 |
| ccaccgaaag agtcactgga actggaggac ccgtcttctg ggctgggtgt gaccaagcag | 1200 |
| gatctgggcc cagtccccat gtga | 1224 |

<210> SEQ ID NO 44
<211> LENGTH: 574
<212> TYPE: DNA
<213> ORGANISM: Artificial Sequence
<220> FEATURE:
<223> OTHER INFORMATION: Synthetic IRES

<400> SEQUENCE: 44

| | |
|---|---|
| gcccctctcc ctcccccccc cctaacgtta ctggccgaag ccgcttggaa taaggccggt | 60 |
| gtgcgtttgt ctatatgtta ttttccacca tattgccgtc ttttggcaat gtgagggccc | 120 |
| ggaaacctgg ccctgtcttc ttgacgagca ttcctagggg tctttcccct ctcgccaaag | 180 |
| gaatgcaagg tctgttgaat gtcgtgaagg aagcagttcc tctggaagct tcttgaagac | 240 |
| aaacaacgtc tgtagcgacc ctttgcaggc agcggaaccc cccacctggc gacaggtgcc | 300 |
| tctgcggcca aaagccacgt gtataagata cacctgcaaa ggcggcacaa ccccagtgcc | 360 |
| acgttgtgag ttggatagtt gtggaaagag tcaaatggct ctcctcaagc gtattcaaca | 420 |
| aggggctgaa ggatgcccag aaggtacgcc attgtatggg atctgatctg gggcctcggt | 480 |
| gcacatgctt tacatgtgtt tagtcgaggt taaaaaacgt ctaggccccc cgaaccacgg | 540 |
| ggacgtggtt ttcctttgaa aaacacgatg ataa | 574 |

<210> SEQ ID NO 45
<211> LENGTH: 1638
<212> TYPE: DNA
<213> ORGANISM: Artificial Sequence
<220> FEATURE:
<223> OTHER INFORMATION: Synthetic CAR

<400> SEQUENCE: 45

| | |
|---|---|
| atggccctgc ctgtgacagc cctgctgctg cccctggctc tcctgctgca tgccgccaga | 60 |
| cccgctagcg acatccagat gacccagacc accagcagcc tgagcgccag cctgggcgac | 120 |
| agagtgacca tcagctgccg ggccagccag gacatcagca gtacctgaa ctggtatcag | 180 |
| cagaaacccg acggcaccgt gaagctgctg atctaccaca ccagccggct ccacagcggc | 240 |
| gtgcccagca gattttctgg cagcggcagc ggcaccgact acagcctgac catctccaac | 300 |
| ctggaacagg aagatatcgc tacctacttc tgtcagcaag caacaccct gcctacacc | 360 |
| ttcggcggag gcaccaagct ggaaatcacc ggcggaggcg aagtggagg tggaggatct | 420 |
| ggcggcggag gctccgaagt gaagctgcag gaaagcggcc ctggcctcgt ggcccctagc | 480 |
| cagagcctgt ccgtgacctg taccgtgtcc ggcgtgtccc tgcccgacta cggcgtgtcc | 540 |
| tggatcagac agcctcccag aaagggcctg aatggctgg cgtgatctg gggcagcgag | 600 |
| acaacctact acaacagcgc cctgaagtcc cggctgacca tcatcaagga caacagcaag | 660 |
| agccaggtgt tcctgaagat gaacagcctg cagaccgacg acaccgccat ctactactgc | 720 |

```
gccaagcact actactacgg cggcagctac gccatggact actggggcca gggcaccagc    780
gtgaccgtgt ccagccatat ggccctgagc aacagcatca tgtacttcag ccacttcgtg    840
cccgtgtttc tgcccgccaa gcccaccacc acccctgccc ctagacctcc cacccccagcc   900 ccaacaatcg ccagccagcc tctgtccctg cggcccgaag cctgtagacc tgctgccggc    960
ggagccgtgc acaccagagg cctggatatc tacatctggg cccctctggc cggcacctgt   1020
ggcgtgctgc tgctgagcct ggtgatcacc accggtatgg acgagaaaac caccggctgg   1080
cggggaggcc acgtggtgga aggactggcc ggcgagctgg aacagctgcg gccagactg    1140 gaacaccacc cccagggcca gagagagccc aagcggggca gaaagaagct gctgtacatc   1200
ttcaagcagc ccttcatgcg gcccgtgcag accacccagg aagaggacgg ctgcagctgc   1260
cggttccccg aggaagagga aggcggctgc gaactgccca agctgtgcta cctgctggac   1320
ggcatcctgt tcatctacgg cgtgatcctg accgccctgt tcctgagagt gaagttcagc   1380
agaagcgccg acgcccctgc ctaccagcag ggccagaacc agctgtacaa cgagctgaac   1440
ctgggcagac gggaagagta cgacgtgctg gacaagcgga gaggccggga ccctgagatg   1500
ggcggcaagc cccagcggcg gaagaacccc caggaaggcc tgtataacga actgcagaaa   1560
gacaagatgg ccgaggccta cagcgagatc ggcatgaagg gcgagcggcg agaggcaag   1620 ggccacgatg gcctgtac                                                 1638

<210> SEQ ID NO 46
<211> LENGTH: 546
<212> TYPE: PRT
<213> ORGANISM: Artificial Sequence
<220> FEATURE:
<223> OTHER INFORMATION: Synthetic CAR

<400> SEQUENCE: 46

Met Ala Leu Pro Val Thr Ala Leu Leu Leu Pro Leu Ala Leu Leu Leu
1               5                   10                  15

His Ala Ala Arg Pro Ala Ser Asp Ile Gln Met Thr Gln Thr Thr Ser
                20                  25                  30

Ser Leu Ser Ala Ser Leu Gly Asp Arg Val Thr Ile Ser Cys Arg Ala
            35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
                100                 105                 110

Gln Gly Asn Thr Leu Pro Tyr Thr Phe Gly Gly Gly Thr Lys Leu Glu
            115                 120                 125

Ile Thr Gly Gly Gly Gly Ser Gly Gly Gly Gly Ser Gly Gly Gly Gly
    130                 135                 140

Ser Glu Val Lys Leu Gln Glu Ser Gly Pro Gly Leu Val Ala Pro Ser
145                 150                 155                 160

Gln Ser Leu Ser Val Thr Cys Thr Val Ser Gly Val Ser Leu Pro Asp
                165                 170                 175

Tyr Gly Val Ser Trp Ile Arg Gln Pro Pro Arg Lys Gly Leu Glu Trp
                180                 185                 190
```

Leu Gly Val Ile Trp Gly Ser Glu Thr Thr Tyr Tyr Asn Ser Ala Leu
            195                 200                 205

Lys Ser Arg Leu Thr Ile Ile Lys Asp Asn Ser Lys Ser Gln Val Phe
210                 215                 220

Leu Lys Met Asn Ser Leu Gln Thr Asp Thr Ala Ile Tyr Tyr Cys
225                 230                 235                 240

Ala Lys His Tyr Tyr Tyr Gly Gly Ser Tyr Ala Met Asp Tyr Trp Gly
            245                 250                 255

Gln Gly Thr Ser Val Thr Val Ser Ser His Met Ala Leu Ser Asn Ser
            260                 265                 270

Ile Met Tyr Phe Ser His Phe Val Pro Val Phe Leu Pro Ala Lys Pro
            275                 280                 285

Thr Thr Thr Pro Ala Pro Arg Pro Pro Thr Pro Ala Pro Thr Ile Ala
290                 295                 300

Ser Gln Pro Leu Ser Leu Arg Pro Glu Ala Cys Arg Pro Ala Ala Gly
305                 310                 315                 320

Gly Ala Val His Thr Arg Gly Leu Asp Ile Tyr Ile Trp Ala Pro Leu
            325                 330                 335

Ala Gly Thr Cys Gly Val Leu Leu Leu Ser Leu Val Ile Thr Thr Gly
            340                 345                 350

Met Asp Glu Lys Thr Thr Gly Trp Arg Gly Gly His Val Val Glu Gly
            355                 360                 365

Leu Ala Gly Glu Leu Glu Gln Leu Arg Ala Arg Leu Glu His His Pro
            370                 375                 380

Gln Gly Gln Arg Glu Pro Lys Arg Gly Arg Lys Lys Leu Leu Tyr Ile
385                 390                 395                 400

Phe Lys Gln Pro Phe Met Arg Pro Val Gln Thr Thr Gln Glu Glu Asp
            405                 410                 415

Gly Cys Ser Cys Arg Phe Pro Glu Glu Glu Glu Gly Cys Glu Leu
            420                 425                 430

Pro Lys Leu Cys Tyr Leu Leu Asp Gly Ile Leu Phe Ile Tyr Gly Val
            435                 440                 445

Ile Leu Thr Ala Leu Phe Leu Arg Val Lys Phe Ser Arg Ser Ala Asp
450                 455                 460

Ala Pro Ala Tyr Gln Gln Gly Gln Asn Gln Leu Tyr Asn Glu Leu Asn
465                 470                 475                 480

Leu Gly Arg Arg Glu Glu Tyr Asp Val Leu Asp Lys Arg Arg Gly Arg
            485                 490                 495

Asp Pro Glu Met Gly Gly Lys Pro Gln Arg Arg Lys Asn Pro Gln Glu
            500                 505                 510

Gly Leu Tyr Asn Glu Leu Gln Lys Asp Lys Met Ala Glu Ala Tyr Ser
            515                 520                 525

Glu Ile Gly Met Lys Gly Glu Arg Arg Arg Gly Lys Gly His Asp Gly
            530                 535                 540

Leu Tyr
545

<210> SEQ ID NO 47
<211> LENGTH: 1638
<212> TYPE: DNA
<213> ORGANISM: Artificial Sequence
<220> FEATURE:
<223> OTHER INFORMATION: Synthetic CAR

<400> SEQUENCE: 47

| | |
|---|---|
| atggccctgc ctgtgacagc cctgctgctg cccctggctc tcctgctgca tgccgccaga | 60 |
| cccgctagcg acatccagat gacccagacc accagcagcc tgagcgccag cctgggcgac | 120 |
| agagtgacca tcagctgccg ggccagccag gacatcagca agtacctgaa ctggtatcag | 180 |
| cagaaacccg acggcaccgt gaagctgctg atctaccaca ccagccggct ccacagcggc | 240 |
| gtgcccagca gatttctctgg cagcggcagc ggcaccgact acagcctgac catctccaac | 300 |
| ctggaacagg aagatatcgc tacctacttc tgtcagcaag caacacccct gccctacacc | 360 |
| ttcggcggag gcaccaagct ggaaatcacc ggcggaggcg aagtggaggt ggaggatct | 420 |
| ggcggcggag gctccgaagt gaagctgcag gaaagcggcc ctggcctcgt ggcccctagc | 480 |
| cagagcctgt ccgtgacctg taccgtgtcc ggcgtgtccc tgcccgacta cggcgtgtcc | 540 |
| tggatcagac agcctcccag aaagggcctg aatggctggc gcgtgatctg gggcagcgag | 600 |
| acaacctact acaacagcgc cctgaagtcc cggctgacca tcatcaagga caacagcaag | 660 |
| agccaggtgt tcctgaagat gaacagcctg cagaccgacg acaccgccat ctactactgc | 720 |
| gccaagcact actactacgg cggcagctac gccatggact actggggcca gggcaccagc | 780 |
| gtgaccgtgt ccagccatat ggccctgagc aacagcatca tgtacttcag ccacttcgtg | 840 |
| cccgtgtttc tgcccgccaa gcccaccacc cccctgccc ctagacctcc caccccagcc | 900 |
| ccaacaatcg ccagccagcc tctgtccctg cggcccgaag cctgtagacc tgctgccggc | 960 |
| ggagccgtgc acaccagagg cctggatatc tacatctggg ccctctggc cggcacctgt | 1020 |
| ggcgtgctgc tgctgagcct ggtgatcaca aagcggggca gaaagaagct gctgtacatc | 1080 |
| ttcaagcagc ccttcatgcg cccgtgcag accacccagg aagaggacgg ctgcagctgc | 1140 |
| cggttccccg aggaagagga aggcggctgc gagctgaccg gtatggacga aaaaccacc | 1200 |
| ggctggcggg gaggccacgt ggtggaagga ctggccggcg agctgaaca gctgcgggcc | 1260 |
| agactggaac accacccca gggccagagg gaaccccca gctgtgcta cctgctggac | 1320 |
| ggcatcctgt tcatctacgg cgtgatcctg accgccctgt tcctgagagt gaagttcagc | 1380 |
| agaagcgccg acgcccctgc ctaccagcag ggccagaacc agctgtacaa cgagctgaac | 1440 |
| ctgggcagac gggaagagta cgacgtgctg gacaagcgga gaggccggga ccctgagatg | 1500 |
| ggcggcaagc cccagcggcg gaagaacccc caggaaggcc tgtataacga actgcagaaa | 1560 |
| gacaagatgg ccgaggccta cagcgagatc ggcatgaagg gcgagcggcg gagaggcaag | 1620 |
| ggccacgatg gcctgtac | 1638 |

<210> SEQ ID NO 48
<211> LENGTH: 546
<212> TYPE: PRT
<213> ORGANISM: Artificial Sequence
<220> FEATURE:
<223> OTHER INFORMATION: Synthetic CAR

<400> SEQUENCE: 48

Met Ala Leu Pro Val Thr Ala Leu Leu Leu Pro Leu Ala Leu Leu Leu
1               5                   10                  15

His Ala Ala Arg Pro Ala Ser Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly

-continued

```
            65                  70                  75                  80
Val Pro Ser Arg Phe Ser Gly Ser Gly Ser Gly Thr Asp Tyr Ser Leu
                    85                  90                  95

Thr Ile Ser Asn Leu Glu Gln Glu Asp Ile Ala Thr Tyr Phe Cys Gln
                100                 105                 110

Gln Gly Asn Thr Leu Pro Tyr Thr Phe Gly Gly Gly Thr Lys Leu Glu
                115                 120                 125

Ile Thr Gly Gly Gly Gly Ser Gly Gly Gly Gly Ser Gly Gly Gly Gly
            130                 135                 140

Ser Glu Val Lys Leu Gln Glu Ser Gly Pro Gly Leu Val Ala Pro Ser
145                 150                 155                 160

Gln Ser Leu Ser Val Thr Cys Thr Val Ser Gly Val Ser Leu Pro Asp
                165                 170                 175

Tyr Gly Val Ser Trp Ile Arg Gln Pro Pro Arg Lys Gly Leu Glu Trp
            180                 185                 190

Leu Gly Val Ile Trp Gly Ser Glu Thr Thr Tyr Tyr Asn Ser Ala Leu
                195                 200                 205

Lys Ser Arg Leu Thr Ile Ile Lys Asp Asn Ser Lys Ser Gln Val Phe
        210                 215                 220

Leu Lys Met Asn Ser Leu Gln Thr Asp Asp Thr Ala Ile Tyr Tyr Cys
225                 230                 235                 240

Ala Lys His Tyr Tyr Tyr Gly Gly Ser Tyr Ala Met Asp Tyr Trp Gly
                245                 250                 255

Gln Gly Thr Ser Val Thr Val Ser Ser His Met Ala Leu Ser Asn Ser
                260                 265                 270

Ile Met Tyr Phe Ser His Phe Val Pro Val Phe Leu Pro Ala Lys Pro
        275                 280                 285

Thr Thr Thr Pro Ala Pro Arg Pro Pro Thr Pro Ala Pro Thr Ile Ala
            290                 295                 300

Ser Gln Pro Leu Ser Leu Arg Pro Glu Ala Cys Arg Pro Ala Ala Gly
305                 310                 315                 320

Gly Ala Val His Thr Arg Gly Leu Asp Ile Tyr Ile Trp Ala Pro Leu
                325                 330                 335

Ala Gly Thr Cys Gly Val Leu Leu Leu Ser Leu Val Ile Thr Lys Arg
            340                 345                 350

Gly Arg Lys Lys Leu Leu Tyr Ile Phe Lys Gln Pro Phe Met Arg Pro
        355                 360                 365

Val Gln Thr Thr Gln Glu Glu Asp Gly Cys Ser Cys Arg Phe Pro Glu
        370                 375                 380

Glu Glu Glu Gly Gly Cys Glu Leu Thr Gly Met Asp Glu Lys Thr Thr
385                 390                 395                 400

Gly Trp Arg Gly Gly His Val Val Glu Gly Leu Ala Gly Glu Leu Glu
                405                 410                 415

Gln Leu Arg Ala Arg Leu Glu His His Pro Gln Gly Gln Arg Glu Pro
            420                 425                 430

Pro Lys Leu Cys Tyr Leu Leu Asp Gly Ile Leu Phe Ile Tyr Gly Val
        435                 440                 445

Ile Leu Thr Ala Leu Phe Leu Arg Val Lys Phe Ser Arg Ser Ala Asp
        450                 455                 460

Ala Pro Ala Tyr Gln Gln Gly Gln Asn Gln Leu Tyr Asn Glu Leu Asn
465                 470                 475                 480

Leu Gly Arg Arg Glu Glu Tyr Asp Val Leu Asp Lys Arg Arg Gly Arg
                485                 490                 495
```

Asp Pro Glu Met Gly Gly Lys Pro Gln Arg Arg Lys Asn Pro Gln Glu
        500                 505                 510
Gly Leu Tyr Asn Glu Leu Gln Lys Asp Lys Met Ala Glu Ala Tyr Ser
    515                 520                 525
Glu Ile Gly Met Lys Gly Glu Arg Arg Arg Gly Lys Gly His Asp Gly
530                 535                 540
Leu Tyr
545

<210> SEQ ID NO 49
<211> LENGTH: 1638
<212> TYPE: DNA
<213> ORGANISM: Artificial Sequence
<220> FEATURE:
<223> OTHER INFORMATION: Synthetic CAR

<400> SEQUENCE: 49

| | | | | | | |
|---|---|---|---|---|---|---|
| atggccctgc | ctgtgacagc | cctgctgctg | cccctggctc | tcctgctgca | tgccgccaga | 60 |
| cccgctagcg | acatccagat | gacccagacc | accagcagcc | tgagcgccag | cctgggcgac | 120 |
| agagtgacca | tcagctgccg | ggccagccag | gacatcagca | agtacctgaa | ctggtatcag | 180 |
| cagaaacccg | acggcaccgt | gaagctgctg | atctaccaca | ccagccggct | ccacagcggc | 240 |
| gtgcccagca | gattttctgg | cagcggcagc | ggcaccgact | acagcctgac | catctccaac | 300 |
| ctggaacagg | aagatatcgc | tacctacttc | tgtcagcaag | caacaccct | gcctacacc | 360 |
| ttcggcggag | gcaccaagct | ggaaatcacc | ggcggaggcg | aagtggagg | tggaggatct | 420 |
| ggcggcggag | gctccgaagt | gaagctgcag | gaaagcggcc | ctggcctcgt | ggcccctagc | 480 |
| cagagcctgt | ccgtgacctg | taccgtgtcc | ggcgtgtccc | tgcccgacta | cggcgtgtcc | 540 |
| tggatcagac | agcctcccag | aaagggcctg | gaatggctgg | gcgtgatctg | gggcagcgag | 600 |
| acaacctact | acaacagcgc | cctgaagtcc | cggctgacca | tcatcaagga | caacagcaag | 660 |
| agccaggtgt | tcctgaagat | gaacagcctg | cagaccgacg | acaccgccat | ctactactgc | 720 |
| gccaagcact | actactacgg | cggcagctac | gccatggact | actggggcca | gggcaccagc | 780 |
| gtgaccgtgt | ccagccatat | ggccctgagc | aacagcatca | tgtacttcag | ccacttcgtg | 840 |
| cccgtgtttc | tgcccgccaa | gcccaccacc | acccctgccc | ctagacctcc | caccccagcc | 900 |
| ccaacaatcg | ccagccagcc | tctgtccctg | cggcccgaag | cctgtagacc | tgctgccggc | 960 |
| ggagccgtgc | acaccagagg | cctggatatc | tacatctggg | cccctctggc | cggcacctgt | 1020 |
| ggcgtgctgc | tgctgagcct | ggtgatcaca | aagcggggca | gaaagaagct | gctgtacatc | 1080 |
| ttcaagcagc | ccttcatgcg | gcccgtgcag | accacccagg | aagaggacgg | ctgcagctgc | 1140 |
| cggttccccg | aggaagagga | aggcggctgc | gaactgccca | gctgtgctac | ctgctggac | 1200 |
| ggcatcctgt | tcatctacgg | cgtgatcctg | accgccctgt | tcctgagagt | gaagttcagc | 1260 |
| agaagcgccg | acgccctgc | ctaccagcag | ggccagaacc | agctgtacaa | cgagctgaac | 1320 |
| ctgggcagac | gggaagagta | cgacgtgctg | gacaagcgga | gaggccggga | ccctgagatg | 1380 |
| ggcggcaagc | cccagcggcg | gaagaacccc | caggaaggcc | tgtataacga | actgcagaaa | 1440 |
| gacaagatgg | ccgaggccta | cagcgagatc | ggcatgaagg | gcgagcggcg | agaggcaag | 1500 |
| ggccacgatg | gcctgtacac | cggtatggac | gagaaaacca | ccggctggcg | gggaggccac | 1560 |
| gtggtggaag | gactgccggg | cgagctggaa | cagctgcggg | ccagactgga | acaccacccc | 1620 |
| cagggccaga | gggaaccc | | | | | 1638 |

```
<210> SEQ ID NO 50
<211> LENGTH: 546
<212> TYPE: PRT
<213> ORGANISM: Artificial Sequence
<220> FEATURE:
<223> OTHER INFORMATION: Synthetic CAR

<400> SEQUENCE: 50

Met Ala Leu Pro Val Thr Ala Leu Leu Leu Pro Leu Ala Leu Leu Leu
1               5                   10                  15

His Ala Ala Arg Pro Ala Ser Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
            100                 105                 110

Gln Gly Asn Thr Leu Pro Tyr Thr Phe Gly Gly Gly Thr Lys Leu Glu
        115                 120                 125

Ile Thr Gly Gly Gly Gly Ser Gly Gly Gly Gly Ser Gly Gly Gly Gly
    130                 135                 140

Ser Glu Val Lys Leu Gln Glu Ser Gly Pro Gly Leu Val Ala Pro Ser
145                 150                 155                 160

Gln Ser Leu Ser Val Thr Cys Thr Val Ser Gly Val Ser Leu Pro Asp
                165                 170                 175

Tyr Gly Val Ser Trp Ile Arg Gln Pro Pro Arg Lys Gly Leu Glu Trp
            180                 185                 190

Leu Gly Val Ile Trp Gly Ser Glu Thr Thr Tyr Tyr Asn Ser Ala Leu
        195                 200                 205

Lys Ser Arg Leu Thr Ile Ile Lys Asp Asn Ser Lys Ser Gln Val Phe
    210                 215                 220

Leu Lys Met Asn Ser Leu Gln Thr Asp Asp Thr Ala Ile Tyr Tyr Cys
225                 230                 235                 240

Ala Lys His Tyr Tyr Tyr Gly Gly Ser Tyr Ala Met Asp Tyr Trp Gly
                245                 250                 255

Gln Gly Thr Ser Val Thr Val Ser Ser His Met Ala Leu Ser Asn Ser
            260                 265                 270

Ile Met Tyr Phe Ser His Phe Val Pro Val Phe Leu Pro Ala Lys Pro
        275                 280                 285

Thr Thr Thr Pro Ala Pro Arg Pro Pro Thr Pro Ala Pro Thr Ile Ala
    290                 295                 300

Ser Gln Pro Leu Ser Leu Arg Pro Glu Ala Cys Arg Pro Ala Ala Gly
305                 310                 315                 320

Gly Ala Val His Thr Arg Gly Leu Asp Ile Tyr Ile Trp Ala Pro Leu
                325                 330                 335

Ala Gly Thr Cys Gly Val Leu Leu Leu Ser Leu Val Ile Thr Lys Arg
            340                 345                 350

Gly Arg Lys Lys Leu Leu Tyr Ile Phe Lys Gln Pro Phe Met Arg Pro
        355                 360                 365
```

-continued

Val Gln Thr Thr Gln Glu Glu Asp Gly Cys Ser Cys Arg Phe Pro Glu
370                 375                 380

Glu Glu Glu Gly Gly Cys Glu Leu Pro Lys Leu Cys Tyr Leu Leu Asp
385                 390                 395                 400

Gly Ile Leu Phe Ile Tyr Gly Val Ile Leu Thr Ala Leu Phe Leu Arg
                405                 410                 415

Val Lys Phe Ser Arg Ser Ala Asp Ala Pro Ala Tyr Gln Gln Gly Gln
            420                 425                 430

Asn Gln Leu Tyr Asn Glu Leu Asn Leu Gly Arg Arg Glu Glu Tyr Asp
        435                 440                 445

Val Leu Asp Lys Arg Arg Gly Arg Asp Pro Glu Met Gly Gly Lys Pro
450                 455                 460

Gln Arg Arg Lys Asn Pro Gln Glu Gly Leu Tyr Asn Glu Leu Gln Lys
465                 470                 475                 480

Asp Lys Met Ala Glu Ala Tyr Ser Glu Ile Gly Met Lys Gly Glu Arg
                485                 490                 495

Arg Arg Gly Lys Gly His Asp Gly Leu Tyr Thr Gly Met Asp Glu Lys
            500                 505                 510

Thr Thr Gly Trp Arg Gly Gly His Val Val Glu Gly Leu Ala Gly Glu
        515                 520                 525

Leu Glu Gln Leu Arg Ala Arg Leu Glu His His Pro Gln Gly Gln Arg
530                 535                 540

Glu Pro
545

<210> SEQ ID NO 51
<211> LENGTH: 506
<212> TYPE: PRT
<213> ORGANISM: Artificial Sequence
<220> FEATURE:
<223> OTHER INFORMATION: Synthetic CAR

<400> SEQUENCE: 51

Met Ala Leu Pro Val Thr Ala Leu Leu Leu Pro Leu Ala Leu Leu Leu
1               5                   10                  15

His Ala Ala Arg Pro Ala Ser Asp Ile Gln Met Thr Gln Thr Thr Ser
                20                  25                  30

Ser Leu Ser Ala Ser Leu Gly Asp Arg Val Thr Ile Ser Cys Arg Ala
            35                  40                  45

Ser Gln Asp Ile Ser Lys Tyr Leu Asn Trp Tyr Gln Gln Lys Pro Asp
        50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
            100                 105                 110

Gln Gly Asn Thr Leu Pro Tyr Thr Phe Gly Gly Gly Thr Lys Leu Glu
        115                 120                 125

Ile Thr Gly Gly Gly Gly Ser Gly Gly Gly Gly Ser Gly Gly Gly Gly
130                 135                 140

Ser Glu Val Lys Leu Gln Glu Ser Gly Pro Gly Leu Val Ala Pro Ser
145                 150                 155                 160

Gln Ser Leu Ser Val Thr Cys Thr Val Ser Gly Val Ser Leu Pro Asp
                165                 170                 175

```
Tyr Gly Val Ser Trp Ile Arg Gln Pro Pro Arg Lys Gly Leu Glu Trp
            180                 185                 190

Leu Gly Val Ile Trp Gly Ser Glu Thr Thr Tyr Tyr Asn Ser Ala Leu
            195                 200                 205

Lys Ser Arg Leu Thr Ile Ile Lys Asp Asn Ser Lys Ser Gln Val Phe
            210                 215                 220

Leu Lys Met Asn Ser Leu Gln Thr Asp Thr Ala Ile Tyr Tyr Cys
225                 230                 235                 240

Ala Lys His Tyr Tyr Tyr Gly Ser Tyr Ala Met Asp Tyr Trp Gly
            245                 250                 255

Gln Gly Thr Ser Val Thr Val Ser Ser His Met Ala Leu Ser Asn Ser
            260                 265                 270

Ile Met Tyr Phe Ser His Phe Val Pro Val Phe Leu Pro Ala Lys Pro
            275                 280                 285

Thr Thr Thr Pro Ala Pro Arg Pro Pro Thr Pro Ala Pro Thr Ile Ala
            290                 295                 300

Ser Gln Pro Leu Ser Leu Arg Pro Glu Ala Cys Arg Pro Ala Ala Gly
305                 310                 315                 320

Gly Ala Val His Thr Arg Gly Leu Asp Ile Tyr Ile Trp Ala Pro Leu
            325                 330                 335

Ala Gly Thr Cys Gly Val Leu Leu Leu Ser Leu Val Ile Thr Lys Arg
            340                 345                 350

Gly Arg Lys Lys Leu Leu Tyr Ile Phe Lys Gln Pro Phe Met Arg Pro
            355                 360                 365

Val Gln Thr Thr Gln Glu Glu Asp Gly Cys Ser Cys Arg Phe Pro Glu
            370                 375                 380

Glu Glu Glu Gly Gly Cys Glu Leu Pro Lys Leu Cys Tyr Leu Leu Asp
385                 390                 395                 400

Gly Ile Leu Phe Ile Tyr Gly Val Ile Leu Thr Ala Leu Phe Leu Arg
            405                 410                 415

Val Lys Phe Ser Arg Ser Ala Asp Ala Pro Ala Tyr Gln Gln Gly Gln
            420                 425                 430

Asn Gln Leu Tyr Asn Glu Leu Asn Leu Gly Arg Arg Glu Glu Tyr Asp
            435                 440                 445

Val Leu Asp Lys Arg Arg Gly Arg Asp Pro Glu Met Gly Gly Lys Pro
            450                 455                 460

Gln Arg Arg Lys Asn Pro Gln Glu Gly Leu Tyr Asn Glu Leu Gln Lys
465                 470                 475                 480

Asp Lys Met Ala Glu Ala Tyr Ser Glu Ile Gly Met Lys Gly Glu Arg
            485                 490                 495

Arg Arg Gly Lys Gly His Asp Gly Leu Tyr
            500                 505

<210> SEQ ID NO 52
<211> LENGTH: 27
<212> TYPE: DNA
<213> ORGANISM: Artificial Sequence
<220> FEATURE:
<223> OTHER INFORMATION: Synthetic Probe

<400> SEQUENCE: 52
aaccattagg agtagcaccc accaagg                                          27
```

LENTIVIRAL VECTORS FOR REGULATED EXPRESSION OF A CHIMERIC ANTIGEN RECEPTOR MOLECULE

TECHNICAL FIELD

The present invention is in the field of recombinant vaccine technology and relates to improvements of lentiviral vectors, which can be used as therapeutic and prophylactic vaccines. The vectors provide improved induction of immune responses over other vectors.

BACKGROUND

Recombinant vaccines have been developed with the progress of recombinant DNA technology, allowing the modification of viral genomes to produce modified viruses. In this manner, it has been possible to introduce genetic sequences into non-pathogenic viruses, so that they encode immunogenic proteins to be expressed in target cells upon infection or transduction, in order to develop a specific immune response in their host.

Such vaccines constitute a major advance in vaccine technology (Kutzler et al., Nat Rev Genet, 9(10): 776-788, 2008). In particular, they have the advantage over traditional vaccines of avoiding live (attenuated) virus and eliminating risks associated with the manufacture of inactivated vaccines.

Gene delivery using modified retroviruses (retroviral vectors) was introduced in the early 1980s by Mann et al. (Cell, 33(1):153-9, 1983). The most commonly used oncogenic retroviral vectors are based on the Moloney murine leukemia virus (MLV). They have a simple genome from which the polyproteins Gag, Pol and Env are produced and are required in trans for viral replication (Breckpot et al., 2007, Gene Ther, 14(11):847-62; He et al. 2007, Expert Rev vaccines, 6(6):913-24). Sequences generally required in cis are the long terminal repeats (LTRs) and its vicinity: the inverted repeats (IR or att sites) required for integration, the packaging sequence P, the transport RNA-binding site (primer binding site, PBS), and some additional sequences involved in reverse transcription (the repeat R within the LTRs, and the polypurine tracts, PPT, necessary for plus strand initiation). To generate replication-defective retroviral vectors, the gag, pol, and env genes are generally entirely deleted and replaced with an expression cassette.

Retroviral vectors deriving from lentivirus genomes (i.e. lentiviral vectors) have emerged as promising tools for both gene therapy and immunotherapy purposes, because they exhibit several advantages over other viral systems. In particular, lentiviral vectors themselves are not toxic and, unlike other retroviruses, lentiviruses are capable of transducing non-dividing cells, in particular dendritic cells (He et al. 2007, Expert Rev vaccines, 6(6):913-24), allowing antigen presentation through the endogenous pathway.

Lentiviruses are linked by similarities in genetic composition, molecular mechanisms of replication and biological interactions with their hosts. They are best known as agents of slow disease syndromes that begin insidiously after prolonged periods of subclinical infection and progress slowly; thus, they are referred to as the "slow" viruses (Narayan et al., 1989, J Gen Virol, 70(7):1617-39). They have the same basic organization as all retroviruses but are more complex due to the presence of accessory genes (e.g., vif, vpr, vpu, nef, tat, and rev), which play key roles in lentiviral replication in vivo.

Lentiviruses represent a genus of slow viruses of the Retroviridae family, which includes the human immunodeficiency viruses (HIV), the simian immunodeficiency virus (SIV), the equine infectious encephalitis virus (EIAV), the caprine arthritis encephalitis virus (CAEV), the bovine immunodeficiency virus (BIV), and the feline immunodeficiency virus (FIV). Lentiviruses can persist indefinitely in their hosts and replicate continuously at variable rates during the course of the lifelong infection. Persistent replication of the viruses in their hosts depends on their ability to circumvent host defenses.

The design of recombinant integrating lentiviral vectors is based on the separation of the cis- and trans-acting sequences of the lentivirus. Efficient transduction in non-dividing cells requires the presence of two cis-acting sequences in the lentiviral genome, the central polypurine tract (cPPT) and the central termination sequence (CTS). These lead to the formation of a triple-stranded DNA structure called the central DNA "flap", which maximizes the efficiency of gene import into the nuclei of non-dividing cells, including dendritic cells (DCs) (Zennou et al., 2000, Cell, 101(2) 173-85; Arhel et al., 2007, EMBO J, 26(12): 3025-37).

Dendritic cells are of primary importance for antigen presentation because they constitute the main class of antigen presenting cells (APCs) whose primary function is to present antigens and initiate an immune response.

To generate an immune response, antigenic proteins must be processed by cells into peptides that are displayed on the cell surface by major histocompatibility complex proteins (MHCs). Circulating APCs present the peptide-MHC complexes to T cells in the draining lymph nodes, where they interact with T cell receptors, and, in conjunction with co-stimulatory signals, activate the T cells.

A variety of studies have shown that inoculation with lentiviral vectors leads to antigen presentation by DCs and strong activation of antigen specific cytotoxic T lymphocytes (CTLs; CD8[+] T cells). Therefore, lentiviral vectors have been engineered for the last 10 years for gene transfer and immunotherapy applications.

The vectors routinely contain strong constitutive promoters containing enhancers, such as the CMV promoter. Michelini et al., Vaccine 27(34):4622-29 (2009); Karwacz et al., J. Virol. 83(7):30943103 (2009); Negri et al., Molecular Therapy 15(9):1716-23 (2007); and Buffa et al., J. General Virology 87:1625-1634 (2006).

Lentiviral vectors have been improved in their safety by removal of the LTR U3 sequence, resulting in "self-inactivating" vectors that are entirely devoid of viral promoter and enhancer sequences originally present within the LTRs.

The lentiviral particles, which contain lentiviral vectors, can be produced by recombinant technology upon transient transfection of cells, for example HEK 293T human cultured cells, by different DNA plasmids:

(i) a packaging plasmid, which expresses at least the Gag, Pol Rev, Tat and, in some cases, structural and enzymatic proteins necessary for the packaging of the transfer construct;

(ii) a proviral transfer plasmid, containing an expression cassette and HIV cis-acting factors necessary for packaging, reverse transcription, and integration; and (iii) an envelope-encoding plasmid, in most cases the glycoprotein of vesicular stomatitis virus (VSV.G), a protein that allows the formation of mixed particles (pseudotypes) that can target a wide variety of cells, especially major histocompatibility (MHC) antigen-presenting cells (APCs), including DCs.

This procedure allows obtaining transient production of lentiviral particle vectors by the transfected cells. However, the lentiviral particle vectors may also be continuously produced by cells by stably inserting the packaging genes, the proviral coding DNA, and the envelope gene into the cellular genome. This allows the continuous production of lentiviral particle vectors by the cells without the need for transient transfection. Of course, a combination of these procedures can be used, with some of the DNAs/plasmids integrated into the cellular genome and others provided by transient transfection.

Non-integrating lentiviral vectors have been designed to mitigate the risks of potential oncogenesis linked to insertional mutagenesis events, particularly for vaccination purposes. Examples of non-integrating lentiviral vectors are provided in Coutant et al., PLOS ONE 7(11):e48644 (2102), Karwacz et al., J. Virol. 83(7):3094-3103 (2009), Negri et al., Molecular Therapy 15(9):1716-1723 (2007); Hu et al., Vaccine 28:6675-6683 (2010). Consequently, it has been reported that a non-integrating lentiviral vector system can mitigate the potential risk of insertional mutagenesis as compared to an integrating system. Hu et al., Vaccine 28:6675-6683 (2010).

In addition, deletion in the U3 region of the 3' LTR of the viral promoter and enhancer sequences in self-inactivating lentiviral vectors limits the likelihood of endogenous promoter activation. These concerns with safety directly address the experiences gained from the SCID-X1 gene therapy trial carried out in 1998-1999, performed with Moloney virus-based retroviral vectors on children suffering from a rare form of X-linked (SCID-X1 gene) severe immunodeficiency disease (Cavazzana-Calvo et al., 2000, Science., 288(5466):669-72). During this trial, four of nine children developed leukemia as a result of the integration of the Moloney-derived retroviral vector at close proximity to the human LM02 proto-oncogene (Hacein-Bey-Abina et al., 2008, J. Clin. Invest., 118(9):3132-3142). It was demonstrated that malignancy was the consequence of the proximity of the viral U3 promoter/enhancer to the LM02 proto-oncogene. As a result, safety is a major concern for the administration of lentivectors to humans.

Enhancers are cis-acting sequences, which can act as transcriptional activators at a distance. They have been widely employed in viral derived vectors because they appear to be the most efficient for obtaining transgene strong expression in a variety of cell types, in particular DCs (Chinnasamy et al., 2000, Hum Gene Ther 11(13):1901-9; Rouas et al., 2008, Cancer Gene Ther 9(9):715-24; Kimura et al., 2007, Mol Ther 15(7):1390-9; Gruh et al., 2008, J Gene Med 10(1) 21-32). However, given the safety issue of insertional mutagenesis, such transcriptional enhancer sequences should be deleted from the lentiviral vector constructs to abolish the risk of insertional mutagenesis by enhancer proximity effect. This enhancer proximity effect is by far the most frequent mechanism of insertional mutagenesis and is the only effect described in human or animal cases of tumorigenic events after gene transfer.

Thus, there is a need to develop retroviral, particularly lentiviral vectors, which do not include viral enhancers, but still allow sufficient expression of transgenes encoding immunogenic peptides, if possible, as much expression as that observed when using the CMV promoter.

Recent studies has reported on the replacement of viral promoters by DC-specific promoters deriving from major histocompatibility complex class II genes (MHC class II) (Kimura et al., 2007, Mol Ther 15(7):1390-9) and dectin-2 genes (Lopes et al., 2008, J Virol 82(1):86-95). The dectin-2 gene promoter used in Lopes et al. contains a putative enhancer and an adenoviral conserved sequence (inverted terminal repeats in adenovirus promoter) (Bonkabara et al., 2001, J. Immunology, 167:6893-6900). The MHC class II gene promoter used by Kimura et al. does not contain any known enhancer.

Yet, without an enhancer, the MHC class II promoter was found not to provide sufficient transgene expression in DCs, when administered intravenously. In particular, lentiviral vectors including MHC class II promoters did not provoke an immune reaction in immunocompetent C57BL/6 mice, in contrast to the immune responses observed with CMV promoters/enhancers. Although integration and persistent transgene expression were observed after injection in mice, the lentiviral vectors transcribed through MHC class II promoters failed to stimulate an antigen-specific CD8+ cytotoxic T-lymphocyte response, even after vaccination boost. The authors of these studies therefore concluded that the use of MHC class II promoters was of interest only for applications where persistence of expression is sought as in gene replacement therapy, but not in the context of immunotherapy. Of note, MHC class II promoters are expressed poorly in most cell types.

Thus, the MHC class II promoter is not an adequate promoter for lentiviral vectors for induction of an immune response against an antigen via IV injection. Moreover, the dectin-2 promoter is expressed poorly in most cell types and appears to contain an enhancer. Thus, the dectin-2 promoter is not a good promoter for lentiviral vectors for safety reasons.

Preferably, in immunotherapy, lentiviral vectors provide effective expression of the transgene that elicits a desired specific immune response. This requires that the expression is at a high level in APCs, such as dendritic cells.

It is also preferable that the cells transduced by the lentiviral vectors are eliminated by the immune response to provide a higher degree of safety. That is, the immune response generated against the transgene can elicit an immune response in the host sufficient to eliminate the cells that are transduced by the lentiviral vectors. The elimination of transduced cells eliminates the persistence of the lentiviral vector in the host, and possible secondary effects of the vector. In order for the transduced cells to be eliminated, expression is required in non-dendritic cells at a level that allows elimination by the immune response. Thus, appropriate expression of an antigen is desirable.

At the same time, the promoter should maximize immune stimulation through the key cells (i.e., dendritic cells) involved in the activation of naïve and memory T cells, and should minimize the risk of insertional mutagenesis and genotoxicity in stem cells, leading to malignancies. Thus, the promoter should have sufficiently high activity in dendritic and other cells, but not contain an enhancer. Based on these criteria, viral promoters, such as the CMV promoter, are not ideal because of the presence of strong enhancers. These criteria are summarized as follows:

high expression in antigen presenting cells, including dendritic cells, to induce maximal immune responses;

expression in other transduced cell types sufficient for elimination by the induced immune response; and lack of an enhancer element to avoid insertional effects.

Chimeric antigen receptors (CARs) are recombinant receptors for antigens. Sadelain et al., Cancer Discov. 2013 April; 3(4): 388-398. They are recombinant receptors that typically target native cell surface antigens. Id. CARs engage molecules that do not require peptide processing or HLA expression to be recognized. Id. CARs have been shown to have T cell-proliferating and activating potential on their own, including chimeric molecules between CD3-ζ or Fc receptor γ and CD8, CD4, CD25 or CD16. The antigen-binding parts of the CARs generally are either scFv's derived from antibodies, Fab's selected from libraries, or natural receptor ligands. Han E Q et al.; J Hematol Oncol, 6:47, 2013.

CARs have been generated against many different cell surface molecules, including CD19, HER2, GD2, PSMA, and many are in clinical trials. Davila et al., OncoImmunology 1:9, 1577-1583; 2012. The most promising clinical outcomes of CARs have been in patients treated with autologous CAR-modified T cells targeting CD19. Maus M V et al.; 123(17): 2625-35, 2014.

The in vivo elimination of T cells expressing CARs has been investigated. Human T cells have been genetically modified with a lentiviral vector to express a CD20-CAR containing a suicide gene relying on inducible activation of caspase 9. Budde et al., PLoS ONE 8(12): e82742 (2013). This lentivector used the human EF1α promoter to obtain expression in T cells. Activation of the suicide fuse resulted in efficient removal of transduced T cells both in vitro and in vivo. Id.

It would be better to be able quickly turn off the expression of the CAR at the surface of the cells to prevent adverse events and be able reactivate the system after it has been turned off. Thus, a need exists in the art for improved vectors and methods for treatment of humans. The present invention fulfills these needs in the art.

SUMMARY OF THE INVENTION

The invention encompasses nucleic acid molecules and vectors encoding CARs and methods of making and using the nucleic acid molecules and vectors. In one embodiment, the invention encompasses a chimeric antigen receptor comprising a binding domain; a transmembrane domain; a hook-binding domain, preferably comprising a streptavidin-binding peptide; and an activation domain comprising a T cell activating fragment of at least 100 amino acids of SEQ ID NO:3; SEQ ID NO:4; SEQ ID NO:5; SEQ ID NO:6, SEQ ID NO:7, or SEQ ID NO:8, SEQ ID NO:33, or SEQ ID NO:34.

In one embodiment, the invention encompasses a lentiviral vector expressing a chimeric antigen receptor comprising a binding domain; a transmembrane domain; a hook-binding domain comprising a streptavidin-binding peptide; and an activation domain comprising a T cell activating fragment of at least 100 amino acids of SEQ ID NO:3; SEQ ID NO:4; SEQ ID NO:5; SEQ ID NO:6, SEQ ID NO:7, or SEQ ID NO:8, SEQ ID NO:33, or SEQ ID NO:34.

In one embodiment, the invention encompasses a nucleic acid vector encoding a chimeric antigen receptor comprising a binding domain; a transmembrane domain; a hook-binding domain, preferably comprising a streptavidin-binding peptide; and an activation domain comprising a T cell activating fragment of at least 100 amino acids of SEQ ID NO:3; SEQ ID NO:4; SEQ ID NO:5; SEQ ID NO:6, SEQ ID NO:7, or SEQ ID NO:8, SEQ ID NO:33, or SEQ ID NO:34.

In one embodiment, invention encompasses a lentiviral vector particle encoding a chimeric antigen receptor comprising a binding domain; a transmembrane domain; a hook-binding domain, preferably comprising a streptavidin-binding peptide; and an activation domain comprising a T cell activating fragment of at least 100 amino acids of SEQ ID NO:3; SEQ ID NO:4; SEQ ID NO:5; SEQ ID NO:6, SEQ ID NO:7, or SEQ ID NO:8, SEQ ID NO:33, or SEQ ID NO:34.

In one embodiment, the chimeric antigen receptor or the lentiviral vector or the nucleic acid vector or the lentiviral vector particle comprises a single-chain Fv antibody or a single-domain antibodies (i.e., nanobody).

In one embodiment, the vector encodes a hook comprising the amino acid sequence of SEQ ID NO:31 or SEQ ID NO:32.

In one embodiment, the vector comprises a β2-microglobulin, Ubi, EF1α, MHCI, or MHCII promoter. In one embodiment, the vector is a DNA.

In one embodiment, the lentiviral vector particle comprises a vesicular stomatitis virus glycoprotein. In one embodiment, the lentiviral vector particle comprises HIV-1 subtype D Gag and Pol proteins.

In one embodiment, the invention encompasses an isolated cell comprising a vector of the invention.

The invention encompasses the use of the chimeric antigen receptor or the lentiviral vector or the nucleic acid vector or the lentiviral vector particle of any of the invention for inducing an immune response in a human.

The invention encompasses a method for inducing an immune response in a human comprising administering the lentiviral vector particle or cells transduced by the lentiviral vector particle encoding a chimeric antigen receptor to a human and, optionally, subsequently administering biotin to the human.

In some embodiments, the chimeric antigen receptor or the lentiviral vector or the nucleic acid vector comprises the nucleotide sequence of any of SEQ ID NO:45, SEQ ID NO:47, or SEQ ID NO:49. In some embodiments, the chimeric antigen receptor receptor comprises the amino acid sequence of any of SEQ ID NO:46, SEQ ID NO:48, or SEQ ID NO:50.

In some embodiments, the lentiviral vector or the nucleic acid vector further encodes the amino acid sequence of SEQ ID NO:42 or comprises the nucleic acid sequence of SEQ ID NO:43 and/or SEQ ID NO:44.

BRIEF DESCRIPTION OF THE DRAWINGS

FIG. 2 depicts cell-specific expression of various promoters analyzed using the data sets at biogps.org. The expression levels were normalized to expression in skeletal muscle (=1.0).

FIG. 3A-C depict expression of a CAR in T cells from various lentivectors with human ubiquitin, MHC class I, MHC class II, and β2 microglobulin (β2m) promoters.

FIG. 5A-B depict structure and expression of CAR-RUSH. A) Scheme of the three CAR-RUSH constructions designed. CAR-RUSH are second generation CARs displaying 4-1BB and CD3zeta intracellular domains. The peculiarity of CAR-RUSH resides in the presence of a SBP (Streptavidin Binding Protein) region allowing the interaction with a HOOK protein coupled to streptavidin and, consequently, the retention in the endoplasmic reticulum. The difference between SBP1, SBP2 and SBP3 consists in the position of the SBP region, which has been placed between the transmembrane domain and 4-1BB, or between 4-1BB and CD3zeta, or at the C-terminus, respectively. B) MFI showing median fluorescence intensity of CAR-positive T lymphocytes analysed by FACS. Cells were transduced at a MOI of 10 and analysed at day 3 post-transduction. MFI values reported in the histogram are normalized by substracting the mfi from untransduced cells, corresponding to the background. All CAR-positive T cells showed comparable MFI, with second generation CAR-CD19 (positive control) displaying MFI three-fold higher than the other constructs tested. All three CAR-RUSH (SBP1, SBP2 and SBP3) proteins showed very similar MFI and were therefore expressed at similar levels at the cellular surface.

FIG. 6A-B depict expression and behavior of CAR-RUSH constructs following co-transduction with a lentivector encoding a HOOK-streptavidin, and biotin treatment. Percentage (A) and MFI showing median fluorescence intensity (B) of CAR-positive T lymphocytes analysed by FACS. Cells were co-transduced with a lentivector encoding a HOOK-streptavidin (MOI 5) and a lentivector encoding a CAR-SBP (MOI 5), corresponding to a final total MOI of 10. Biotin was added at the time of co-transduction and cells were analysed at day 3 post-transduction. The percentage and the MFI values reported in the histograms were obtained by subtracting the value from untransduced cells, corresponding to the background. CAR-RUSH constructs were expressed at low percentages specifically following biotin addition into the medium, suggesting that in a co-transduction context, the CAR-RUSH was efficiently retained by the HOOK protein and it was able to be presented at the cellular membrane only upon biotin-mediated induction.

FIG. 7A-B depict expression and behavior of CAR-RUSH bicistronic constructs. Percentage and MFI showing median fluorescence intensity of CAR-positive T lymphocytes analysed by FACS. Cells were transduced at a MOI of 10 (A) or 30 (B) and analysed at day 3 post-transduction. Biotin was added at the time of transduction. The percentage and the MFI values reported in the histograms were obtained by substracting values from untransduced cells, corresponding to the background. SBP1-CD19 and SBP3-CD19 CAR-RUSH constructs showed expression at the cellular surface only upon addition of biotin in the culture medium, suggesting that CAR-RUSH were specifically retained by the HOOK-streptavidin protein in absence of biotin and that, following biotin delivery, the RUSH regulation system induced their trafficking towards and their expression on the plasma membrane. SBP1-CD19 and SBP3-CD19 CAR-RUSH constructs showed expression at the cellular surface upon addition of biotin in the culture medium. At high MOI (MOI=30) and even in absence of biotin, SBP1-CD19 showed slight expression at the cellular surface. In view of these results, CAR-RUSH were considered as largely retained by the HOOK streptavidin protein in the absence of biotin. Moreover, as expected, the biotin delivery induced their trafficking towards, and their expression on the plasma membrane.

FIG. 8A-B depict CAR-RUSH system switch evaluation (OFF/ON). Purified T cells were transduced at day 0 with lentivectors encoding the CAR-RUSH system and biotin was added or not at the same time. At day 3, T cells were analyzed by flow cytometry for the expression of CARs at the T cell surface. Percentage (A) and MFI showing median fluorescence intensity (B) of CAR-positive T lymphocytes from one representative donor analyzed by FACS. CAR-RUSH constructs were transduced at a MOI of 10 or 20, biotin was added at the same time and T cells were analysed for CAR expression at the cellular surface at day 3 post-transduction. The rationale behind this experiment was to study the kinetics of induction of CAR-RUSH constructs upon biotin delivery and the efficiency of CAR-RUSH retention in absence of the biotin inducer. As shown in the top panel, a low percentage of CAR-positive T cells was detected and, depending on the CAR-RUSH construct, the effect was dependent or independent on biotin addition. Depending on the CAR-RUSH construct analyzed, a low percentage of CAR-positive T cells was detected. The ability of biotin to induce CAR-RUSH expression at the cellular surface was detected for CAR-SBP1 and CAR-SBP2. CAR-SBP3 showed a slight CAR expression in both the presence and absence of biotin.

FIG. 9A-D depict CAR-RUSH system switch evaluation (OFF/ON/OFF). Purified T cells were transduced at day 0 with lentivectors encoding the CAR-RUSH system and biotin was added or not at the same time. At day 3 a set of wells was analysed by flow cytometry for the expression of CARs in both the presence and absence of biotin. Other sets of wells were washed and put back in culture with or without biotin, in order to monitor the ability of CAR-positive cells to switch the expression of CAR off. T cells were then analysed for CAR expression at the T cell surface at day 7. Percentage (A) and MFI showing median fluorescence intensity (B) of CAR-positive T lymphocytes analysed by FACS and derived from healthy donor 32. CAR-RUSH constructs were transduced at a MOI of 10 and analysed for CAR expression at the cellular surface at day 7 post-transduction following the re-addition or not of biotin at day 3. As shown in A), a low percentage of CAR-positive T cells was detected. Biotin induced CAR-RUSH expression at the extracellular surface for both CAR-SBP2 and CAR-SBP3 and, in particular for CAR-SBP3, CAR expression was also re-induced following washing and biotin re-addition at day 3. Percentage (C) and MFI showing median fluorescence intensity (D) of CAR-positive T lymphocytes analysed by FACS and derived from healthy donor 31. CAR-RUSH constructs were transduced at a MOI of 20 and analysed for CAR expression at the cellular surface at day 7 post-transduction following the re-addition or not of biotin at day 3. All three CAR-RUSH tested showed a low percentage of CAR-positive cells. In addition, at exception of CAR-SBP1 which showed CAR expression both in the presence and absence of biotin, CAR-RUSH were exclusively expressed in the conditions in which biotin was added at day 0 and/or at day 7.

FIG. 10A-C depicts the amino acid and nucleotide sequences of CAR-CD19 2nd generation and its constituents. A) nucleotide sequence (SEQ ID NO:39), B) amino acid sequence (SEQ ID NO:51), and C) key indicating signal sequence, CD19 ScFv, CD8 hinge, transmembrane domain, 4-1BB, and CD3z sequences.

DETAILED DESCRIPTION OF THE INVENTION

Figure 1:
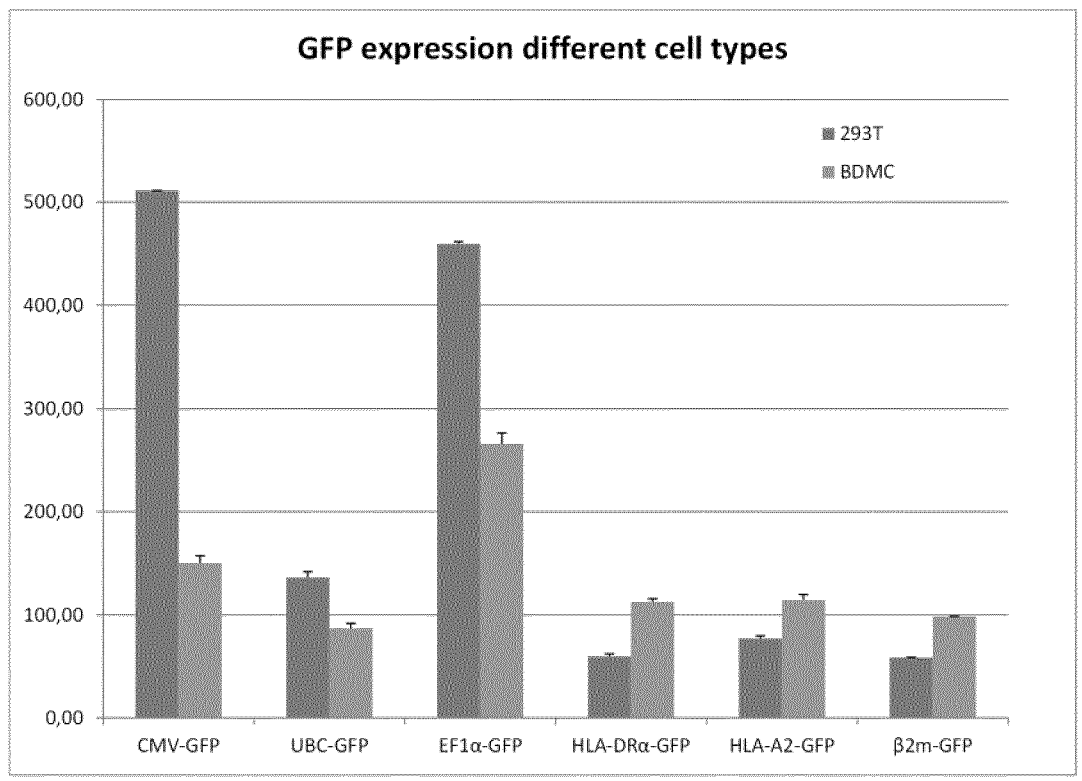
FIG. 1 depicts GFP expression in HEK 293T and BDCM cells from lentivectors with the indicated promoters.

Various lentivector constructs encoding chimeric antigen receptors (CARs) were generated for the expression of CARs in T cells. It was unknown what promoter might be most suitable for expression in human T cells. To compare promoters, a kidney cell line and a dendritic cell line were transduced with lentiviral vectors expressing green fluorescent protein (GFP) from various promoters. It was found that the human EF1α promoter was the strongest promoter in the dendritic cell line BDCM (FIG. 1). This promoter was also very strong in the kidney cell line 293T. Cell-specific expression of various promoters was analyzed using the data sets at biogps.org (FIG. 2). From this data set, expression of the EF1α promoter in T cells is similar to expression in BDCA+ cells. In fact, the human EF1α promoter was used previously to express a CAR in activated human T cells. Budde et al., PLoS ONE 8(12): e82742 (2013.

Based on differences in expression in different cell types, it was not evident which promoters might be used successfully for expression of CARs in human T cells. Human ubiquitin MHC I, MHC II, and β2 microglobulin (β2m) promoters were assessed for their suitability for expression of CARs in human T cells. Unexpectedly, it was found that all of these promoters worked in human T cells (FIG. 3A-C).

In order find the best conditions to generate CAR T-Cells, several parameters that could affect T cells transduction and CAR expression (e.g. MOI, incubation time, promoters, T cell activation and purification strategies) were tested.

Following subtraction of background (% of CAR+ cells in untransduced (UTD) control) CAR+ cells were detected at 24 hrs (UBC vector at MOI=10 and 30), at 96 hrs (β2M vector at MOI=3 and UBC vector MOI=3 and 10) and at 8 days (β2M vector at MOI=30 and UBC vector at every MOI tested). At 96 hrs and at 8 days, a high percentage (about 30%) of CAR-CD19 positive cells in comparison to untransduced lymphocytes was found. At day 7, a high percentage (about 70%) of CAR-CD19 positive cells in comparison to untransduced lymphocytes was found when the viable CD3+ population was analyzed.

Strong expression of CAR-CD19 in several donors (up to 70% of CD3 positive lymphocytes) was found. CAR expression was found even at MOI=3; however, a high percentage of CAR-positive cells was achieved at late time points (day 7 in this experiment). Interestingly, the CAR expression between donors was variable. For CAR-CD19, expression was restricted to the CD3 positive population, as CD3 negative cells failed to express CAR-CD19.

Figure 4:
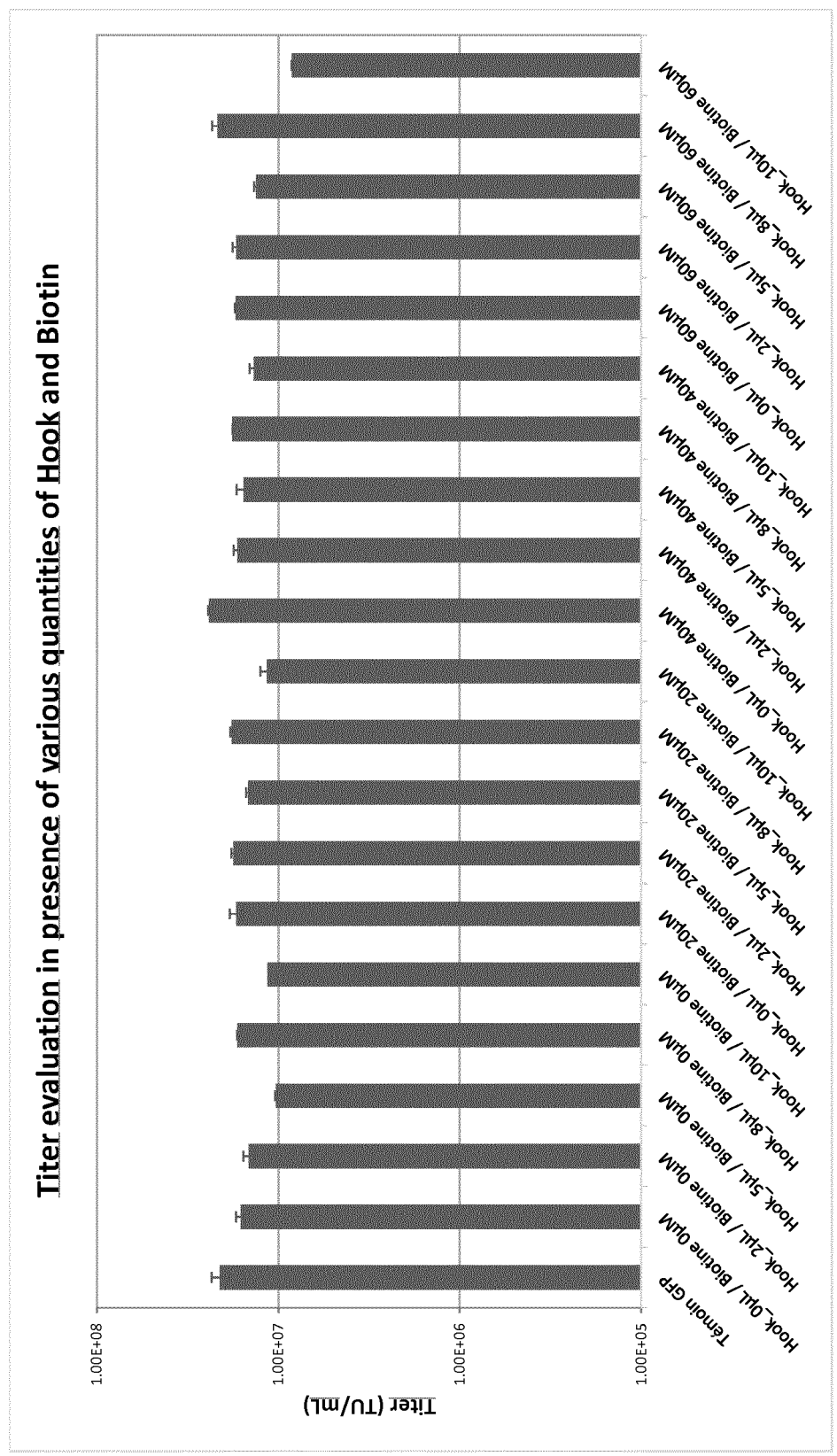
FIG. 4 depicts titers with a pseudotyping vector encoding a codon-optimized VSV-G protein fused to Hook-streptavidin with a dose escalation of hook-streptavidin encoding vector and +/− biotin.

The Hook-streptavidin sequence was cloned into a pseudotyping vector encoding a codon-optimized VSV-G protein as a fusion with VSV-G. This vector was evaluated by cotransfection with a lentivector encoding GFP and a dose escalation of hook-streptavidin encoding vector. No reduction in titers due to retention of the VSV protein in the ER was seen (FIG. 4). Immunofluorescence studies showed a lack of retention of the VSV protein in the ER. This contrasts with the results seen for the VSV protein alone. Nature Methods 9(5): 493-500 (2102). Thus, it was unclear whether CAR expression might be regulated with the Hook-Steptavidin system.

The expression at the surface of T-cells of CAR-CD19 or CAR-CD19 with a streptavidin binding protein (SBP) at various positions between the intracellular domains was evaluated to check whether the presence of the SBP sequence was modifying the CAR expression. CAR-CD19+ with the SBP at various positions were cloned into lentiviral vectors under the control of the β2m promoter.

Human T-cells were transduced with the lentiviral vectors and the expression of the CD19 was evaluated at the surface of the cells. The CAR-CD19-SBP are expressed at the surface of the T-cells, with a slight reduction of the MFI compared to the CAR-CD19 (FIG. 5).

CAR-CD19 lentivectors with the SBP at various positions between the intracellular domains were evaluated in presence of the Hook-Streptavidin. Human T-cells were cotransduced with a lentivector expressing the CAR-CD19-SBP and with a lentivector expressing the Hook-streptavidin and the percentage of transduced cells and MFI were evaluated before or after addition of biotin. It was found that the Hook-streptavidin and the CAR-CD19-SBP can be co-expressed in human T-cells. The presence of the Hook-streptavidin could retain the CAR-CD19-SBP in the endoplasmic reticulum of the T-cells and the addition of biotin in the media induced the release of the CAR-CD19 and its expression at the surface of the cells (FIG. 6).

Figure 11:
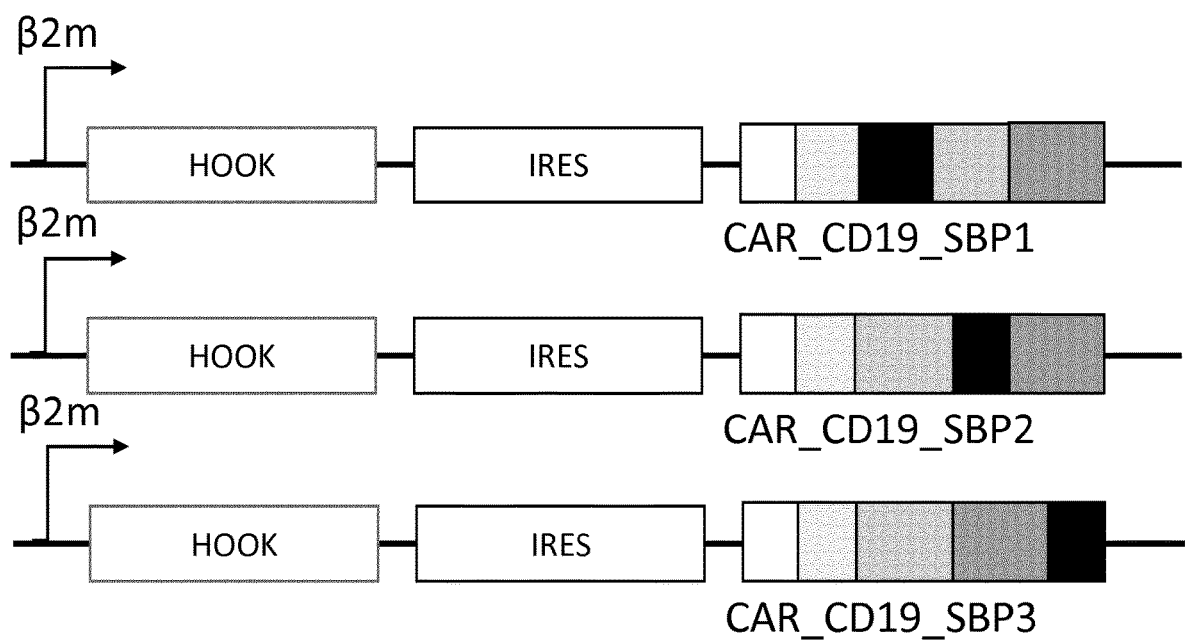
FIG. 11 depicts the structure of the bicistronic HOOK streptavidin-IRES-CAR-SBP-CD19 2nd generation constructs.

Several lentivectors were then constructed containing both the Hook and the CAR containing the SBP at various locations (FIG. 11). The constructs contained the β2m promoter linked to the Hook streptavidin, followed by an IRES linked to the CAR-CD19 with the SBP at 3 different locations.

Human T-cells from various donors were transduced with the lentiviral vectors and the expression of the CAR-CD19-SBP was evaluated at the surface of the cells in the presence and absence of biotin. The Hook-IRES-CAR-CD19-SBP was expressed in human T-cells. The expression of the Hook-streptavidin could retain the CAR-CD19-SBP in the endoplasmic reticulum of the T-cells, regardless of its position. Addition of biotin in the media induced the release of the CAR-CD19 and its expression at the surface of the cells, regardless of its position (FIG. 7).

The present invention encompasses lentiviral vectors encoding a CAR, and their use for the induction of immune responses in a host, especially a human.

Before the present proteins, compositions, methods, and other embodiments are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The term "comprising" as used herein is synonymous with "including" or "containing", and is inclusive or open-ended and does not exclude additional, unrecited members, elements or method steps.

The full name of amino acids is used interchangeably with the standard three letter and one letter abbreviations for each in this disclosure. For the avoidance of doubt, those are: Alanine (Ala, A), Arginine (Arg, R), Asparagine (Asn, N), Aspartic acid (Asp, D), Cysteine (Cys, C), Glutamic Acid (Glu, E), Glutamine (Gln, Q), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), Valine (Val, V).

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe).

As used herein, the term "isolated" refers to a substance or entity that has been (1) separated from at least some of the components with which it was associated when initially produced (whether in nature or in an experimental setting), and (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

The "isolated" products of this invention, including isolated nucleic acids, proteins, polypeptides, and antibodies are not products of nature (i.e., "non-naturally occurring"). Rather, the "isolated" nucleic acids, proteins, polypeptides, and antibodies of this invention are "man-made" products. The "isolated" products of this invention can be "markedly different" or "significantly different" from products of nature. By way of non-limiting example, the isolated nucleic acids may be purified, recombinant, synthetic, labeled, and/or attached to a solid substrate. Such nucleic acids can be markedly different or significantly different than nucleic acids that occur in nature. By way of further non-limiting example, the "isolated" proteins, polypeptides, and antibodies of this invention may be purified, recombinant, synthetic, labeled, and/or attached to a solid substrate. Such proteins, polypeptides, and antibodies can be markedly different or significantly different from proteins, polypeptides, and antibodies that occur in nature.

The term "peptide" as used herein refers to a short polypeptide, e.g., one that typically contains less than about 50 amino acids and more typically less than about 30 amino acids. The term as used herein encompasses analogs and mimetics that mimic structural and thus biological function.

The term "polypeptide" encompasses both naturally-occurring and non-naturally occurring proteins, and fragments, mutants, derivatives and analogs thereof. A polypeptide may be monomeric or polymeric. Further, a polypeptide may comprise a number of different domains each of which has one or more distinct activities. For the avoidance of doubt, a "polypeptide" may be any length greater two amino acids.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from a cell in which it was synthesized.

The protein or polypeptide can be purified. Preferably, the purified protein or polypeptide is more than 50%, 75%, 85%, 90%, 95%, 97%, 98%, or 99% pure. Within the context of this invention, a purified protein that is more than 50% (etc.) pure means a purified protein sample containing less than 50% (etc.) other proteins. For example, a sample of a protein comprising can be 99% pure if it contains less than 1% contaminating host cell proteins.

The term "polypeptide fragment" as used herein refers to a polypeptide that has a deletion, e.g., an amino-terminal and/or carboxy-terminal deletion compared to a full-length polypeptide, such as a naturally occurring protein. In an embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, or at least 12, 14, 16 or 18 amino acids long, or at least 20 amino acids long, or at least 25, 30, 35, 40 or 45, amino acids, or at least 50 or 60 amino acids long, or at least 70 amino acids long, or at least 100 amino acids long.

The term "fusion protein" refers to a polypeptide comprising a polypeptide or fragment coupled to heterologous amino acid sequences. Fusion proteins are useful because they can be constructed to contain two or more desired functional elements that can be from two or more different proteins. A fusion protein comprises at least 10 contiguous amino acids from a polypeptide of interest, or at least 20 or 30 amino acids, or at least 40, 50 or 60 amino acids, or at least 75, 100 or 125 amino acids. The heterologous polypeptide included within the fusion protein is usually at least 6 amino acids in length, or at least 8 amino acids in length, or at least 15, 20, or 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, "recombinant" may refer to a biomolecule, e.g., a gene or protein, or to an organism. The term "recombinant" may be used in reference to cloned DNA isolates, chemically synthesized polynucleotides, or polynucleotides that are biologically synthesized by heterologous systems, as well as proteins or polypeptides and/or RNAs encoded by such nucleic acids. A "recombinant" nucleic acid is a nucleic acid linked to a nucleotide or polynucleotide to which it is not linked in nature. A "recombinant" protein or polypeptide may be (1) a protein or polypeptide linked to an amino acid or polypeptide to which it is not linked in nature; and/or (2) a protein or polypeptide made by transcription and/or translation of a recombinant nucleic acid. Thus, a protein synthesized by a microorganism is recombinant, for example, if it is synthesized from an mRNA synthesized from a recombinant nucleic acid present in the cell. A "recombinant" cell is a cell comprising a "recombinant" biomolecule. For example, a T cell that comprises a "recombinant" nucleic acid is a "recombinant" cell.

The term "polynucleotide", "nucleic acid molecule", "nucleic acid", or "nucleic acid sequence" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The nucleic acid (also referred to as polynucleotides) may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

A "synthetic" RNA, DNA or a mixed polymer is one created outside of a cell, for example one synthesized chemically.

The term "nucleic acid fragment" as used herein refers to a nucleic acid sequence that has a deletion, e.g., a 5'-terminal or 3'-terminal deletion compared to a full-length reference nucleotide sequence. In an embodiment, the nucleic acid fragment is a contiguous sequence in which the nucleotide sequence of the fragment is identical to the corresponding positions in the naturally-occurring sequence. In some embodiments, fragments are at least 10, 15, 20, or 25 nucleotides long, or at least 20, 30, 40, 50, 60, 70, 80, 90, 100, 110, 120, 130, 140, or 150 nucleotides long. In some embodiments a fragment of a nucleic acid sequence is a fragment of an open reading frame sequence. In some embodiments such a fragment encodes a polypeptide fragment (as defined herein) of the protein encoded by the open reading frame nucleotide sequence.

The nucleic acid can be purified. Preferably, the purified nucleic acid is more than 50%, 75%, 85%, 90%, 95%, 97%, 98%, or 99% pure. Within the context of this invention, a purified nucleic acid that is at least 50% pure means a purified nucleic acid sample containing less than 50% other nucleic acids. For example, a sample of a plasmid can be at least 99% pure if it contains less than 1% contaminating bacterial DNA.

As used herein, an endogenous nucleic acid sequence in the genome of an organism (or the encoded protein product of that sequence) is deemed "recombinant" herein if a heterologous sequence is placed adjacent to the endogenous nucleic acid sequence. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32, and even more typically at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

As used herein, an "expression control sequence" refers to polynucleotide sequences which affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to encompass, at a minimum, any component whose presence is essential for expression, and can also encompass an additional component whose presence is advantageous, for example, leader sequences and fusion partner sequences.

As used herein, "operatively linked" or "operably linked" expression control sequences refers to a linkage in which the expression control sequence is contiguous with the gene of interest to control the gene of interest, as well as expression control sequences that act in trans or at a distance to control the gene of interest.

As used herein, a "vector" is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors"). The integrating cosmid vector pYUB412 is an example of a "vector".

The term "recombinant host cell" (or simply "recombinant cell" or "host cell"), as used herein, is intended to refer to a cell into which a recombinant nucleic acid such as a recombinant vector has been introduced. In some instances the word "cell" is replaced by a name specifying a type of cell. For example, a "recombinant microorganism" is a recombinant host cell that is a microorganism host cell. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "recombinant host cell," "recombinant cell," and "host cell", as used herein. A recombinant host cell may be an isolated cell or cell line grown in culture or may be a cell which resides in a living tissue or organism.

As used herein, the term "mammal" refers to any member of the taxonomic class mammalia, including placental mammals and marsupial mammals. Thus, "mammal" includes humans, primates, livestock, and laboratory mammals. Exemplary mammals include a rodent, a mouse, a rat, a rabbit, a dog, a cat, a sheep, a horse, a goat, a llama, cattle, a primate, a pig, and any other mammal. In some embodiments, the mammal is at least one of a transgenic mammal, a genetically-engineered mammal, and a cloned mammal.

Chimeric Antigen Receptors

The invention encompasses a chimeric antigen receptor (CAR) comprising an extracellular antigen-binding domain (binding domain), a hinge and transmembrane domain (transmembrane domain); a hook-binding domain; and an intracellular signaling domain (activation domain). The CAR can contain one, two, three, or more of each of these domains.

The invention encompasses individually all possible combinations of the specific polypeptides and fragments thereof recited herein.

The invention encompasses CARs comprising a hook-binding domain. A "hook-binding domain" is a domain that reversibly binds directly or indirectly to a "hook" protein inside of the cell, which binding prevents the CAR from exiting the endoplasmic reticulum (ER) or Golgi under appropriate conditions.

In one embodiment, the hook-binding domain comprises a streptavidin-binding peptide (SBP), which can bind to a hook protein that bears the core streptavidin. Biotin causes the release of the CAR containing the hook-binding domain from the hook by out-competing the SBP. The CAR can then move to the cell membrane.

Preferably, a system referred to as RUSH (retention using selective hooks) system can be employed, Boncompain et al., Nat. Methods 9:493-498, 2012, which is hereby incorporated by reference.

Preferably, the hook-binding domain comprises the amino acid sequence: MDEKTTGWRGGHWEGLAGELEQL-RARLEHHPQGQREP (SEQ ID NO:1) or is encoded by the nucleic acid sequence:

(SEQ ID NO: 2)
ATGGACGAGAAAACCACCGGCTGGCGGGGAGGCCACGTGGTGGAAGGAC

TGGCCGGCGAGCTGGAACAGCTGCGGGCCAGACTGGAACACCACCCCCA

GGGCCAGAGAGAGCCC.

Shorter SBP fragments, deleted at their N-terminus and C-terminus may be used with identical efficacy. See Barrette-Ng, I. H., S. C. Wu, W. M. Tjia, S. L. Wong, and K. K. Ng. 2013, The structure of the SBP-Tag-streptavidin complex reveals a novel helical scaffold bridging binding pockets on separate subunits, *Acta crystallographica*. Section D, Biological crystallography 69:879-887.

One embodiment of a hook-binding domain is set forth in WO2010/142785, which is hereby incorporated by reference. The FKBPF-K506 binding domain 12 (FKBPI2) can be used with FKBP-rapamycin associated protein (FRAP) as the hook. In this embodiment, the interaction occurs only in the presence of rapamycin or analogues thereof that are able to mediate the interaction between FKBP12 and FRAP and can be, in particular, selected from the group consisting of FKI012, FK-CsA, and rapamycin.

In one embodiment, the hook-binding domain is located in the intracytoplasmic region of the CAR. In other embodiments, the hook-binding domain is located in other positions, i.e., in all the junctions between the different intracytoplamsic elements (e.g., between the transmembrane region and the first co-stimulation element) or between the different co-stimulation elements.

The invention comprises CARs containing a binding domain that comprises an antibody that binds specifically to a human polypeptide. The term "antibody" is meant to include polyclonal antibodies, monoclonal antibodies, fragments thereof, such as F(ab')2 and Fab fragments, single-chain variable fragments (scFvs), single-domain antibody fragments (VHHs or Nanobodies, preferably camelid), and bivalent and trivalent antibody fragments (diabodies and triabodies).

Preferably, the antibody is a single-chain Fv antibody or a nanobody.

In one embodiment, the antibody is monospecific. In one embodiment, the antibody is multispecific for 2, 3, or 4 polypeptides. Preferably, the antibody is bispecific.

Antibodies can be synthetic, monoclonal, or polyclonal and can be made by techniques well known in the art. Such antibodies specifically bind to human proteins via the antigen-binding sites of the antibody (as opposed to non-specific binding). Human proteins, polypeptide fragments, and peptides can be employed as immunogens in producing antibodies immunoreactive therewith. The human proteins, polypeptides, and peptides contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the conformation of the protein and steric hindrance, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes can be identified by any of the methods known in the art.

Thus, one aspect of the present invention relates to the antigenic epitopes of human proteins. Such epitopes are useful for raising antibodies, in particular monoclonal antibodies, as described in detail below.

Antibodies are defined to be specifically binding if they bind human proteins or polypeptides with a Ka of greater than or equal to about $10^7$ $M^{-1}$. Affinities of binding partners or antibodies can be readily determined using conventional techniques, for example those described by Scatchard et al., Ann. N.Y. Acad. Sci., 51:660 (1949).

Polyclonal antibodies can be readily generated from a variety of sources, for example, horses, cows, goats, sheep, dogs, chickens, rabbits, mice, or rats, using procedures that are well known in the art. In general, a purified human protein or polypeptide that is appropriately conjugated is administered to the host animal typically through parenteral injection. The immunogenicity can be enhanced through the use of an adjuvant, for example, Freund's complete or incomplete adjuvant. Following booster immunizations, small samples of serum are collected and tested for reactivity to human proteins or polypeptides. Examples of various assays useful for such determination include those described in Antibodies: A Laboratory Manual, Harlow and Lane (eds.), Cold Spring Harbor Laboratory Press, 1988; as well as procedures, such as countercurrent immuno-electrophoresis (CIEP), radioimmunoassay, radio-immunoprecipitation, enzyme-linked immunosorbent assays (ELISA), dot blot assays, and sandwich assays. See U.S. Pat. Nos. 4,376,110 and 4,486,530.

Monoclonal antibodies can be readily prepared using well known procedures. See, for example, the procedures described in U.S. Pat. Nos. RE 32,011, 4,902,614, 4,543,439, and 4,411,993; Monoclonal Antibodies, Hybridomas: A New Dimension in Biological Analyses, Plenum Press, Kennett, McKeam, and Bechtol (eds.), 1980.

For example, the host animals, such as mice, can be injected intraperitoneally at least once and preferably at least twice at about 3 week intervals with isolated and purified human proteins or conjugated human polypeptides, for example a peptide comprising or consisting of the specific amino acids set forth above. Mouse sera are then assayed by conventional dot blot technique or antibody capture (ABC) to determine which animal is best to fuse. Approximately two to three weeks later, the mice are given an intravenous boost of the human protein or polypeptide. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as a labeled human protein or polypeptide, is added to each well followed by incubation. Positive wells can be subsequently detected. Positive clones can be grown in bulk culture and supernatants are subsequently purified over a Protein A column (Pharmacia).

The monoclonal antibodies of the invention can be produced using alternative techniques, such as those described by Alting-Mees et al., "Monoclonal Antibody Expression Libraries: A Rapid Alternative to Hybridomas", Strategies in Molecular Biology 3:1-9 (1990), which is incorporated herein by reference. Similarly, binding partners can be constructed using recombinant DNA techniques to incorporate the variable regions of a gene that encodes a specific binding antibody. Such a technique is described in Larrick et al., Biotechnology, 7:394 (1989).

Antigen-binding fragments of such antibodies, which can be produced by conventional techniques, are also encompassed by the present invention. Examples of such fragments include, but are not limited to, Fab and F(ab')2 fragments. Antibody fragments and derivatives produced by genetic engineering techniques are also provided.

The monoclonal antibodies of the present invention include chimeric antibodies, e.g., humanized versions of murine monoclonal antibodies. Such humanized antibodies can be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment can comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (Nature 332:323, 1988), Liu et al. (PNAS 84:3439, 1987), Larrick et al. (Bio/Technology 7:934, 1989), and Winter and Harris (TIPS 14:139, May, 1993). Procedures to generate antibodies transgenically can be found in GB 2,272,440, U.S. Pat. Nos. 5,569,825 and 5,545,806.

Antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Publication No. WO 87/02671; Akira, et al. European Patent Application 0184187; Taniguchi, M., European Patent Application 0171496; Morrison et al. European Patent Application 0173494; Neuberger et al. PCT International Publication No. WO 86/01533; Cabilly et al. U.S. Pat. No. 4,816,567; Cabilly et al. European Patent Application 0125023; Better et al., Science 240:1041 1043, 1988; Liu et al., PNAS 84:3439 3443, 1987; Liu et al., J. Immunol. 139:3521 3526, 1987; Sun et al. PNAS 84:214 218, 1987;

Nishimura et al., Canc. Res. 47:999 1005, 1987; Wood et al., Nature 314:446 449, 1985; and Shaw et al., J. Natl. Cancer Inst. 80:1553 1559, 1988); Morrison, S. L., Science 229: 1202 1207, 1985; Oi et al., BioTechniques 4:214, 1986; Winter U.S. Pat. No. 5,225,539; Jones et al., Nature 321:552 525, 1986; Verhoeyan et al., Science 239:1534, 1988; and Beidler et al., J. Immunol. 141:4053 4060, 1988.

An immunoglobulin library can be expressed by a population of display packages, preferably derived from filamentous phage, to form an antibody display library. Examples of methods and reagents particularly amenable for use in generating antibody display library can be found in, for example, Ladner et al. U.S. Pat. No. 5,223,409; Kang et al. PCT publication WO 92/18619; Dower et al. PCT publication WO 91/17271; Winter et al. PCT publication WO 92/20791; Markland et al. PCT publication WO 92/15679; Breitling et al. PCT publication WO 93/01288; McCafferty et al. PCT publication WO 92/01047; Garrard et al. PCT publication WO 92/09690; Ladner et al. PCT publication WO 90/02809; Fuchs et al. (1991) Bio/Technology 9:1370 1372; Hay et al. (1992) Hum Antibod Hybridomas 3:81 85; Huse et al. (1989) Science 246:1275 1281; Griffths et al. (1993) supra; Hawkins et al. (1992) J Mol Biol 226:889 896; Clackson et al. (1991) Nature 352:624 628; Gram et al. (1992) PNAS 89:3576 3580; Garrad et al. (1991) Bio/Technology 9:1373 1377; Hoogenboom et al. (1991) Nuc Acid Res 19:4133 4137; and Barbas et al. (1991) PNAS 88:7978 7982. Once displayed on the surface of a display package (e.g., filamentous phage), the antibody library is screened to identify and isolate packages that express an antibody that binds a human protein or polypeptide. In a preferred embodiment, the primary screening of the library involves panning with an immobilized human protein or polypeptide and display packages expressing antibodies that bind immobilized human protein or polypeptide are selected.

In connection with synthetic and semi-synthetic antibodies, such terms are intended to cover but are not limited to antibody fragments, isotype switched antibodies, humanized antibodies (e.g., mouse-human, human-mouse), hybrids, antibodies having plural specificities, and fully synthetic antibody-like molecules.

The invention encompasses a CAR comprising an activation domain comprising CD3-ζ or Fc receptor γ amino acid sequences. Sadelain et al., Cancer Discov. 2013 April; 3(4): 388-398, which is hereby incorporated by reference. The invention further encompasses a CAR comprising an activation domain comprising a CD3-ζ chain and the cytoplasmic domain of a costimulatory receptor such as CD28, 4-1BB (CD137), DAP10, OX40 (CD134), ICOS, CD27, or CD40L. Id.

Preferably, the CAR comprises a fragment of at least 50, 60, 70, 80, 90, 100, 110, 120, 150, or 200 amino acids of at least one of the following amino acid sequences having T-cell activating activity.

CD3-ζ:
(SEQ ID NO: 3)
MKWKALFTAA ILQAQLPITE AQSFGLLDPK LCYLLDGILF

IYGVILTALF LRVKFSRSAD APAYQQGQNQ LYNELNLGRR

EEYDVLDKRR GRDPEMGGKP QRRKNPQEGL YNELQKDKMA

EAYSEIGMKG ERRRGKGHDG LYQGLSTATK DTYDALHMQA

LPPR

CD28:
(SEQ ID NO: 4)
MLRLLLALNL FPSIQVTGNK ILVKQSPMLV AYDNAVNLSC

KYSYNLFSRE FRASLHKGLD SAVEVCVVYG NYSQQLQVYS

KTGFNCDGKL GNESVTFYLQ NLYVNQTDIY FCKIEVMYPP

PYLDNEKSNG TIIHVKGKHL CPSPLFPGPS KPFWVLVVVG

GVLACYSLLV TVAFIIFWVR SKRSRLLHSD YMNMTPRRPG

PTRKHYQPYA PPRDFAAYRS 4-1BB (CD137):
(SEQ ID NO: 5)
MGNSCYNIVA TLLLVLNFER TRSLQDPCSN CPAGTFCDNN

RNQICSPCPP NSFSSAGGQR TCDICRQCKG VFRTRKECSS

TSNAECDCTP GFHCLGAGCS MCEQDCKQGQ ELTKKGCKDC

CFGTFNDQKR GICRPWTNCS LDGKSVLVNG TKERDVVCGP

SPADLSPGAS SVTPPAPARE PGHSPQIISF FLALTSTALL

FLLFFLTLRF SVVKRGRKKL LYIFKQPFMR PVQTTQEEDG

CSCRFPEEEE GGCEL

DAP10:
(SEQ ID NO: 6)
MIHLGHILFL LLLPVAAAQT TPGERSSLPA FYPGTSGSCS

GCGSLSLPLL AGLVAADAVA SLLIVGAVFL CARPRRSPAQ

EDGKVYINMP GRG

OX40 (CD134):
(SEQ ID NO: 7)
MCVGARRLGR GPCAALLLLG LGLSTVTGLH CVGDTYPSND

RCCHECRPGN GMVSRCSRSQ NTVCRPCGPG FYNDVVSSKP

CKPCTWCNLR SGSERKQLCT ATQDTVCRCR AGTQPLDSYK

PGVDCAPCPP GHFSPGDNQA CKPWTNCTLA GKHTLQPASN

SSDAICEDRD PPATQPQETQ GPPARPITVQ PTEAWPRTSQ

GPSTRPVEVP GGRAVAAILG LGLVLGLLGP LAILLALYLL

RRDQRLPPDA HKPPGGGSFR TPIQEEQADA HSTLAKI

ICOS:
(SEQ ID NO: 8)
MKSGLWYFFLFCLRIKVLIGEINGSANYEMFIFHNGGVQILCK

YPDIVQQFKMQLLKGGQILCDLTKTKGSGNTVSIKSLKFCHSQ

LSNNSVSFFLYNLDHSHANYYFCNLSIFDPPPFKVTLTGGYLH

IYESQLCCQLKFWLPIGCAAFVVVCILGCILICWLTKKKYSSS

VHDPNGEYMFMRAVNTAKKSRLTDVTL

CD27:
(SEQ ID NO: 33)
MARPHPWWLCVLGTLVGLSATPAPKSCPERHYWAQGKLCCQMC

EPGTFLVKDCDQHRKAAQCDPCIPGVSFSPDHHTRPHCESCRH

CNSGLLVRNCTITANAECACRNGWQCRDKECTECDPLPNPSLT

ARSSQALSPHPQPTHLPYVSEMLEARTAGHMQTLADFRQLPAR

TLSTHWPPQRSLCSSDFIRILVIFSGMFLVFTLAGALFLHQRR

-continued
KYRSNKGESPVEPAEPCHYSCPREEEGSTIPIQEDYRKPEPAC

SP

CD40L (CD154):
(SEQ ID NO: 34)
MIETYNQTSPRSAATGLPISMKIFMYLLTVFLITQMIGSALFA

VYLHRRLDKIEDERNLHEDFVFMKTIQRCNTGERSLSLLNCEE

IKSQFEGFVKDIMLNKEETKKENSFEMQKGDQNPQIAAHVISE

ASSKTTSVLQWAEKGYYTMSNNLVTLENGKQLTVKRQGLYYIY

AQVTFCSNREASSQAPFIASLCLKSPGRFERILLRAANTHSSA

KPCGQQSIHLGGVFELQPGASVFVNVTDPSQVSHGTGFTSFGL

LKL

In various embodiments, CAR comprises a fragment of at least 20, 30, 40, 50, 60, 70, 80, 90, 100, 110, 120, 150, or 200 amino acids that shares at least than 90%, preferably more than 95%, more preferably more than 99% identity with the amino acid sequence of SEQ ID NO:3, SEQ ID NO:4, SEQ ID NO:5, SEQ ID NO:6, SEQ ID NO:7, SEQ ID NO:8, SEQ ID NO:33, or SEQ ID NO:34.

In various embodiments, the activation domain of the CAR comprises one, two, three, or more fragments of at least 20, 30, 40, 50, 60, 70, 80, 90, 100, 110, 120, 150, or 200 amino acids that share at least than 90%, preferably more than 95%, more preferably more than 99% identity with the amino acid sequence of SEQ ID NO:3, SEQ ID NO:4, SEQ ID NO:5, SEQ ID NO:6, SEQ ID NO:7, SEQ ID NO:8, SEQ ID NO:33, or SEQ ID NO:34.

The invention encompasses a CAR comprising a transmembrane (TM) domain, preferably a fragment of at least 20, 30, 40, 50, 60, 70, 80, 90, 100, 110, 120, 150, or 200 amino acids, most preferably of at least one of CD28, CD3z, CD8, CD4, FcRγ, TM regions.

The CAR can be purified. Preferably, the purified CAR is more than 50%, 75%, 85%, 90%, 95%, 97%, 98%, or 99% pure. Within the context of this invention, a purified CAR that is more than 50% (etc.) pure means a purified CAR sample containing less than 50% (etc.) other proteins. For example, a sample of a recombinant CAR purified from a host cell can be 99% pure if it contains less than 1% contaminating host cell proteins.

In a preferred embodiment, the CAR encodes the amino acid sequence of any of SEQ ID NO:46, SEQ ID NO:48, or SEQ ID NO:50.

Particularly preferred CARs include those encoding any of the constituents of the CAR depicted in FIG. 11, including signal sequence, CD19 ScFv, CD8 hinge, transmembrane domain, 4-1BB, and/or CD3z sequences. Other preferred CARs include those encoding any of the constituents of the CARs of SEQ ID NOs:44-50. Particularly preferred CARs have the CD19 ScFv domain replaced by another binding region.

Nucleic Acids

The invention encompasses nucleic acids encoding a CAR. The nucleic acid can be single-stranded or double-stranded. The nucleic acid can be an RNA or DNA molecule. Preferred nucleic acids encode an amino acid sequence of at least one of the SEQ ID NOs detailed herein. The invention encompasses an isolated nucleic acid of the invention inserted into a vector.

In one embodiment, the nucleic acid sequence comprises the nucleic acid sequence of SEQ ID NO:2. In one embodiment the nucleic acid sequence comprises one or more of the following nucleic acid sequences:

HOOK: (CORE + HA TAG + OTHER SEQUENCE)
(SEQ ID NO: 35)
ATGCACCGGAGGAGATCACGCTCTTGTAGGGAGGACCAGAAACCTGTC

ACCGGTGACCCTAGCAAAGACTCAAAAGCTCAGGTGTCCGCTGCCGAG

GCTGGCATTACTGGAACATGGTACAATCAGCTCGGGAGCACCTTTATT

GTGACTGCTGGAGCCGATGGAGCCCTCACCGGAACATACGAATCTGCT

GTGGGAAACGCCGAATCACGGTACGTCCTCACTGGCCGATACGATAGT

GCCCCTGCCACCGACGGATCTGGGACTGCCCTGGGATGGACTGTCGCT

TGGAAAAACAACTACCGGAATGCTCATTCTGCCACAACATGGAGTGGA

CAGTACGTGGGAGGCGCTGAGGCTAGAATCAATACACAGTGGCTGCTC

ACATCTGGCACAACCGAGGCAAATGCTTGGAAATCCACCCTGGTGGGA

CATGACACATTCACCAAAGTGAAACCCTCCGCCGCTTCAATCGATGCC

GCCAAAAAGCCGGAGTCAACAACGGCAATCCTCTGGATGCCGTCCAG

CAGGTCGACTATCCGTACGACGTACCAGACTACGCAGTCGGACCGATG

GACGATCAGAGGGACCTCATTAGCAACAACGAACAGCTGCCTATGCTG

GGACGGCGACCTGGAGCCCCTGAATCCAAATGCTCTAGGGGAGCACTG

TACACTGGCTTCTCCATTCTCGTGACACTGCTGCTGGCCGGGCAGGCT

ACTACTGCTTACTTCCTGTACCAGCAGCAGGGGCGGCTGGACAAACTC

ACTGTGACATCTCAGAACCTCCAGCTGGAAAATCTGAGGATGAAACTG

CCCAAACCCCCTAAACCCGTGTCCAAAATGAGGATGGCCACACCTCTG

CTCATGCAGGCACTGCCAATGGGAGCCCTGCCCCAGGGGCCCATGCAG

AATGCCACCAAGTATGGCAACATGACAGAGGACCATGTGATGCACCTG

CTCCAGAATGCTGACCCCCTGAAGGTGTACCCGCCACTGAAGGGGAGC

TTCCCGGAGAACCTGAGACACCTTAAGAACACCATGGAGACCATAGAC

TGGAAGGTCTTTGAGAGCTGGATGCACCATTGGCTCCTGTTTGAAATG

AGCAGGCACTCCTTGGAGCAAAAGCCCACTGACGCTCCACCGAAAGAG

TCACTGGAACTGGAGGACCCGTCTTCTGGGCTGGGTGTGACCAAGCAG

GATCTGGGCCCAGTCCCCATGTGA.

CORE STREPTAVIDIN:
(SEQ ID NO: 36)
GACCCTAGCAAAGACTCAAAAGCTCAGGTGTCCGCTGCCGAGGCTGGC

ATTACTGGAACATGGTACAATCAGCTCGGGAGCACCTTTATTGTGACT

GCTGGAGCCGATGGAGCCCTCACCGGAACATACGAATCTGCTGTGGGA

AACGCCGAATCACGGTACGTCCTCACTGGCCGATACGATAGTGCCCCT

GCCACCGACGGATCTGGGACTGCCCTGGGATGGACTGTCGCTTGGAAA

AACAACTACCGGAATGCTCATTCTGCCACAACATGGAGTGGACAGTAC

GTGGGAGGCGCTGAGGCTAGAATCAATACACAGTGGCTGCTCACATCT

GGCACAACCGAGGCAAATGCTTGGAAATCCACCCTGGTGGGACATGAC

ACATTCACCAAAGTGAAACCCTCCGCCGCTTCAATCGATGCCGCCAAA

AAAGCCGGAGTCAACAACGGCAATCCTCTGGATGCCGTCCAGCAG.

HA TAG:
(SEQ ID NO: 37)
TATCCGTACGACGTACCAGACTACGCA.

Preferred nucleic acids are of at least 50, 60, 70, 80, 90, 100, 110, 120, 150, 200, 300, 400, 500, or 600 nucleotides.

The nucleic acid can be purified. Preferably, the purified nucleic acid is more than 50%, 75%, 85%, 90%, 95%, 97%, 98%, or 99% pure. Within the context of this invention, a purified nucleic acid that is more than 50% pure means a purified nucleic acid sample containing less than 50% other nucleic acids. For example, a sample of a plasmid purified from a host bacteria can be 99% pure if it contains less than 1% contaminating bacterial DNA.

Particularly preferred nucleic acids include the following:

```
CAR_CD19 2^Nd generation: 1518 bp
                                             (SEQ ID NO: 39)
ATGGCCCTGCCTGTGACAGCCCTGCTGCTGCCCCTGGCTCTCCTGCTG
CATGCCGCCAGACCCGCTAGCGACATCCAGATGACCCAGACCACCAGC
AGCCTGAGCGCCAGCCTGGGCGACAGAGTGACCATCAGCTGCCGGGCC
AGCCAGGACATCAGCAAGTACCTGAACTGGTATCAGCAGAAACCCGAC
GGCACCGTGAAGCTGCTGATCTACCACACCAGCCGGCTCCACAGCGGC
GTGCCCAGCAGATTTTCTGGCAGCGGCAGCGGCACCGACTACAGCCTG
ACCATCTCCAACCTGGAACAGGAAGATATCGCTACCTACTTCTGTCAG
CAAGGCAACACCCTGCCCTACACCTTCGGCGGAGGCACCAAGCTGGAA
ATCACCGGCGGAGGCGGAAGTGGAGGTGGAGGATCTGGCGGCGGAGGC
TCCGAAGTGAAGCTGCAGGAAAGCGGCCCTGGCCTCGTGGCCCCTAGC
CAGAGCCTGTCCGTGACCTGTACCGTGTCCGGCGTGTCCCTGCCCGAC
TACGGCGTGTCCTGGATCAGACAGCCTCCCAGAAAGGGCCTGGAATGG
CTGGGCGTGATCTGGGGCAGCGAGACAACCTACTACAACAGCGCCCTG
AAGTCCCGGCTGACCATCATCAAGGACAACAGCAAGAGCCAGGTGTTC
CTGAAGATGAACAGCCTGCAGACCGACGACACCGCCATCTACTACTGC
GCCAAGCACTACTACTACGGCGGCAGCTACGCCATGGACTACTGGGGC
CAGGGCACCAGCGTGACCGTGTCCAGCCATATGGCCCTGAGCAACAGC
ATCATGTACTTCAGCCACTTCGTGCCCGTGTTTCTGCCCGCCAAGCCC
ACCACCACCCCTGCCCCTAGACCTCCCACCCCAGCCCCAACAATCGCC
AGCCAGCCTCTGTCCCTGCGGCCCGAAGCCTGTAGACCTGCTGCCGGC
GGAGCCGTGCACACCAGAGGCCTGGATATCTACATCTGGGCCCCTCTG
GCCGGCACCTGTGGCGTGCTGCTGCTGAGCCTGGTGATCACAAAGCGG
GGCAGAAAGAAGCTGCTGTACATCTTCAAGCAGCCATTCATGCGGCCC
GTGCAGACCACCCAGGAAGAGGACGGCTGCAGCTGCCGGTTCCCCGAG
GAAGAGGAAGGCGGCTGCGAACTGCCCAAGCTGTGCTACCTGCTGGAC
GGCATCCTGTTCATCTATGGCGTGATCCTGACCGCCCTGTTCCTGAGA
GTGAAGTTCAGCAGAAGCGCCGACGCCCCTGCCTACCAGCAGGGCCAG
AACCAGCTGTACAACGAGCTGAACCTGGGCAGACGGGAAGAGTACGAC
GTGCTGGACAAGCGGAGAGGCCGGGACCCTGAGATGGGCGGCAAGCCC
CAGCGGCGGAAGAACCCTCAGGAAGGCCTGTATAACGAACTGCAGAAA
GACAAGATGGCCGAGGCCTACAGCGAGATCGGCATGAAGGGCGAGCGG
CGGAGAGGCAAGGGCCACGATGGCCTGTAC CAR_CD19 3^rd generation: 1641 bp
                                             (SEQ ID NO: 40)
ATGGCCCTGCCTGTGACAGCCCTGCTGCTGCCCCTCGCTCTGCTGCTG
CATGCCGCCAGACCCGCTAGCGACATCCAGATGACCCAGACCACCAGC
AGCCTGAGCGCCAGCCTGGGCGACAGAGTGACCATCAGCTGCCGGGCC
AGCCAGGACATCAGCAAGTACCTGAACTGGTATCAGCAGAAACCCGAC
GGCACCGTGAAGCTGCTGATCTACCACACCAGCCGGCTCCACAGCGGC
GTGCCCAGCAGATTTTCTGGCAGCGGCAGCGGCACCGACTACAGCCTG
ACCATCTCCAACCTGGAACAGGAAGATATCGCTACCTACTTCTGTCAG
CAAGGCAACACCCTGCCCTACACCTTCGGCGGAGGCACCAAGCTGGAA
ATCACCGGCGGAGGCGGAAGTGGAGGGGGAGGATCTGGCGGCGGAGGC
TCCGAAGTGAAGCTGCAGGAAAGCGGCCCTGGCCTGGTGGCCCCTAGC
CAGAGCCTGTCCGTGACCTGTACCGTGTCCGGCGTGTCCCTGCCCGAC
TACGGCGTGTCCTGGATCAGACAGCCCCCCAGAAAGGGCCTGGAATGG
CTGGGCGTGATCTGGGGCAGCGAGACAACCTACTACAACAGCGCCCTG
AAGTCCCGGCTGACCATCATCAAGGACAACAGCAAGAGCCAGGTGTTC
CTGAAGATGAACAGCCTGCAGACCGACGACACCGCCATCTACTACTGC
GCCAAGCACTACTACTACGGCGGCAGCTACGCCATGGACTACTGGGGC
CAGGGCACCAGCGTGACCGTGTCCAGCCATATGGCCCTGAGCAACAGC
ATCATGTACTTCAGCCACTTCGTGCCCGTGTTTCTGCCCGCCAAGCCC
ACCACCACCCCTGCCCCTAGACCTCCCACCCCAGCCCCAACAATCGCC
AGCCAGCCTCTGTCCCTGAGGCCCGAAGCCTGTAGACCTGCTGCCGGC
GGAGCCGTGCACACCAGAGGCCTGGATATCTACATCTGGGCCCCTCTG
GCCGGCACCTGTGGCGTGCTGCTGCTGAGCCTGGTGATCACCCGGTCC
AAGCGGAGCAGACTGCTGCACTCCGACTACATGAACATGACCCCCAGA
CGGCCTGGCCCCACCCGGAAGCACTACCAGCCTTACGCCCCTCCCCGG
GACTTCGCCGCCTACAGAAGCAAGCGGGGCAGAAAGAAGCTGCTGTAC
ATCTTCAAGCAGCCCTTCATGCGGCCCGTGCAGACCACCCAGGAAGAG
GACGGCTGCAGCTGCCGGTTCCCCGAGGAAGAGGAAGGCGGCTGCGAA
CTGCCCAAGCTGTGCTACCTGCTGGACGGCATCCTGTTCATCTATGGC
GTGATCCTGACCGCCCTGTTCCTGAGAGTGAAGTTCAGCAGAAGCGCC
GACGCCCCTGCCTACCAGCAGGGCCAGAACCAGCTGTACAACGAGCTG
AACCTGGGCAGACGGGAAGAGTACGACGTGCTGGACAAGCGCAGAGGC
CGGGACCCTGAGATGGGCGGCAAGCCTCAGCGGCGGAAGAACCCTCAG
GAAGGCCTGTATAACGAACTGCAGAAAGACAAGATGGCCGAGGCCTAC
AGCGAGATCGGCATGAAGGGCGAGCGGCGGAGAGGCAAGGGCCACGAT
GGCCTGTAC.
```

Particularly preferred nucleic acids include those comprising or encoding any of the constituents of the CAR depicted in FIG. 9, including signal sequence, CD19 ScFv, CD8 hinge, transmembrane domain, 4-1BB, and/or CD3z sequences. Other preferred nucleic acids include those comprising or encoding any of the constituents of the CARs of SEQ ID NOs:45-50.

In some embodiments, the nucleic acid comprises a hook operably-linked to a promoter, preferably UBC or β2M, and a CAR comprising a hook-binding protein, operably-linked to an IRES. In a preferred embodiment, the hook is a streptavidin protein, preferably core Streptavidin, and the hook-binding protein is a streptavidin-binding protein.

Vectors

The invention encompasses vectors encoding a CAR and a hook-binding domain. Preferred vectors comprise a nucleic acid sequence or encode an amino acid sequence of at least one of the SEQ ID NOs detailed herein.

The vector can further encode a "hook." A "hook" is a protein that prevents a CAR containing a hook-binding domain from exiting the endoplasmic reticulum (ER) or Golgi by reversibly binding, directly or indirectly, the hook-binding domain within the CAR.

The retention can take place in the lumen of the ER or at its cytoplasmic face, depending on the topology of the protein and the orientation of tagging with the interaction domains. Boncompain et al., Current Protocols in Cell Biology 15.19.1-15.19.16, December 2012, which is hereby incorporated by reference.

In some embodiments, the hook for the ER comprises a mutant of stromal interaction molecule 1 (STIM1-NN; a type I protein) that localizes in the ER but that cannot bind microtubules, an isoform of the human invariant chain of the major histocompatibility complex (Ii; a type II protein) that has an N-terminal arginine-based motif; or a C-terminal ER retention signal (Lys-Asp-Glu-Leu; KDEL). Boncompain et al., Nat. Methods 9:493-498, 2012, which is hereby incorporated by reference. The hook can be fused to a core Streptavidin in their luminal or cytoplasmic domain depending on the hook-binding protein. Id. at FIG. 1.

In an alternative embodiment, the hook for the Golgi can be Golgin-84 to be used as a cytoplasmic Golgi hook. Id.

Preferably, the hook comprises a Streptavidin protein sequence, most preferably core Streptavidin. U.S. Pat. No. 5,672,691, which is hereby incorporated by reference.

Preferably, the hook comprises one of the following Streptavidin protein sequences:

```
                                           (SEQ ID NO: 31)
MDPSKDSKAQVSAAEAGITGTWYNQLGSTFIVTAGADGALTGTYESAV

GNAESRYVLTGRYDSAPATDGSGTALGWTVAWKNNYRNAHSATTWSGQ

YVGGAEARINTQWLLTSGTTEANAWKSTLVGHDTFTKVKPSAASIDAA

KKAGVNNGNPLDAVQQ
or
                                           (SEQ ID NO: 32)
MDPSKDSKAQVSAAEAGITGTWYNQLGSTFIVTAGADGALTGTYESAV

GNAESRYTLTGRYDSAPATDGSGTALGWRVAWKNNYRNAHSATTWSGQ

YVGGAEARINTQWTLTSGTTEANAWKSTLRGHDTFTKVKPSAASIDAA

KKAGVNNGNPLDAVQQ
or
                                           (SEQ ID NO: 42)
MHRRRSRSCREDQKPVTGDPSKDSKAQVSAAEAGITGTWYNQLGSTFI

VTAGADGALTGTYESAVGNAESRYVLTGRYDSAPATDGSGTALGWTVA

WKNNYRNAHSATTWSGQYVGGAEARINTQWLLTSGTTEANAWKSTLVG

HDTFTKVKPSAASIDAAKKAGVNNGNPLDAVQQVDYPYDVPDYAVGPM

DDQRDLISNNEQLPMLGRRPGAPESKCSRGALYTGFSILVTLLLAGQA
```

```
TTAYFLYQQQGRLDKLTVTSQNLQLENLRMKLPKPPKPVSKMRMATPL

LMQALPMGALPQGPMQNATKYGNMTEDHVMHLLQNADPLKVYPPLKGS

FPENLRHLKNTMETIDWKVFESWMHHWLLFEMSRHSLEQKPTDAPPKE

SLELEDPSSGLGVTKQDLGPVPM.
```

Preferably, the hook is encoded by the following nucleotide sequence:

```
                                           (SEQ ID NO: 43)
ATGCACCGGAGGAGATCACGCTCTTGTAGGGAGGACCAGAAACCTGTC

ACCGGTGACCCTAGCAAAGACTCAAAAGCTCAGGTGTCCGCTGCCGAG

GCTGGCATTACTGGAACATGGTACAATCAGCTCGGGAGCACCTTTATT

GTGACTGCTGGAGCCGATGGAGCCCTCACCGGAACATACGAATCTGCT

GTGGGAAACGCCGAATCACGGTACGTCCTCACTGGCCGATACGATAGT

GCCCCTGCCACCGACGGATCTGGGACTGCCCTGGGATGGACTGTCGCT

TGGAAAAACAACTACCGGAATGCTCATTCTGCCACAACATGGAGTGGA

CAGTACGTGGGAGGCGCTGAGGCTAGAATCAATACACAGTGGCTGCTC

ACATCTGGCACAACCGAGGCAAATGCTTGGAAATCCACCCTGGTGGGA

CATGACACATTCACCAAAGTGAAACCCTCCGCCGCTTCAATCGATGCC

GCCAAAAAAGCCGGAGTCAACAACGGCAATCCTCTGGATGCCGTCCAG

CAGGTCGACTATCCGTACGACGTACCAGACTACGCAGTCGGACCGATG

GACGATCAGAGGGACCTCATTAGCAACAACGAACAGCTGCCTATGCTG

GGACGGCGACCTGGAGCCCCTGAATCCAAATGCTCTAGGGGAGCACTG

TACACTGGCTTCTCCATTCTCGTGACACTGCTGCTGGCCGGGCAGGCT

ACTACTGCTTACTTCCTGTACCAGCAGCAGGGGCGGCTGGACAAACTC

ACTGTGACATCTCAGAACCTCCAGCTGGAAAATCTGAGGATGAAACTG

CCCAAACCCCCTAAACCCGTGTCCAAAATGAGGATGGCCACACCTCTG

CTCATGCAGGCACTGCCAATGGGAGCCCTGCCCCAGGGGCCCATGCAG

AATGCCACCAAGTATGGCAACATGACAGAGGACCATGTGATGCACCTG

CTCCAGAATGCTGACCCCCTGAAGGTGTACCCGCCACTGAAGGGGAGC

TTCCCGGAGAACCTGAGACACCTTAAGAACACCATGGAGACCATAGAC

TGGAAGGTCTTTGAGAGCTGGATGCACCATTGGCTCCTGTTTGAAATG

AGCAGGCACTCCTTGGAGCAAAAGCCCACTGACGCTCCACCGAAAGAG

TCACTGGAACTGGAGGACCCGTCTTCTGGGCTGGGTGTGACCAAGCAG

GATCTGGGCCCAGTCCCCATGTGA.
```

In some embodiments, the glycine at aa 49 of SEQ ID NO:31 or SEQ ID NO:32 is replaced with a bulkier residue (e.g., threonine) to reduces the biotin binding affinity without affecting the SBP binding affinity. Wu et al., PLoS ONE 8(7): e69530 (2013), which is hereby incorporated by reference. Another mutation can also be introduced to further favor SBP binding over biotin (mutation S27A).

In some embodiments, the vector comprises a hook operably-linked to a promoter, preferably UBC or β2M, and a CAR comprising a hook-binding protein, operably-linked to an IRES.

A preferred IRES nucleotide sequence is:

(SEQ ID NO: 44)
GCCCCTCTCCCTCCCCCCCCCCTAACGTTACTGGCCGAAGCCGCTTGG
AATAAGGCCGGTGTGCGTTTGTCTATATGTTATTTTCCACCATATTGC
CGTCTTTTGGCAATGTGAGGGCCCGGAAACCTGGCCCTGTCTTCTTGA
CGAGCATTCCTAGGGGTCTTTCCCCTCTCGCCAAAGGAATGCAAGGTC
TGTTGAATGTCGTGAAGGAAGCAGTTCCTCTGGAAGCTTCTTGAAGAC
AAACAACGTCTGTAGCGACCCTTTGCAGGCAGCGGAACCCCCCACCTG
GCGACAGGTGCCTCTGCGGCCAAAAGCCACGTGTATAAGATACACCTG
CAAAGGCGGCACAACCCCAGTGCCACGTTGTGAGTTGGATAGTTGTGG
AAAGAGTCAAATGGCTCTCCTCAAGCGTATTCAACAAGGGGCTGAAGG
ATGCCCAGAAGGTACGCCATTGTATGGGATCTGATCTGGGGCCTCGGT
GCACATGCTTTACATGTGTTTAGTCGAGGTTAAAAAACGTCTAGGCCC
CCCGAACCACGGGGACGTGGTTTTCCTTTGAAAAACACGATGATAA.

In a preferred embodiment, the hook is a streptavidin protein, preferably core Streptavidin, and the hook-binding protein is a streptavidin-binding protein. Preferred vectors are lentivectors comprising any of the following nucleotide or amino acid sequences:

CAR-CD19 2nd generation-SBP1 (nt):

(SEQ ID NO: 45)
ATGGCCCTGCCTGTGACAGCCCTGCTGCTGCCCCTGGCTCTCCTGCTG
CATGCCGCCAGACCCGCTAGCGACATCCAGATGACCCAGACCACCAGC
AGCCTGAGCGCCAGCCTGGGCGACAGAGTGACCATCAGCTGCCGGGCC
AGCCAGGACATCAGCAAGTACCTGAACTGGTATCAGCAGAAACCCGAC
GGCACCGTGAAGCTGCTGATCTACCACACCAGCCGGCTCCACAGCGGC
GTGCCCAGCAGATTTTCTGGCAGCGGCAGCGGCACCGACTACAGCCTG
ACCATCTCCAACCTGGAACAGGAAGATATCGCTACCTACTTCTGTCAG
CAAGGCAACACCCTGCCCTACACCTTCGGCGGAGGCACCAAGCTGGAA
ATCACCGGCGGAGGCGGAAGTGGAGGTGGAGGATCTGGCGGCGGAGGC
TCCGAAGTGAAGCTGCAGGAAAGCGGCCCTGGCCTCGTGGCCCCTAGC
CAGAGCCTGTCCGTGACCTGTACCGTGTCCGGCGTGTCCCTGCCCGAC
TACGGCGTGTCCTGGATCAGACAGCCTCCCAGAAAGGGCCTGGAATGG
CTGGGCGTGATCTGGGGCAGCGAGACAACCTACTACAACAGCGCCCTG
AAGTCCCGGCTGACCATCATCAAGGACAACAGCAAGAGCCAGGTGTTC
CTGAAGATGAACAGCCTGCAGACCGACGACACCGCCATCTACTACTGC
GCCAAGCACTACTACTACGGCGGCAGCTACGCCATGGACTACTGGGGC
CAGGGCACCAGCGTGACCGTGTCCAGCCATATGGCCCTGAGCAACAGC
ATCATGTACTTCAGCCACTTCGTGCCCGTGTTTCTGCCCGCCAAGCCC
ACCACCACCCCTGCCCCTAGACCTCCCACCCCAGCCCCAACAATCGCC
AGCCAGCCTCTGTCCCTGCGGCCCGAAGCCTGTAGACCTGCTGCCGGC
GGAGCCGTGCACACCAGAGGCCTGGATATCTACATCTGGGCCCCTCTG
GCCGGCACCTGTGGCGTGCTGCTGCTGAGCCTGGTGATCACCACCGGT

ATGGACGAGAAAACCACCGGCTGGCGGGGAGGCCACGTGGTGGAAGGA
CTGGCCGGCGAGCTGGAACAGCTGCGGGCCAGACTGGAACACCACCCC
CAGGGCCAGAGAGAGCCCAAGCGGGGCAGAAAGAAGCTGCTGTACATC
TTCAAGCAGCCCTTCATGCGGCCCGTGCAGACCACCCAGGAAGAGGAC
GGCTGCAGCTGCCGGTTCCCCGAGGAAGAGGAAGGCGGCTGCGAACTG
CCCAAGCTGTGCTACCTGCTGGACGGCATCCTGTTCATCTACGGCGTG
ATCCTGACCGCCCTGTTCCTGAGAGTGAAGTTCAGCAGAAGCGCCGAC
GCCCCTGCCTACCAGCAGGGCCAGAACCAGCTGTACAACGAGCTGAAC
CTGGGCAGACGGGAAGAGTACGACGTGCTGGACAAGCGGAGAGGCCGG
GACCCTGAGATGGCGGCAAGCCCCAGCGGCGGAAGAACCCCCAGGAA
GGCCTGTATAACGAACTGCAGAAAGACAAGATGGCCGAGGCCTACAGC
GAGATCGGCATGAAGGGCGAGCGGCGGAGAGGCAAGGGCCACGATGGC
CTGTAC.

CAR-CD19 2nd generation-SBP1 (aa):

(SEQ ID NO: 46)
MALPVTALLLPLALLLHAARPASDIQMTQTTSSLSASLGDRVTISCRA
SQDISKYLNWYQQKPDGTVKLLIYHTSRLHSGVPSRFSGSGSGTDYSL
TISNLEQEDIATYFCQQGNTLPYTFGGGTKLEITGGGSGGGSGGGG
SEVKLQESGPGLVAPSQSLSVTCTVSGVSLPDYGVSWIRQPPRKGLEW
LGVIWGSETTYYNSALKSRLTIIKDNSKSQVFLKMNSLQTDDTAIYYC
AKHYYYGGSYAMDYWGQGTSVTVSSHMALSNSIMYFSHFVPVFLPAKP
TTTPAPRPPTPAPTIASQPLSLRPEACRPAAGGAVHTRGLDIYIWAPL
AGTCGVLLLSLVITTGMDEKTTGWRGGHVVEGLAGELEQLRARLEHHP
QGQREPKRGRKKLLYIFKQPFMRPVQTTQEEDGCSCRFPEEEEGGCEL
PKLCYLLDGILFIYGVILTALFLRVKFSRSADAPAYQQGQNQLYNELN
LGRREEYDVLDKRRGRDPEMGGKPQRRKNPQEGLYNELQKDKMAEAYS
EIGMKGERRRGKGHDGLY.

CAR-CD19 2nd generation-SBP2(nt):

(SEQ ID NO: 47)
ATGGCCCTGCCTGTGACAGCCCTGCTGCTGCCCCTGGCTCTCCTGCTG
CATGCCGCCAGACCCGCTAGCGACATCCAGATGACCCAGACCACCAGC
AGCCTGAGCGCCAGCCTGGGCGACAGAGTGACCATCAGCTGCCGGGCC
AGCCAGGACATCAGCAAGTACCTGAACTGGTATCAGCAGAAACCCGAC
GGCACCGTGAAGCTGCTGATCTACCACACCAGCCGGCTCCACAGCGGC
GTGCCCAGCAGATTTTCTGGCAGCGGCAGCGGCACCGACTACAGCCTG
ACCATCTCCAACCTGGAACAGGAAGATATCGCTACCTACTTCTGTCAG
CAAGGCAACACCCTGCCCTACACCTTCGGCGGAGGCACCAAGCTGGAA
ATCACCGGCGGAGGCGGAAGTGGAGGTGGAGGATCTGGCGGCGGAGGC
TCCGAAGTGAAGCTGCAGGAAAGCGGCCCTGGCCTCGTGGCCCCTAGC
CAGAGCCTGTCCGTGACCTGTACCGTGTCCGGCGTGTCCCTGCCCGAC

-continued

```
TACGGCGTGTCCTGGATCAGACAGCCTCCCAGAAAGGGCCTGGAATGG
CTGGGCGTGATCTGGGGCAGCGAGACAACCTACTACAACAGCGCCCTG
AAGTCCCGGCTGACCATCATCAAGGACAACAGCAAGAGCCAGGTGTTC
CTGAAGATGAACAGCCTGCAGACCGACGACACCGCCATCTACTACTGC
GCCAAGCACTACTACTACGGCGGCAGCTACGCCATGGACTACTGGGGC
CAGGGCACCAGCGTGACCGTGTCCAGCCATATGGCCCTGAGCAACAGC
ATCATGTACTTCAGCCACTTCGTGCCCGTGTTTCTGCCCGCCAAGCCC
ACCACCACCCCTGCCCCTAGACCTCCCACCCCAGCCCCAACAATCGCC
AGCCAGCCTCTGTCCCTGCGGCCCGAAGCCTGTAGACCTGCTGCCGGC
GGAGCCGTGCACACCAGAGGCCTGGATATCTACATCTGGGCCCCTCTG
GCCGGCACCTGTGGCGTGCTGCTGCTGAGCCTGGTGATCACAAAGCGG
GGCAGAAAGAAGCTGCTGTACATCTTCAAGCAGCCCTTCATGCGGCCC
GTGCAGACCACCCAGGAAGAGGACGGCTGCAGCTGCCGGTTCCCCGAG
GAAGAGGAAGGCGGCTGCGAGCTGACCGGTATGGACGAGAAAACCACC
GGCTGGCGGGGAGGCCACGTGGTGGAAGGACTGGCCGGCGAGCTGGAA
CAGCTGCGGGCCAGACTGGAACACCACCCCAGGGCCAGAGGGAACCC
CCCAAGCTGTGCTACCTGCTGGACGGCATCCTGTTCATCTACGGCGTG
ATCCTGACCGCCCTGTTCCTGAGAGTGAAGTTCAGCAGAAGCGCCGAC
GCCCCTGCCTACCAGCAGGGCCAGAACCAGCTGTACAACGAGCTGAAC
CTGGGCAGACGGGAAGAGTACGACGTGCTGGACAAGCGGAGAGGCCGG
GACCCTGAGATGGGCGGCAAGCCCCAGCGGCGGAAGAACCCCCAGGAA
GGCCTGTATAACGAACTGCAGAAAGACAAGATGGCCGAGGCCTACAGC
GAGATCGGCATGAAGGGCGAGCGGCGGAGAGGCAAGGGCCACGATGGC
CTGTAC.
```

CAR-CD19 2nd generation-SBP2(aa):

```
                                         (SEQ ID NO: 48)
MALPVTALLLPLALLLHAARPASDIQMTQTTSSLSASLGDRVTISCRA
SQDISKYLNWYQQKPDGTVKLLIYHTSRLHSGVPSRFSGSGSGTDYSL
TISNLEQEDIATYFCQQGNTLPYTFGGGTKLEITGGGGSGGGGSGGGG
SEVKLQESGPGLVAPSQSLSVTCTVSGVSLPDYGVSWIRQPPRKGLEW
LGVIWGSETTYYNSALKSRLTIIKDNSKSQVFLKMNSLQTDDTAIYYC
AKHYYYGGSYAMDYWGQGTSVTVSSHMALSNSIMYFSHFVPVFLPAKP
TTTPAPRPPTPAPTIASQPLSLRPEACRPAAGGAVHTRGLDIYIWAPL
AGTCGVLLLSLVITKRGRKKLLYIFKQPFMRPVQTTQEEDGCSCRFPE
EEEGGCELTGMDEKTTGWRGGHVVEGLAGELEQLRARLEHHPQGQREP
PKLCYLLDGILFIYGVILTALFLRVKFSRSADAPAYQQGQNQLYNELN
LGRREEYDVLDKRRGRDPEMGGKPQRRKNPQEGLYNELQKDKMAEAYS
EIGMKGERRRGKGHDGLY.
```

CAR-CD19 2nd generation-SBP3(nt):

```
                                         (SEQ ID NO: 49)
ATGGCCCTGCCTGTGACAGCCCTGCTGCTGCCCCTGGCTCTCCTGCTG
CATGCCGCCAGACCCGCTAGCGACATCCAGATGACCCAGACCACCAGC
AGCCTGAGCGCCAGCCTGGGCGACAGAGTGACCATCAGCTGCCGGGCC
AGCCAGGACATCAGCAAGTACCTGAACTGGTATCAGCAGAAACCCGAC
GGCACCGTGAAGCTGCTGATCTACCACACCAGCCGGCTCCACAGCGGC
GTGCCCAGCAGATTTTCTGGCAGCGGCAGCGGCACCGACTACAGCCTG
ACCATCTCCAACCTGGAACAGGAAGATATCGCTACCTACTTCTGTCAG
CAAGGCAACACCCTGCCCTACACCTTCGGCGGAGGCACCAAGCTGGAA
ATCACCGGCGGAGGCGGAAGTGGAGGTGGAGGATCTGGCGGCGGAGGC
TCCGAAGTGAAGCTGCAGGAAAGCGGCCCTGGCCTCGTGGCCCCTAGC
CAGAGCCTGTCCGTGACCTGTACCGTGTCCGGCGTGTCCCTGCCCGAC
TACGGCGTGTCCTGGATCAGACAGCCTCCCAGAAAGGGCCTGGAATGG
CTGGGCGTGATCTGGGGCAGCGAGACAACCTACTACAACAGCGCCCTG
AAGTCCCGGCTGACCATCATCAAGGACAACAGCAAGAGCCAGGTGTTC
CTGAAGATGAACAGCCTGCAGACCGACGACACCGCCATCTACTACTGC
GCCAAGCACTACTACTACGGCGGCAGCTACGCCATGGACTACTGGGGC
CAGGGCACCAGCGTGACCGTGTCCAGCCATATGGCCCTGAGCAACAGC
ATCATGTACTTCAGCCACTTCGTGCCCGTGTTTCTGCCCGCCAAGCCC
ACCACCACCCCTGCCCCTAGACCTCCCACCCCAGCCCCAACAATCGCC
AGCCAGCCTCTGTCCCTGCGGCCCGAAGCCTGTAGACCTGCTGCCGGC
GGAGCCGTGCACACCAGAGGCCTGGATATCTACATCTGGGCCCCTCTG
GCCGGCACCTGTGGCGTGCTGCTGCTGAGCCTGGTGATCACAAAGCGG
GGCAGAAAGAAGCTGCTGTACATCTTCAAGCAGCCCTTCATGCGGCCC
GTGCAGACCACCCAGGAAGAGGACGGCTGCAGCTGCCGGTTCCCCGAG
GAAGAGGAAGGCGGCTGCGAACTGCCCAAGCTGTGCTACCTGCTGGAC
GGCATCCTGTTCATCTACGGCGTGATCCTGACCGCCCTGTTCCTGAGA
GTGAAGTTCAGCAGAAGCGCCGACGCCCCTGCCTACCAGCAGGGCCAG
AACCAGCTGTACAACGAGCTGAACCTGGGCAGACGGGAAGAGTACGAC
GTGCTGGACAAGCGGAGAGGCCGGGACCCTGAGATGGGCGGCAAGCCC
CAGCGGCGGAAGAACCCCCAGGAAGGCCTGTATAACGAACTGCAGAAA
GACAAGATGGCCGAGGCCTACAGCGAGATCGGCATGAAGGGCGAGCGG
CGGAGAGGCAAGGGCCACGATGGCCTGTACACCGGTATGGACGAGAAA
ACCACCGGCTGGCGGGGAGGCCACGTGGTGGAAGGACTGGCCGGCGAG
CTGGAACAGCTGCGGGCCAGACTGGAACACCACCCCAGGGCCAGAGG
GAACCC.
```

CAR-CD19 2nd generation-SBP3(aa):

```
                                         (SEQ ID NO: 50)
MALPVTALLLPLALLLHAARPASDIQMTQTTSSLSASLGDRVTISCRA
SQDISKYLNWYQQKPDGTVKLLIYHTSRLHSGVPSRFSGSGSGTDYSL
```

-continued

```
TISNLEQEDIATYFCQQGNTLPYTFGGGTKLEITGGGGSGGGGSGGGG

SEVKLQESGPGLVAPSQSLSVTCTVSGVSLPDYGVSWIRQPPRKGLEW

LGVIWGSETTYYNSALKSRLTIIKDNSKSQVFLKMNSLQTDDTAIYYC

AKHYYYGGSYAMDYWGQGTSVTVSSHMALSNSIMYFSHFVPVFLPAKP

TTTPAPRPPTPAPTIASQPLSLRPEACRPAAGGAVHTRGLDIYIWAPL

AGTCGVLLLSLVITKRGRKKLLYIFKQPFMRPVQTTQEEDGCSCRFPE

EEEGGCELPKLCYLLDGILFIYGVILTALFLRVKFSRSADAPAYQQGQ

NQLYNELNLGRREEYDVLDKRRGRDPEMGGKPQRRKNPQEGLYNELQK

DKMAEAYSEIGMKGERRRGKGHDGLYTGMDEKTTGWRGGHVVEGLAGE

LEQLRARLEHHPQGQREP.
```

The vector can be an expression vector. The vector can be a plasmid vector. Preferably, the vector is a lentiviral vector.

Within the context of this invention, a "lentiviral vector" means a non-replicating vector for the transduction of a host cell with a transgene comprising cis-acting lentiviral RNA or DNA sequences, and requiring lentiviral proteins (e.g., Gag, Pol, and/or Env) that are provided in trans. The lentiviral vector lacks expression of functional Gag, Pol, and Env proteins. The lentiviral vector may be present in the form of an RNA or DNA molecule, depending on the stage of production or development of said retroviral vectors.

The lentiviral vector can be in the form of a recombinant DNA molecule, such as a plasmid. The lentiviral vector can be in the form of a lentiviral vector particle, such as an RNA molecule(s) within a complex of lentiviral and other proteins. Typically, lentiviral particle vectors, which correspond to modified or recombinant lentivirus particles, comprise a genome which is composed of two copies of single-stranded RNA. These RNA sequences can be obtained by transcription from a double-stranded DNA sequence inserted into a host cell genome (proviral vector DNA) or can be obtained from the transient expression of plasmid DNA (plasmid vector DNA) in a transformed host cell.

Preferably the lentiviral vector particles have the capacity for integration. As such, they contain a functional integrase protein. Non-integrating vector particles have one or more mutations that eliminate most or all of the integrating capacity of the lentiviral vector particles. For, example, a non-integrating vector particle can contain mutation(s) in the integrase encoded by the lentiviral pol gene that cause a reduction in integrating capacity. In contrast, an integrating vector particle comprises a functional integrase protein that does not contain any mutations that eliminate most or all of the integrating capacity of the lentiviral vector particles.

Lentiviral vectors derive from lentiviruses, in particular human immunodeficiency virus (HIV-1 or HIV-2), simian immunodeficiency virus (SIV), equine infectious encephalitis virus (EIAV), caprine arthritis encephalitis virus (CAEV), bovine immunodeficiency virus (BIV) and feline immunodeficiency virus (FIV), which are modified to remove genetic determinants involved in pathogenicity and introduce new determinants useful for obtaining therapeutic effects.

Such vectors are based on the separation of the cis- and trans-acting sequences. In order to generate replication-defective vectors, the trans-acting sequences (e.g., gag, pol, tat, rev, and env genes) can be deleted and replaced by an expression cassette encoding a transgene.

Efficient integration and replication in non-dividing cells generally requires the presence of two cis-acting sequences at the center of the lentiviral genome, the central polypurine tract (cPPT) and the central termination sequence (CTS). These lead to the formation of a triple-stranded DNA structure called the central DNA "flap", which acts as a signal for uncoating of the pre-integration complex at the nuclear pore and efficient importation of the expression cassette into the nucleus of non-dividing cells, such as dendritic cells.

In one embodiment, the invention encompasses a lentiviral vector comprising a central polypurine tract and central termination sequence referred to as cPPT/CTS sequence as described, in particular, in the European patent application EP 2 169 073.

Further sequences are usually present in cis, such as the long terminal repeats (LTRs) that are involved in integration of the vector proviral DNA sequence into a host cell genome. Vectors may be obtained by mutating the LTR sequences, for instance, in domain U3 of said LTR (ΔU3) (Miyoshi H et al, 1998, *J Virol.* 72(10):8150-7; Zufferey et al., 1998, *J Virol* 72(12):9873-80).

Preferably, the vector does not contain an enhancer. In one embodiment, the invention encompasses a lentiviral vector comprising LTR sequences, preferably with a mutated U3 region (ΔU3) removing promoter and enhancer sequences in the 3' LTR.

The packaging sequence ψ (psi) can also be incorporated to help the encapsidation of the polynucleotide sequence into the vector particles (Kessler et al., 2007, *Leukemia*, 21(9):1859-74; Paschen et al., 2004, *Cancer Immunol Immunother* 12(6):196-203).

In one embodiment, the invention encompasses a lentiviral vector comprising a lentiviral packaging sequence ψ (psi).

Further additional functional sequences, such as a transport RNA-binding site or primer binding site (PBS) or a Woodchuck PostTranscriptional Regulatory Element (WPRE), can also be advantageously included in the lentiviral vector polynucleotide sequence of the present invention, to obtain a more stable expression of the transgene in vivo.

In one embodiment, the invention encompasses a lentiviral vector comprising a PBS. In one embodiment, the invention encompasses a lentiviral vector comprising a WPRE and/or an IRES.

Thus, in a preferred embodiment, the lentiviral vector comprises at least one cPPT/CTS sequence, one ψ sequence, one (preferably 2) LTR sequence, and an expression cassette including a transgene under the transcriptional control of a β2m or class I MHC promoter.

Promoter

The invention encompasses the use of promoters to drive high expression of CARs from lentivectors in T cells, preferably human T cells. Preferred promoters are human ubiquitin, MHC class I, MHC class II, and β2 microglobulin (β2m) promoters.

In various embodiments, the promoter drives high expression in antigen presenting cells, including dendritic cells. Preferably, the promoter lacks an enhancer element to avoid insertional effects.

Most preferably, the promoter is not a CMV promoter/enhancer. Preferably, the promoter is not a dectin-2 or MHCII promoter.

The sequences of various mammalian (human) MHC class I promoters are shown below:

HLA-A2 (MHC I):

(SEQ ID NO: 9)
attgggagtcccagccttggggattccccaactccgcagttctttt ctccctctcccaacctatgtagggtccttcttcctggatactcacgac gcggacccagttctcactcccattgggtgtcgggtttccagagaagcc aatcagtgtcgtcgcggtcgcggttctaaagtccgcacgcacccaccg ggactcagattctccccagacgccgagg

HLA-B7 (MHC I):

(SEQ ID NO: 10)
ggggaggcgcagcgttggggattccccactcccctgagtttcacttct tctcccaacttgtgtcgggtccttcttccaggatactcgtgacgcgtc cccacttcccactcccattgggtattggatatctagagaagccaatca gcgtcgccgcggtcccagttctaaagtccccacgcacccacccggact cagag HLA-Cw5 (MHC I):

(SEQ ID NO: 11)
cactggggaggcgccgcgttgaggattctccactcccctcagtttcac ttcttctcccaacctgcgtcgggtccttcttcctgaatactcatgacg cgtcccaattcccactcccattgggtgtcgggttctagagaagccaa tcagcgtctccgcagtcccggtctaaagtcccagtcacccacccgga ctcagattctccccagacgccgag

HLA-E (MHC I):

(SEQ ID NO: 12)
taagaactgctgattgctgggaaactctgcagtttcccgttcctctcg taacctggtcatgtgtccttcttcctggatactcatgacgcagactca gttctcattcccaatgggtgtcgggtttctagagaagccaatcagcgt cgccacgactcccgactataaagtccccatccggactcaagaagttct caggactcagagg

HLA-F (MHC I):

(SEQ ID NO: 13)
aggccccgaggcggtgtctgggggttggaaggctcagtattgagaattc cccatctccccagagtttctctttctctcccaacccgtgtcaggtcct tcatcctggatactcataacgcggcccatttctcactcccattggc gtcgcgtttctagagaagccaatcagtgtcgccgcagttcccaggttc taaagtcccacgcacccgcgggactcatatttttcccagacgcggag gttggggtcatg A sequence of the human β2-microglobulin promoter is shown below:

(SEQ ID NO: 14)
aacatcacgagactctaagaaaaggaaactgaaaacgggaaagtccct ctctctaacctggcactgcgtcgctggcttggagacaggtgacggtcc ctgcgggccttgtcctgattggctgggcacgcgtttaatataagtgga ggcgtcgcgctggcgggcattcctgaagctgacagcattcgggccgag.

A sequence of the human ubiquitin (Ubi) promoter is shown below:

(SEQ ID NO: 38)
ggcctccgcgccgggttttgggcctcccgcgggcgcccccctcctcac ggcgagcgctgccacgtcagacgaagggcgcagcgagcgtcctgatcc ttccgcccggacgctcaggacagcggcccgctgctcataagactcggc cttagaaccccagtatcagcagaaggacattttaggacgggacttggg tgactctagggcactggttttctttccagagagcggaacaggcgagga aaagtagtcccttctcggcgattctgcggagggatctccgtgggggcgg tgaacgccgatgattatataaggacgcgccgggtgtggcacagctagt tccgtcgcagccgggatttgggtcgcggttcttgtttgtggatcgctg tgatcgtcacttggtgagtagcgggctgctgggctggccggggctttc gtggccgccgggccgctcggtgggacggaagcgtgtggagagaccgcc aagggctgtagtctgggtccgcgagcaaggttgccctgaactgggggt tgggggagcgcagcaaaatggcggctgttcccgagtcttgaatgaa gacgcttgtgaggcgggctgtgaggtcgttgaaacaaggtggggggca tggtgggcggcaagaacccaaggtcttgaggccttcgctaatgcggga aagctcttattcgggtgagatgggctggggcaccatctggggaccctg acgtgaagtttgtcactgactggagaactcggttttgtcgtctgttgcg ggggcggcagttatggcggtgccgttgggcagtgcacccgtacctttg ggagcgcgcgcccgtcgtgtcgtgacgtcacccgttctgttggctt ataatgcagggtggggccacctgccggtaggtgtgcggtaggcttttc tccgtcgcaggacgcagggttcgggcctagggtaggctctcctgaatc gacaggcgccggacctctggtgaggggagggataagtgaggcgtcagt ttctttggtcggttttatgtacctatcttcttaagtagctgaagctcc ggttttgaactatgcgctcggggttggcgagtgtgttttgtgaagttt tttaggcaccttttgaaatgtaatcatttgggtcaatatgtaatttc agtgttagactagtaaattgtccgctaaattctggccgtttttggctt ttttgttagaccgatc.

A sequence of the human HLA-DRα promoter is shown below:

(SEQ ID NO: 41)
gtctagaagtcagattgggggttaaagagtctgtccgtgattgactaac agtcttaaatacttgatttgttgttgttgttgtcctgtttgtttaaga actttacttctttatccaatgaacggagtatcttgtgtcctggaccct ttgcaagaaccctttcccctagcaacagatgcgtcatctcaaaatattt ttctgattggccaaagagtaattgatttgcattttaatggtcagactc tattacaccccacattctcttttcttttattcttgtctgttctgcctc actcccgagctc.

In various embodiments, the lentiviral vector comprises a β2m, Ubi, MHCII, or MHC class I promoter. Preferably, the MHC class I promoter is an HLA-A2 promoter, an HLA-B7 promoter, an HLA-Cw5 promoter, an HLA-F, or an HLA-E promoter. In various embodiments, the promoter sequence comprises a polynucleotide sequence that shares more than 90%, preferably more than 95%, more preferably more than 99% identity with the promoter sequence of SEQ ID NO:9, SEQ ID NO:10, SEQ ID NO:11, SEQ ID NO:12, SEQ ID NO:13, SEQ ID NO:14, SEQ ID NO:38, or SEQ ID NO:41.

In some embodiments, the expression of the promoter in BDCA+ dendritic cells is at least 10, 12, 15, 20, 25, 30, 35, 40, 50, or 60 times the expression of that promoter in skeletal muscle cells.

In one embodiment, the invention encompasses lentiviral vector particles comprising a lentiviral vector that comprises a dendritic cell-specific promoter directing expression of a microbial or tumor antigen, wherein the lentiviral vector particles exhibit higher expression of the antigen in BDCM cells than in HEK 293 T cells.

The invention encompasses lentiviral vectors containing a promoter that does not contain an enhancer.

The invention encompasses the insertion of an MHC Class I (MHCI), Ubi, EF1α, or β2 microglobulin promoter (β2m) promoter into a lentiviral vector. As used herein, an "MHC Class I (MHCI) promoter" or "β2 microglobulin promoter" or "MHC Class II (MHCII)" or "human ubiquitin promoter" includes a naturally occurring or synthetic MHC Class I promoter or β2 microglobulin promoter or MHC Class II promoter or human ubiquitin promoter. The term "MHC Class I promoter" does not include a β2m promoter.

In one embodiment, the lentiviral vector particles comprising the promoter exhibit higher expression in BDCM cells than in HEK 293 T cells.

The promoter can be a naturally occurring promoter. Examples of naturally occurring promoters are the human 62m, HLA-A2, HLA-B7, HLA-Cw5, HLA-E, HLA-F, HLA-DRα, and ubiquitin gene promoters.

These naturally occurring MHCI promoters are generally cloned or reproduced from the promoter region of a gene encoding the MHC class I protein, or referred to as putatively encoding such proteins in genome databases (ex: NCBI polynucleotide database http://www.ncbi.nlm.nih.gov/guide/dna-rna). Both β2m and class I MHC proteins enter the Major Histocompatibility Complex (MHC).

The proteins encoded by these genes are found in almost all cell types. MHCI proteins are generally present at the surface of the membrane of leucocytes, where they are associated with the β2-microglobulin (β2m). The role of these associated proteins is to present peptides from endogenous sources to CD8+ T cells. They thus play a central role to the generation of the antigen-specific immune response. Because MHC class I proteins have been widely studied and described for many years, their genes are well characterized and detectable using sequence comparison tools, such as the BLAST method (Altschul, S. F. et al. (1990). Basic local alignment search tool. *J. Mol. Biol.* 215(3):403-410).

MHC class I promoters share the ability to be strongly activated in antigen presenting cells, including dendritic cells, as well as, to lower intensity, in the majority of the other human body tissues.

The promoters of the invention can contain further regulatory elements, such as one or more Sp1 and ETs binding sites. In a preferred embodiment, the MHC class I promoter contains 2 Sp1 binding sites and 1 Ets binding site. In other embodiments, Ap1 and/or Ap2 sites are further contained in the promoter.

Preferred promoters are naturally occurring human β2m, HLA-A2, HLA-B7, HLA-Cw5, HLA-E and HLA-F promoters.

Promoters can also be synthetic. Synthetic promoters include promoters that are synthesized using molecular biological techniques to assemble the individual components of a promoter or that are derived from naturally occurring promoters using molecular biological techniques.

In various embodiments, the synthetic promoter comprises a polynucleotide sequence that shares more than 90%, preferably more than 95%, more preferably more than 99% identity, or 100% with the promoter sequence of a β2m, Ubi, MHC class II, or MHC class I gene promoter (e.g., SEQ ID NOs: 9-14, 38, or 41).

The transcription of MHC class genes are usually mediated by two major regulatory elements: Interferon stimulated response element (ISRE) and the SXY module (encompassing the W/S, X1X2/Site α and Y/enhancer B regulatory elements). See Van den Elsen, Immunogenetics (1998) 48:208-211.

These regulatory promoter elements are localized in a region extending approximately from nucleotides −220 to −95 upstream of the transcription initiation site. They mediate tissue-specific and cytokine-induced transcription of MHC class I genes.

The ISRE of MHC class I gene promoters generally contains binding sites for interferon regulatory factor (IRF) family members. It is thus a property of MHC class I promoters to bind to interferon regulatory factor (IRF) family members. This may be verified, for example, by gel shift assays.

Another regulatory element, the enhancer A (containing binding sites for nuclear transcription factor κB (NF-κB)) is present in most cases. It is thus a property of MHC class I promoters to bind to nuclear transcription factor κB (NF-κB). This may be verified, for example, by gel shift assays.

In addition to ISRE, MHC class I promoters generally share another set of conserved upstream sequence motifs, consisting of three regulatory elements: the S or W box, the X1/CREX2 boxes or site α, and the Y box or enhancer B, which together are termed the SXY module. This SXY module is generally cooperatively bound by a multiprotein complex containing regulatory factor X (RFX; consisting of RFX5, RFXB/ANK and RFXAP), cAMP response element binding protein (CREB)/activating transcription factor (ATF), and nuclear factor Y (NFY), which acts as an enhanceosome driving transactivation of these genes. It is thus a property of MHC class I promoters to bind to these factors. This may be verified, for example, by gel shift assays.

In contrast, MHC class II promoters do not display enhancer A nor ISRE elements (Van den Elsen, P. J. et al, 1998, *Immunogenetics.* 48:208-221). Furthermore, RFX and CIITA in MHC class II gene regulation have been found of crucial importance as illustrated by studies with cell lines established from patients with the bare lymphocyte syndrome (BLS), a severe combined immunodeficiency due to mutations in one of the RFX subunits or CIITA (DeSandro, A. et al., 1999, *Am J Hum Genet,* 65:279-286). Also, lack of either CIITA or one of the RFX subunits affects the functioning and assembly of the MHC enhanceosome, respectively, leading to a lack of MHC class II and reduced levels of MHC class I transcription (Van den Elsen, P. J. et al. 2004, *Current Opinion in Immunology,* 16:67-75).

In one embodiment, the invention encompasses a method comprising inserting a promoter of the invention, particularly a γ2m, Ubi, MHC class II, or MHC class I promoter, into a lentiviral vector to direct expression of a CAR of the invention. The method can further comprise inserting any of the other nucleic acid elements mentioned herein, such as a DNA flap sequence.

Isolated Cells

The invention encompasses cells, particularly cells of the immune system, comprising vectors and lentiviral vector particles encoding a CAR of the invention. Preferably, the cells are T cells, including Tαβ and T☐δ cells, or NK cells.

In one embodiment, the cell contains the vector integrated into the cellular genome. In one embodiment, the cell contains the vector transiently expressing the CAR. In one embodiment, the cell produces lentiviral vector particles encoding the CAR.

In various embodiments, the invention encompasses a cell line, a population of cells, or a cell culture comprising vectors and lentiviral vector particles encoding the CAR.

Lentiviral Vector Particles

The present invention provides a method for producing a lentiviral vector particle. A lentiviral vector particle (or lentiviral particle vector) comprises a lentiviral vector in association with viral proteins. The vector is preferably an integrating vector.

In one embodiment, the lentiviral vector particles encode a CAR of the invention.

In one embodiment, the lentiviral vector particle comprises HIV-1 Gag and Pol proteins. Preferably, the lentiviral vector particle comprises subtype D, especially HIV-1$_{NDK}$, Gag and Pol proteins.

According to one embodiment of this method, the lentivector particles are obtained in a host cell transformed with a DNA plasmid.

Such a DNA plasmid can comprise:
bacterial origin of replication (ex: pUC ori);
antibiotic resistance gene (ex: KanR) for selection; and more particularly:
a lentiviral vector comprising at least one nucleic acid encoding a CAR transcriptionally linked to a β2m, Ubi, MHC class II, or MHC class I promoter.

Such a method allows producing a recombinant vector particle according to the invention, comprising the following steps of:
i) transfecting a suitable host cell with a lentiviral vector;
ii) transfecting said host cell with a packaging plasmid vector, containing viral DNA sequences encoding at least structural and polymerase (+integrase) activities of a retrovirus (preferably lentivirus); Such packaging plasmids are described in the art (Dull et al., 1998, J Virol, 72(11):8463-71; Zufferey et al., 1998, J Virol 72(12):9873-80).
iii) culturing said transfected host cell in order to obtain expression and packaging of said lentiviral vector into lentiviral vector particles; and
iv) harvesting the lentiviral vector particles resulting from the expression and packaging of step iii) in said cultured host cells.

For different reasons, it may be helpful to pseudotype the obtained retroviral particles, i.e. to add or replace specific particle envelope proteins. For instance, this may be advantageous to have different envelope proteins in order to distinguish the recombinant particle from natural particles or from other recombinant particles. In matter of vaccination strategy, pseudotyped particle vectors are more likely to escape the immune system, when this latter already developed immunity against lentiviruses. This is particularly helpful when successive injections of similar particle vectors are required for immunizing a patient against a disease.

In order to pseudotype the retroviral particles of the invention, the host cell can be further transfected with one or several envelope DNA plasmid(s) encoding viral envelope protein(s), preferably a VSV-G envelope protein.

An appropriate host cell is preferably a human cultured cell line as, for example, a HEK cell line.

Alternatively, the method for producing the vector particle is carried out in a host cell, which genome has been stably transformed with one or more of the following components: a lentiviral vector DNA sequence, the packaging genes, and the envelope gene. Such a DNA sequence may be regarded as being similar to a proviral vector according to the invention, comprising an additional promoter to allow the transcription of the vector sequence and improve the particle production rate.

In a preferred embodiment, the host cell is further modified to be able to produce viral particle in a culture medium in a continuous manner, without the entire cells swelling or dying. One may refer to Strang et al., 2005, J Virol 79(3): 1165-71; Relander et al., 2005, Mol Ther 11(3):452-9; Stewart et al., 2009, Gene Ther, 16(6):805-14; and Stuart et al., 2011, Hum gene Ther, with respect to such techniques for producing viral particles.

An object of the present invention consists of a host cell transformed with a lentiviral particle vector.

The lentiviral particle vectors can comprise the following elements, as previously defined:
cPPT/CTS polynucleotide sequence; and
a nucleic acid encoding a CAR under control of a β2m, Ubi, or MHCI promoter, and optionally one of the additional elements described above.

Preferably, the lentivector particles are in a dose of $10^6$, $2\times10^6$, $5\times10^6$, $10^7$, $2\times10^7$, $5\times10^7$, $10^8$, $2\times10^8$, $5\times10^8$, or $10^9$ TU.

Methods for Expressing a CAR in a Cell

The present invention encompasses methods for expressing a CAR in a cell, preferably in T cells, and preferably in expanded T cells. The method comprises transducing a cell with a lentiviral vector or lentiviral particle vector of the invention under conditions that allow the expression of the CAR, and preferably expanding the T cells.

The cells are preferably mammalian cells, particularly human cells. Particularly preferred are human non-dividing cells.

Preferably, the cells are primary T cells or NK cells.

The method can further comprise harvesting or isolating the CAR.

The lentiviral vector or lentiviral particle vector preferably comprises a promoter of the invention.

In one embodiment, the method comprises treating the cells with biotin to release the CAR from the hook. Preferably, the cells are treated with biotin at an initial concentration of, at least, 0.2, 0.4, 0.8. 1.6, 2.5, 5, 10, 20, 40, or 80 µM.

In one embodiment, the invention encompasses a method for expressing a CAR comprising inserting a β2m, Ubi, or MHCI promoter into a lentiviral vector such that it direct the expression of a nucleic acid encoding a CAR and transducing a cell, preferably a T or NK cell, with the vector containing the promoter, and optionally, treating the cell with biotin at an initial concentration of, at least, 0.2, 0.4, 0.8. 1.6, 2.5, 5, 10, 20, 40, or 80 µM.

Therapeutic Use of Lentiviral Vectors

The present invention further relates to the use of the lentiviral vectors according to the invention, especially in the form of lentiviral vector particles, for the preparation of therapeutic compositions or vaccines which are capable of inducing or contributing to the occurrence or improvement of an immunological reaction with the CAR encoded by the vectors.

The invention encompasses methods of administration of a lentiviral vector (or "lentivector") to a human. Preferably, the lentivector particle is an integrating lentivector particle, comprising a functional integrase protein.

Preferred modes of administration include reinfusion of the modified T cells, preferably intravenously or intra-articular administration, most preferably intra-tumoral administration.

In one embodiment, the invention comprises a method for inducing an immune response in a human comprising administering lentiviral vector particles comprising a functional integrase protein and a lentiviral vector to T or NK cells and administering the modified cells to a human; wherein the integrating lentiviral vector comprises a promoter directing expression of a CAR; and generating immunological reaction with the CAR.

The invention can also be used in treatment protocols against tumors and cancers and especially could be used in protocols for immunotherapy or vaccination therapy against cancers and tumors.

The invention further relates to an immunogenic composition comprising a lentiviral vector as previously defined.

The immunogenic compositions of the invention preferably contain cPPT and CTS sequences in the vector and vector particles to induce or to stimulate the nuclear import of the vector genome in the target cells.

During reverse transcription, cPPT and CTS sequences induce the formation of a three stranded DNA structure referred as DNA triplex, which stimulates the nuclear import of DNA vector sequence. Preferably, the vector comprises a CAR and regulatory signals of retrotranscription, expression and encapsidation of retroviral or retroviral-like origin.

The lentiviral vectors according to the invention have the ability to redirect the specificity and function of T lymphocytes and/or other immune cells. They can rapidly generate T cells targeted to a specific tumor antigen or an antigen relevant in other pathologies like auto-immune diseases.

The lentiviral vectors of the invention can be used in methods of treatment and methods of inducing an immune response comprising administering the lentiviral vector to a cell, preferably a T or NK cell, administering the cell to a host, and generating a specific immune response that redirects the specificity and function of T lymphocytes and/or other immune cells.

A particular advantage of the immunogenic compositions of the invention is that they can be used to redirect the specificity and function of T lymphocytes and other immune cells against multiple antigens against which the CAR in the vector or vector particles are directed.

As a result, the invention encompasses a composition that could be used in therapeutic vaccination protocols.

In particular, it can be used in combination with adjuvants, other immunogenic compositions, chemotherapy, or any other therapeutic treatment.

The invention encompasses a composition for administration to a human comprising lentiviral vector particles comprising a functional integrase protein and a lentiviral vector; wherein the DNA of the lentiviral vector comprises a promoter directing expression of an amino acid comprising or consisting of a CAR.

In one embodiment, the invention encompasses administering, preferably via intramuscular administration, a lentiviral vector, or cells transduced by the lentiviral vector, encoding a chimeric antigen receptor comprising a binding domain; a transmembrane domain; a hook-binding domain, preferably comprising a streptavidin-binding peptide; and an activation domain comprising a T cell activating fragment of at least 100 amino acids of SEQ ID NO:3; SEQ ID NO:4; SEQ ID NO:5; SEQ ID NO:6, SEQ ID NO:7, or SEQ ID NO:8, SEQ ID NO:33, or SEQ ID NO:34 to a human. Preferably, the lentiviral vector further comprises a hook, preferably comprising a streptavidin protein, most preferably comprising the amino acid sequence of SEQ ID NO:32, SEQ ID NO:33, or a mutant thereof having a mutation of the Glycine at amino acid 49, preferably to threonine. Preferably, the hook-binding domain comprises the amino acid sequence of SEQ ID NO:1 or is encoded by the nucleic acid sequence of SEQ ID NO:2.

The method can further comprise administering biotin to the human to release the CAR from the ER or Golgi. Preferably, the biotin is administered at an initial concentration of at least, 0.2, 0.4, 0.8. 1.6, 3.2, 5, 10, 20, 40, or 80 μM.

Having thus described different embodiments of the present invention, it should be noted by those skilled in the art that the disclosures herein are exemplary only and that various other alternatives, adaptations, and modifications may be made within the scope of the present invention. Accordingly, the present invention is not limited to the specific embodiments as illustrated herein.

EXAMPLES

Example 1. Molecular Constructions

PCR amplification of the proviral region of the pTRIPΔU3-CMV-GFP(15) was performed using direct (5'-CTTACTAGTTGGAAGGGCTAATTCACTCCCAAC-3'; SEQ ID NO:15) and reverse (5'-CATTCTAGAACTGCTA-GAGATTTTCCACACTG-3'; SEQ ID NO:16) oligonucleotides encompassing respectively the SpeI and XbaI restriction sites. The resulting fragment was digested and cloned between the SpeI and XbaI sites of the pVAX-1 plasmid (Invitrogen, Lifetech) from which the MluI site have been deleted. The resulting plasmid was named pFLAP-CMV-GFP. The SV40 sequence was amplified by PCR from the pTRIPΔU3-CMV-GFP plasmid (using the 5'-TAC-CCCGGGCCATGGCCTCCAAAAAAGCCTCCTCACT-ACTTC-3' (SEQ ID NO:17) and 5'-ACTCCCGGGTAA-TTTTTTTATTTATGCAGAGGCCGAGGCCGCC-3' (SEQ ID NO:18) oligonucleotides), and cloned into the Pml1 site of the pFLAP-CMV-GFP, the resulting plasmid being then named pFLAP-CMV-GFP-SV. The CMV promoter was amplified with direct (5'-TACACGCGTGGAGT-TCCGCGTTACATAACTTACGG-3'; SEQ ID NO:19) and reverse (5'-CGTGGATCCGATCGCGGTGTCTTCTATGG-AGGTCAAAAC-3'; SEQ ID NO:20) oligonucleotides encompassing the MluI and BamHI sites, respectively. The resulting fragment was cloned back between the MluI and BamHI sites of the pFlap-CMV-GFP-SV allowing the easy replacement of the promoters inside the lentiviral vectors. The promoter was then amplified by PCR from HEK 293T cells DNA with 5'-GCCGGCGCGCCGAGAAACCCT-GCAGGGAATTCCC-3' (SEQ ID NO:21) and 5'-CGTG-GATCCGATCGCTCGGCCCGAATGCTGTCAGCTTCA-GG-3' (SEQ ID NO:22) for the β2m promoter and cloned between the MluI and BamH1 sites of pFLAP-CMV-GFP-SV to create pFlap-β2m-SV. The amplified β2m promoter sequence is the following: GAGAAACCCTGCAGGGAAT-TCCCCAGCTGTAGTTATAAACAGAAGTTCTCCTTC-TGCTAGGTAGCATTCAAAGATCTTAATCTTCTGGG-TTTCCGTTTTCTCGAATGAAAAATGCAGGTCCGA-GCAGTTAACTGGCGGGGGCACCATTAGCAAGTCA-CTTAGCATCTC TGGGGCCAGTCTGCAAAGC- GAGGGGGCAGCCTTAATGTGCCTCCAGCCTGAAGT CCTAGAATGAGCGCCCGGTGTCCCAAGCTGGGG- CGCGCACCCCAGATCGGAGGG CGCCGATGTACAG- ACAGCAAACTCACCCAGTCTAGTGCATGCCTTCT- TAAACATCA CGAGACTCTAAGAAAAGGAAACTGA- AAACGGGAAAGTCCCTCTCTCTAACCTGGCA CTG- CGTCGCTGGCTTGGAGACAGGTGACGGTCCCTGC- GGGCCTTGTCCTGATTG GCTGGGCACGCGTTTAA- TATAAGTGGAGGCGTCGCGCTGGCGGGCATTCCT- GAA GCTGACAGCATTCGGGCCGAG (SEQ ID NO:23). The CAR can be synthetized and cloned between the BamHI and XhoI sites of the pFlap-β2m-SV, in place of the GFP gene.

For example, pFlap-β2m-GFP-SV can be digested by BamHI and XhoI, and a DNA linker containing a Multiple Cloning Site (MCS, carrying SalI, SacII, NdeI, AscI and NheI restriction sites) can be cloned between those sites, in place of the GFP gene to allow insertion of a nucleic acid sequence encoding the CAR.

The packaging plasmid pTHV-GP-N was constructed by amplifying the HIV-1 NDK genome by PCR (using the following oligonucleotides with 5'-atgcatgcgtcgacctcgagt- taatcctcatcctgtctacttgccac-3' (SEQ ID NO:24) and 5'-gcatg- catcggccggggcggcgactgGTgagagGCCACCatgggtgcgagag- cgtcagtattaag-3' (SEQ ID NO:25)). The resulting fragment has been digested by EagI and SalI restriction enzymes and inserted in the p8.74 packaging plasmid (15) from which the Eag1-SalI fragment had been previously removed.

Pseudotyping plasmids were generated by synthesizing the codon optimized genes corresponding to the vesicular stomatitis virus Indiana (GenBank #CAX62728.1), New Jersey GenBank #CAX62729.1) and Cocal (GenBank # CAX62731.1) strains. Those genes were then digested with EcoR1 and BamH1 and cloned between the corresponding restriction sites of the pVAX1 plasmid (Invitrogen, Lifetech).

The plasmids can produced using Nucleobond Xtra Maxi EF column according to manufacturer's instructions (Macherey Nagel).

Example 2. Lentiviral Production

R&D productions: Vectors can be produced by transient calcium-phosphate transfection of HEK 293T as previously described (25). HEK 293T (human embryonic kidney cell line, ATCC CRL-11268, (Graham et al. 1977)) cells were maintained in Dubelcco's modified Eagle's Medium (DMEM/High Modified, Hyclone) supplemented with 10% fetal bovine serum (FBS, PAA), 1% L-Glutamine (Eurobio), 1% Penicillin-Streptomycin (Gibco by Life technologies) and 1% Sodium Pyruvate (Gibco by Life technologies).). The cell line was kept in an incubator with humidified atmosphere of 5% $CO_2$ at 37° C. The lentiviral vectors were produced by transient transfection of HEK 293T cells using a standard calcium phosphate precipitation protocol. HEK 293T cells were seeded at $7\times10^6$ cells in 10 $cm^2$ Tissue Culture Dish (BD Falcon) in 10 mL of complete culture medium and maintained 24 h in an incubator with humidified atmosphere of 5% $CO_2$ at 37° C. to adhere. For each vector produced, one tissue culture dish is transfected as following: the lentiviral backbone plasmid pFlap-promoter-CAR_CD19 (10 μg), the pThV-Env1 encoding envelope plasmid (2 μg), and the pThV-GP packaging plasmid (10 μg) were mixed with 353 μL of sterile distilled water (Gibco by Life Technologies) and 125 μL of $CaCl_2$ (Fluka). The DNA mix is then added drop to drop to 500 μL of 37° C. prewarmed HBS 2×pH=7.3 and the 1 mL of precipitate obtained was added to the culture medium of the cells. The transfected cells were then incubated at 37° C., 5% $CO_2$. The medium was replaced 24 h after transfection by 7 mL of harvest medium without serum and the viral supernatant was harvested after an additional 24 h, and clarified by centrifugation 5 min. at 2500 rpm. The harvest clarified bulk (210 mL) is then treated 30 min. with DNase (Roche) in the presence of $MgCl_2$ (Sigma Aldrich) to avoid residual transfection DNA, and ultraconcentrated by centrifugation 1 h at 22000 rpm, 4° C. Each vector pellets are resuspended in 70 μl PBS-Lactose (40 mg/L), pooled, 30 μL aliquoted and stored at −70° C.±10° C.

For product characterization and pharmaceutical release, quality tests can be performed according to regulatory texts on vaccines: the quality control required for vaccines as per the European Pharmacopeia (section 6.16), the "guideline on quality, non-clinical and clinical aspects of live recombinant viral vectored vaccines" (EMA/CHMP/141697/2009), the "guideline on development and manufacture of lentiviral vectors" (CHMP/BWP/2458/03); regulatory text on gene therapy medicinal products: the quality controls required for gene transfer medicinal products for human use as per the European Pharmacopeia (section 5.14), the quality controls specific to gene therapy products as defined in the "note for guidance on the quality, preclinical and clinical aspects of gene transfer medicinal products" (CHMP/BWP/3088/99); regulatory texts on biotechnological products (ICH Q5A to ICH Q5E); regulatory texts on specifications (ICH Q6A and ICH Q6B) and the quality controls required for parenteral preparations as per the European Pharmacopeia (section 7.0).

Example 3. Lentiviral Vector Titration qPCR reactions: HEK 293T cells are seeded in 6-well plates (BD Falcon) in culture medium and incubated for 4 h at 37° C., 5% CO2 in moist atmosphere. Cells are transduced with 3 successive dilutions of lentiviral vector. 72 h post-incubation, cells are harvested and transduced HEK 293T cell pellets are produced. Total genomic DNA from transduced cell-pellets is extracted using a method based on QIAGEN QIAamp DNA mini kit handbook. Proviral quantification is performed using Taqman qPCR. The amplification is performed with the Master Mix (Fermentas Thermo Scientific), the Flap A (CCCAAGAACCCAAGGAACA; SEQ ID NO:26) and Flap S (AGACAA GATAGAG-GAAGAGCAAAAC; SEQ ID NO:27) primers and LENTI TM probe (6FAM-AACCATTAGGAGTAGCACCCAC-CAAGG-BBQ; SEQ ID NO:52). Normalization is performed with the quantification of the actin gene (same Mix, Actine A-CGGTGAGGATCTTCATGAGGTAGT-(SEQ ID NO:28), Actine S-AACACCCCAGCCATGTACGT-(SEQ ID NO:29) primers and HUMURA ACT TM probe-6FAM-CCAGCCAGGTCCAGACGCAGGA-BBQ-(SEQ ID NO:30). Both reactions are achieved on MasterCycler Ep Realplex S (Eppendorf, 2 min at 50° C., 10 min at 95° C. and 40 cycles of 15 seconds at 95° C. and 1 min at 63° C.). The analysis is performed on MasterCycler Ep Realplex Software.

Example 4. Regulated CARs

Lentiviral vectors were generated encoding CARs. The CAR_CD19 2nd and 3rd generation sequences (SEQ ID NO:39 and SEQ ID NO:40) were purchased from GeneArt (Lifetech), and cloned replacing the GFP gene between BamHI and XhoI restrictions sites of the pFlap-ΔU3-β2m-GFP, pFlap-ΔU3-HLA-A2-GFP, pFlap-ΔU3-HLA-DRα-GFP or pFlap-ΔU3-UBC-GFP, depending of the required promoter.

CARs were generated as a fusion protein with SBP at 3 different positions. The lentiviral vectors were further modified to contain a hook for the ER fused to a core Streptavidin protein. The promoter was an β2m promoter.

These lentiviral vectors will be used in in vitro and animal models of cancer. Biotin will be administered at 40 µM (with a titration of higher and lower concentrations) initial concentration to test for release from the ER. First, migration of the CAR to the surface of the cell (GFP in place of the binding domain or between the signal sequence and the binding domain) will be analyzed in vitro. Next, the same will be performed in animal models (mice and rats) by injection of CAR-T cells and evaluation of the migration at the surface of cells (GFP) from the animal.

Both "second generation" CAR (2 intra cytoplasmic activating domains) and "third generation" CAR (3 intra cytoplasmic activating domains) constructs will be generated containing a hook-binding domain (SBP). Initially, the binding domains evaluated will be anti-CD19, anti-PDL-1, anti-PD1, anti-hedgehog, anti-CD123, and anti-CD123/CD33.

CARMIN 1.0: development of lentiviral vectors coding for CAR of the second (containing the CD3_, and the 4-1BB cosignaling domains) and third generations (containing the CD3_, the CD28 and the 4-1BB domains) directed against CD19 (for CD19+ leukemias and lymphomas), LMP-1 and -2 (for EBV-induced leukemias). The lentiviral vectors allow optimal expression of CAR in T cells and the impact on the efficacy of CAR-T cells is under investigation. Hematological malignancies can be used as a benchmark.

CARMIN 2.0: development of a switchable on/off system which is based on a W protein anchored to the membrane of the endoplasmic reticulum (ER) through a hook, and its binding partner Y introduced into the CAR structure. The interaction between the X-hook (e.g., Streptavidin) and the Y (e.g., Streptavidin-Binding Protein)-CAR allows the CAR retention inside the ER. The addition of a Z protein (e.g., Biotin) displaces the equilibrium of binding of X towards Z instead of Y, thus leading to the release of the CAR from the ER and its expression to the cytoplasmic membrane. The release of the CAR will stop with Z exhaustion (or antagonist) and remaining cells can be easily reactivated through reintroduction of the Z inducer.

Hook and CAR are vectorized in one lentivector and can be used in clinics (b2m-HOOK-IRES-CAR). Evaluations can be performed in vitro both on immortalized cells (HEK293T, Jurkat, HeLa) and on primary cells (T-cells). This system will increase safety of CAR-T cells. A switchable CD19-CAR system can be evaluated in vitro for expression and in vivo for efficacy.

Most of the scFv used to date are of murine origin. Neutralizing antibodies against these murine scFv can limit the efficacy of CAR. As an alternative, we will develop camelid nanobodies to be used as binding domains since they are highly homologous to the human VH domain of antibodies and they display high antigen binding capacities. The proof-of-concept will be made with a second generation CAR containing a nanobody directed against Her2 as a binding domain. These technological platforms allows flexibility and reactivity in the CAR design, production and evaluation, thus leading to the generation of optimal CAR-T cells. This differentiated inductible and reversible (ON/OFF) CAR T-cell technology is aimed to be delivered at the patient's bedside (automated process).

Example 5. Expression in Human T Cells

Peripheral blood mononuclear cells (PBMC) were purified from peripheral blood by gradient density centrifugation on Ficoll. After PBMC washing, CD3+ T cells were purified by negative magnetic selection (ie unwanted cells were magnetically labelled while T cells were left untouched) using the Pan T Cell Isolation Kit (Miltenyi). This step is required to obtain a highly purified T cell population. According to the yield obtained after this step of isolation, $10^7$ to $10^8$ T cells were cultured at $2.5 \times 10^6$/ml in an optimized serum-free cell culture medium developed for the cultivation and expansion of human T cells (TexMACS medium, Miltenyi). These T cells are activated by the T cell Activation/Expansion kit from Miltenyi. The kit consists of anti-biotin MACSiBead Particles and biotinylated antibodies against human CD2, CD3 and CD28. Anti-biotin MACSiBead Particles loaded with biotinylated antibodies are used to mimic antigen-presenting cells and to activate T cells. An optimal activation of T cells is accomplished by using one loaded anti-biotin MACSiBead Particle per two cells. T cells are activated for 3 days. Transduction of activated T cells was then performed at a MOI of 4 which means that 1 T cell is incubated with 4 transduction units of lentiviral particles. CAR expression was assessed by flow cytometry 48 or 72 h lentiviral particle addition, by staining the murine CD19-binding domain with a biotinylated goat anti-mouse IgG followed by streptavidin conjugated to phycoerythrin. T cell subpopulations were characterized by CD3, CD4 and CD8 staining. This allowed specific detection of the CAR on the surface of T cells. The whole process was performed with the TexMACS medium allowing survival and expansion of T cells.

Example 6. Structure and Expression of CAR-RUSH

Qualified blood was obtained from the Etablissement Français du Sang (Rungis, France). Peripheral Blood Mononuclear Cells (PBMC) were purified by Ficoll (Lymphocyte Separation Medium, Eurobio) gradient density separation. T cells were then purified from PBMC by magnetic isolation using the Pan T cell isolation kit (Miltenyi). T cells were separated according to the manufacturer's instructions. T cells were put in culture at a concentration of $2.5 \times 10^6$ cells/ml in TexMACS medium (Miltenyi) at 37° C./5% CO2 and activated 3 days by the T cell activation/expansion kit (anti-CD2/-CD3/-CD28 nanoparticles prepared according the manufacturer's instructions) from Miltenyi at a bead:T cell ratio of 1:2. After activation, T cells were harvested, counted and put in culture in TexMACS medium in 24 well-plates at 37° C./5% CO2. Transduction was performed by adding directly into wells lentiviral vectors at different MOI. The different lentiviral vectors tested were: (i) the 2nd generation anti-CD19 CAR containing the 4-1BB and the CD3zeta intracellular domains; (ii) the same vector containing the streptavidin binding protein at three different positions (CAR-SBP1, CAR-SBP2, CAR-SBP3).

The volume of vector to add to each well according to the MOI was calculated as follows: volume to be added (µl)= (MOI×number of cells (in millions)/concentration of vector (transduction unit/ml))×1000.

200 000 cells were transduced at a MOI of 10 with a vector titer at $3.10^9$ TU/ml->volume of vector to be added (µl)=(10×0.2×10⁶/3×10⁹)×1000=0.51 µl. Human recombinant IL-2 (Miltenyi) was added the day of the transduction at 50 IU/ml. At day 3, transduced T cells were harvested, washed extensively with DPBS 1× and immunostaining of molecules of interest was performed in 96 well-plates. T cells were first incubated with a viability dye (Fixable Viability Dye, eBiosciences) conjugated to eFluor 780 and incubated 30 minutes at 4° C. The incubation was performed in azide-free and protein-free DPBS1×. Cells were then washed with DPBS 1× and then incubated with a biotinylated Goat anti-mouse IgG (Fab')2 (Jackson ImmunoResearch) for 30 minutes à 4° C. After incubation, cells were washed in autoMACS running buffer (Miltenyi) and the third incubation was performed with a mix of streptavidin conjugated to phycoerythrin (Jackson ImmunoResearch) and mouse anti-human CD3 conjugated to PE-Cy7 (BD Biosciences). Incubation was done for 30 minutes at 4° C. After this third incubation, cells were washed in autoMACS running buffer and fixed in CellFIX (BD Biosciences) before acquisition on a MACSQuant analyzer (Miltenyi). Flow cytometry data were analyzed using the FlowJo software.

Example 7. Expression and Behaviour of CAR-RUSH Constructs Following Co-Transduction with a Lentivector Encoding a HOOK-Streptavidin, and Biotin Treatment Qualified blood was obtained from the Etablissement Français du Sang (Rungis, France). Peripheral Blood Mononuclear Cells (PBMC) were purified by Ficoll (Lymphocyte Separation Medium, Eurobio) gradient density separation. T cells were then purified from PBMC by magnetic isolation using the Pan T cell isolation kit (Miltenyi). T cells were separated according to the manufacturer's instructions. T cells were put in culture at a concentration of 2.5×10⁶ cells/ml in TexMACS medium (Miltenyi) at 37° C./5% CO₂ and activated 3 days by the T cell activation/expansion kit (anti-CD2/-CD3/-CD28 nanoparticles prepared according the manufacturer's instructions) from Miltenyi at a bead:T cell ratio of 1:2.

After activation, T cells were harvested, counted and put in culture in TexMACS medium in 24 well-plates at 37° C./5% CO₂. Co-transduction was performed by adding directly into wells lentiviral vectors at different MOI. The two lentiviral vectors tested were: (i) a hook-streptavidin vector and (ii) the 2nd generation anti-CD19 CAR containing the 4-1BB and the CD3zeta intracellular domains with the streptavidin binding protein at three different positions (CAR-SBP1, CAR-SBP2 and CAR-SBP3).

The volume of each vector to add to each well according to the MOI was calculated as follows: volume to be added (µl)=(MOI×number of cells (in millions)/concentration of vector (transduction unit/ml))×1000

Human recombinant IL-2 (50 IU/ml; Miltenyi) and biotin (40 µM; Sigma-Aldrich) were added the day of the transduction.

At day 3, transduced T cells were harvested, washed extensively with DPBS 1× and immunostaining of molecules of interest was performed in 96 well-plates. T cells were first incubated with a viability dye (Fixable Viability Dye, eBiosciences) conjugated to eFluor 780 and incubated 30 minutes at 4° C. The incubation was performed in azide-free and protein-free DPBS1×. Cells were then washed with DPBS 1× and then incubated with a biotinylated Goat anti-mouse IgG (Fab')2 (Jackson ImmunoResearch) for 30 minutes à 4° C. After incubation, cells were washed in autoMACS running buffer (Miltenyi) and the third incubation was performed with a mix of streptavidin conjugated to phycoerythrin (Jackson ImmunoResearch) and mouse anti-human CD3 conjugated to PE-Cy7 (BD Biosciences). Incubation was done for 30 minutes at 4° C. After this third incubation, cells were washed in autoMACS running buffer and fixed in CellFIX (BD Biosciences) before acquisition on a MACSQuant analyzer (Miltenyi). Flow cytometry data were analyzed using the FlowJo software.

Example 8. Expression and Behavior of CAR-RUSH Bicistronic Constructs

Qualified blood was obtained from the Etablissement Français du Sang (Rungis, France). Peripheral Blood Mononuclear Cells (PBMC) were purified by Ficoll (Lymphocyte Separation Medium, Eurobio) gradient density separation. T cells were then purified from PBMC by magnetic isolation using the Pan T cell isolation kit (Miltenyi). T cells were separated according to the manufacturer's instructions. T cells were put in culture at a concentration of 2.5×106 cells/ml in TexMACS medium (Miltenyi) at 37° C./5% CO2 and activated 3 days by the T cell activation/expansion kit (anti-CD2/-CD3/-CD28 nanoparticles prepared according the manufacturer's instructions) from Miltenyi at a bead:T cell ratio of 1:2.

After activation, T cells were harvested, counted and put in culture in TexMACS medium in 24 well-plates at 37° C./5% CO2. Transduction was performed by adding directly into wells lentiviral vectors at different MOI. The different lentiviral vectors tested were; (i) the "classical" 2nd generation anti-CD19 CAR; (ii) three constructions containing the hook-streptavidin, an IRES and the 2nd generation anti-CD19 CAR containing the 4-1BB and the CD3zeta intracellular domains with the streptavidin binding protein at three different positions (hook-IRES-CAR-SBP1, hook-IRES-CAR-SBP2, hook-IRES-CAR-SBP3).

The volume of vector to add to each well according to the MOI was calculated as follows: volume to be added (µl)=(MOI×number of cells (in millions)/concentration of vector (transduction unit/ml))×1000.

The different MOI tested were 10, 20 or 30 depending on the experiment.

Human recombinant IL-2 (50 IU/ml; Miltenyi) and biotin (40 µM; Sigma-Aldrich) were added the day of the transduction.

At days 3 and 7, transduced T cells were harvested, washed extensively with DPBS 1× and immunostaining of molecules of interest was performed in 96 well-plates. T cells were first incubated with a viability dye (Fixable Viability Dye, eBiosciences) conjugated to eFluor 780 and incubated 30 minutes at 4° C. The incubation was performed in azide-free and protein-free DPBS1×. Cells were then washed with DPBS 1× and then incubated with a biotinylated Goat anti-mouse IgG (Fab')2 (Jackson ImmunoResearch) for 30 minutes at 4° C. After incubation, cells were washed in autoMACS running buffer (Miltenyi) and the third incubation was performed with a mix of streptavidin conjugated to phycoerythrin (Jackson ImmunoResearch) and mouse anti-human CD3 conjugated to PE-Cy7 (BD Biosciences). Incubation was done for 30 minutes at 4° C. After this third incubation, cells were washed in autoMACS running buffer and fixed in CellFIX (BD Biosciences) before acquisition on a MACSQuant analyzer (Miltenyi). Flow cytometry data were analyzed using the FlowJo software.

Example 9. CAR-RUSH System Switch Evaluation (OFF/ON/OFF)

Qualified blood was obtained from the Etablissement Français du Sang (Rungis, France). Peripheral Blood Mononuclear Cells (PBMC) were purified by Ficoll (Lymphocyte Separation Medium, Eurobio) gradient density separation. T cells were then purified from PBMC by magnetic isolation using the Pan T cell isolation kit (Miltenyi). T cells were separated according to the manufacturer's instructions. T cells were put in culture at a concentration of $2.5 \times 10^6$ cells/ml in TexMACS medium (Miltenyi) at 37° C./5% CO2 and activated 3 days by the T cell activation/expansion kit (anti-CD2/-CD3/-CD28 nanoparticles prepared according the manufacturer's instructions) from Miltenyi at a bead:T cell ratio of 1:2.

After activation, T cells were harvested, counted and put in culture in TexMACS medium in 24 well-plates at 37° C./5% $CO_2$. Transduction was performed by adding directly into wells lentiviral vectors at different MOI. The different lentiviral vectors tested were; (i) the "classical" 2nd generation anti-CD19 CAR; (ii) three constructions containing the hook-streptavidin, an IRES and the 2nd generation anti-CD19 CAR containing the 4-1BB and the CD3zeta intracellular domains with the streptavidin binding protein at three different positions (hook-IRES-CAR-SBP1, hook-IRES-CAR-SBP2, hook-IRES-CAR-SBP3).

The volume of vector to add to each well according to the MOI was calculated as follows: volume to be added (µl)= (MOI×number of cells (in millions)/concentration of vector (transduction unit/ml))×1000

The different MOI tested were 10 and 20.

Human recombinant IL-2 (50 IU/ml; Miltenyi) and biotin (40 µM; Sigma-Aldrich) were added the day of the transduction.

At day 3, cells were washed and biotin was added or not at 40 µM to re-induce CAR-SBP expression.

At day 7, transduced T cells were harvested, washed extensively with DPBS 1× and immunostaining of molecules of interest was performed in 96 well-plates. T cells were first incubated with a viability dye (Fixable Viability Dye, eBiosciences) conjugated to eFluor 780 and incubated 30 minutes at 4° C. The incubation was performed in azide-free and protein-free DPBS1×. Cells were then washed with DPBS 1× and then incubated with a biotinylated Goat anti-mouse IgG (Fab')2 (Jackson ImmunoResearch) for 30 minutes at 4° C. After incubation, cells were washed in autoMACS running buffer (Miltenyi) and the third incubation was performed with a mix of streptavidin conjugated to phycoerythrin (Jackson ImmunoResearch) and mouse anti-human CD3 conjugated to PE-Cy7 (BD Biosciences). Incubation was done for 30 minutes at 4° C. After this third incubation, cells were washed in autoMACS running buffer and fixed in CellFIX (BD Biosciences) before acquisition on a MACSQuant analyzer (Miltenyi).

We claim:

1. A chimeric antigen receptor comprising:
   a binding domain;
   a transmembrane domain;
   a hook-binding domain comprising a streptavidin-binding peptide; and
   an activation domain comprising a T cell activating fragment comprising an amino acid sequence having at least 90% amino acid sequence identity to the amino acid sequence selected from the group consisting of:
   the amino acid fragment of sequence PKLCYLLDGIL-FIYGVILTALFLRVKFSRSADAPAYQQGQNQLYN-ELNLGRREEYDVLDKRRGRDPEMGGKPQRRK-NPQEGLYNELQKDKMAEAYSEIGMKGERRRG-KG HDGLY from SEQ ID NO:3;
   SEQ ID NO:4;
   the amino acid fragment of sequence KRGRKKLLY-IFKQPFMRPVQTTQEEDGCSCRFPEEEEGGCEL from SEQ ID NO:5;
   SEQ ID NO:6;
   SEQ ID NO:7,
   SEQ ID NO:8,
   SEQ ID NO:33, and
   SEQ ID NO:34,
   the hook-binding domain being encoded by the nucleic acid sequence SEQ ID NO:2;
   the hook-binding domain being located in the intracytoplasmic region, between the transmembrane domain and the activation domain, between two activation domains or at the intracytoplasmic C-terminus of the chimeric antigen receptor;
   the binding domain being located in the extracytoplasmic region of the chimeric antigen receptor; and
   the T cell activating fragment being located in the intracytoplasmic region of the chimeric antigen receptor.

2. The chimeric antigen receptor of claim 1, wherein the binding domain comprises a single-chain Fv antibody or a nanobody.

3. The chimeric antigen receptor of claim 1, wherein the chimeric antigen receptor comprises the amino acid sequence of any of SEQ ID NO:46, SEQ ID NO:48, or SEQ ID NO:50.

4. The chimeric antigen receptor of claim 1, wherein the activation domain comprises a T cell activating fragment comprising the amino acid sequence selected from the group consisting of:
   the amino acid fragment of sequence PKLCYLLDGIL-FIYGVILTALFLRVKFSRSADAPAYQQGQNQLYN-ELNLGRREEY DVLDKRRGRDPEMGGKPQRRK-NPQEGLYNELQKDKMAEAYSEIGMKGERRRG KGHDGLY from SEQ ID NO:3;
   SEQ ID NO:4;
   the amino acid fragment of sequence KRGRKKLLY-IFKQPFMRPVQTTQEEDGCSCRFPEEEEGGCEL from SEQ ID NO:5;
   SEQ ID NO:6,
   SEQ ID NO:7,
   SEQ ID NO:8,
   SEQ ID NO:33, and
   SEQ ID NO:34.

5. The chimeric antigen receptor of claim 1, wherein the activation domain comprises the amino acid fragment of sequence KRGRKKLLYIFKQPFMRPVQTTQEEDGC-SCRFPEEEEGGCEL from the amino acid sequence SEQ ID NO:5 and
   the amino acid fragment of sequence PKLCYLLD GIL-FIYGVILTALFLRVKFSRSADAPAYQQGQNQLY-NELNLGRREEY DVLDKRRGRDPEMGGKPQR-RKNPQEGLYNELQKDKMAEAYSEIGMKGERRRG KGHDGLY from the amino acid sequence SEQ ID NO:3.

* * * * *